(12) United States Patent
Wang et al.

(10) Patent No.: US 9,784,748 B2
(45) Date of Patent: Oct. 10, 2017

(54) METHODS FOR DETERMINING ANTI-DRUG ANTIBODY ISOTYPES

(71) Applicant: NESTEC S.A., Vevey (CH)

(72) Inventors: Shui Long Wang, San Diego, CA (US); Linda Ohrmund, San Diego, CA (US); Scott Hauenstein, San Diego, CA (US); Sharat Singh, Rancho Santa Fe, CA (US)

(73) Assignee: NESTEC S.A., Vevey (CH)

( * ) Notice: Subject to any disclaimer, the term of this patent is extended or adjusted under 35 U.S.C. 154(b) by 0 days.

(21) Appl. No.: 13/865,139

(22) Filed: Apr. 17, 2013

(65) Prior Publication Data

US 2013/0344621 A1    Dec. 26, 2013

Related U.S. Application Data

(63) Continuation of application No. PCT/US2011/056777, filed on Oct. 18, 2011.

(60) Provisional application No. 61/394,269, filed on Oct. 18, 2010.

(51) Int. Cl.
| | | |
|---|---|---|
| *G01N 33/68* | (2006.01) | |
| *G01N 33/564* | (2006.01) | |
| *G01N 33/94* | (2006.01) | |

(52) U.S. Cl.
CPC ....... *G01N 33/6854* (2013.01); *G01N 33/564* (2013.01); *G01N 33/94* (2013.01)

(58) Field of Classification Search
None
See application file for complete search history.

(56) References Cited

U.S. PATENT DOCUMENTS

| | | |
|---|---|---|
| 4,459,359 A | 7/1984 | Neurath |
| 4,965,069 A | 10/1990 | Quash et al. |
| 5,094,740 A | 3/1992 | Brandley et al. |
| 5,223,395 A | 6/1993 | Gero |
| 5,582,998 A | 12/1996 | Adolf et al. |
| 5,698,419 A | 12/1997 | Wolpe et al. |
| 5,795,967 A | 8/1998 | Aggarwal et al. |
| 5,837,242 A | 11/1998 | Holliger et al. |
| 6,284,471 B1 | 9/2001 | Le et al. |
| 6,309,888 B1 | 10/2001 | Holvoet et al. |
| 6,444,461 B1 | 9/2002 | Knapp et al. |
| 6,906,183 B2 | 6/2005 | Romisch |
| 7,189,515 B2 | 3/2007 | Buechler et al. |
| 7,276,477 B2 | 10/2007 | Osslund et al. |
| 7,524,502 B2 | 4/2009 | Hellendoorn et al. |
| 7,601,335 B2 | 10/2009 | McCutcheon et al. |
| 7,662,569 B2 * | 2/2010 | Targan et al. .................. 435/7.1 |
| 8,574,855 B2 | 11/2013 | Singh et al. |
| 8,865,417 B2 | 10/2014 | Singh et al. |
| 2003/0040027 A1 | 2/2003 | Ritter et al. |
| 2003/0077246 A1 | 4/2003 | Welcher et al. |
| 2004/0022792 A1 | 2/2004 | Klinke et al. |
| 2004/0157782 A1 | 8/2004 | Doronina |
| 2005/0054005 A1 | 3/2005 | Ellis et al. |
| 2005/0181483 A1 * | 8/2005 | Sawyer .................. C07K 16/00 435/70.21 |
| 2006/0003384 A1 * | 1/2006 | Wagner et al. ................ 435/7.1 |
| 2006/0078944 A1 | 4/2006 | Kuai et al. |
| 2006/0110407 A1 | 5/2006 | Stopera et al. |
| 2006/0240480 A1 | 10/2006 | Curdt et al. |
| 2006/0253263 A1 | 11/2006 | Meshkin |
| 2007/0077249 A1 | 4/2007 | Silence et al. |
| 2008/0280311 A1 | 11/2008 | Strohner |
| 2009/0035216 A1 | 2/2009 | Svenson et al. |
| 2009/0162374 A1 * | 6/2009 | Geraghty ......... A61K 39/39541 424/153.1 |
| 2009/0234202 A1 | 9/2009 | Goix et al. |
| 2009/0275496 A1 | 11/2009 | Baldwin et al. |
| 2010/0130367 A1 | 5/2010 | Murthy et al. |
| 2010/0330156 A1 | 12/2010 | Liu |
| 2012/0329172 A1 | 12/2012 | Singh |
| 2013/0266963 A1 | 10/2013 | Hauenstein et al. |
| 2013/0295685 A1 | 11/2013 | Singh et al. |

(Continued)

FOREIGN PATENT DOCUMENTS

| | | |
|---|---|---|
| CN | 102695955 A | 9/2012 |
| CN | 103782172 A | 5/2014 |

(Continued)

OTHER PUBLICATIONS

Svenson et al., Monitoring patients treated with anti-TNFα biopharmaceuticals: assessing serum infliximab and anti-infliximab antibodies, Rheumatology, 46, (2007), p. 1828-1834.*
Cisbio Bioassays. "HTRF Human Kappa and Lambda MAb Assay: A New Solution for Human IgG Characterisation." (2009). URL: http://www.biolab.cn/plus/view-241835-1.html. Accessed on Feb. 20, 2014.*
Deventer et al., Anti-tumour necrosis factor therapy in Crohn's disease: where are we now? Gut., 51(3), (2002), p. 362-363.*
Harlow & Lane (Harlow, E. and Lane, D., Antibodies: A Laboratory Manual (1988) Cold Spring Harbor Laboratory Press, Cold Spring Harbor, NY, p. 7-10).*
Bendtzen et al., Individualized monitoring of drug bioavailability and immunogenicity in Rheumatoid Arthritis patients treated with the Tumor Necrosis Factor α Inhibitor Infliximab, Arthritis and Rheumatism, 54(12), (2006), p. 3782-3789.*

(Continued)

*Primary Examiner* — Christine Foster
*Assistant Examiner* — Ellen J Marcsisin
(74) *Attorney, Agent, or Firm* — Kilpatrick Townsend and Stockton LLP

(57) ABSTRACT

The present invention provides assay methods for the determination of one or more anti-drug antibody (ADA) isotypes in a sample. As a non-limiting example, the assays of the present invention are particularly useful for determining different ADA isotypes in samples from ADA-positive patients receiving an anti-TNFα drug such as REMICADE™ (infliximab) or HUMIRA™ (adalimumab). The present invention also provides methods for optimizing therapy and/or reducing toxicity in subjects receiving TNFα inhibitors for the treatment of TNFα-mediated disease or disorders.

15 Claims, 53 Drawing Sheets

(56) References Cited

U.S. PATENT DOCUMENTS

| | | |
|---|---|---|
| 2014/0045276 A1 | 2/2014 | Singh et al. |
| 2014/0051184 A1 | 2/2014 | Singh et al. |
| 2014/0057367 A1 | 2/2014 | Singh et al. |
| 2014/0186973 A1 | 7/2014 | Hauenstein et al. |
| 2015/0024404 A1 | 1/2015 | Singh et al. |

FOREIGN PATENT DOCUMENTS

| | | |
|---|---|---|
| EP | 0440044 | 8/1991 |
| EP | 0492448 A1 | 7/1992 |
| EP | 0642021 A2 | 3/1995 |
| EP | 0882984 A1 | 12/1998 |
| EP | 1237926 B1 | 9/2002 |
| EP | 1769244 | 4/2007 |
| EP | 1902320 | 3/2008 |
| EP | 2676137 | 12/2014 |
| JP | H05-000096 A | 1/1993 |
| JP | 05-066222 A2 | 3/1993 |
| JP | H07-110331 A | 4/1995 |
| JP | 07-140144 A2 | 6/1995 |
| JP | H11-500607 A | 1/1999 |
| JP | 2001-249127 A | 9/2001 |
| JP | 2007-147367 | 6/2007 |
| JP | 2013-508739 | 3/2013 |
| WO | 96/20219 A2 | 7/1996 |
| WO | 2005/019271 A1 | 3/2005 |
| WO | 2006/004958 A2 | 1/2006 |
| WO | 2007/009469 A2 | 1/2007 |
| WO | 2009/091240 A1 | 7/2009 |
| WO | WO 2011/056590 A1 | 5/2011 |
| WO | 2012/054532 A1 | 4/2012 |
| WO | 2012/154253 A1 | 11/2012 |
| WO | 2013/006810 A1 | 1/2013 |
| WO | 2014/083520 A2 | 6/2014 |

OTHER PUBLICATIONS

HHS, FDA, CDER, CBER; Guidance for Industry Assay Development for Immunogenicity Testing of Therapeutic Proteins. Draft Guidance. (2009). 24 pages, retrieved from http://www.fda.gov/Drugs/GuidanceComplianceRegulatoryInformation/Guidances/UCM192750.*
Koren et al. Recommendations on risk-based strategies for detection and characterization of antibodies against biotechnology products, Journal of Immunological Methods, 333, (2008), p. 1-9.*
English Machine Translation of CN103782172A (published May 7, 2014, cited IDS filed Dec. 15, 2016), 47 pages.*
English Machine Translation of JP 07-140144 (published Jun. 2, 1995, cited IDS filed Dec. 15, 2016), abstract only, 1 page.*
English Machine Translation of JP 2013-508739 (published May 7, 2013, cited IDS filed Dec. 15, 2016), 53 pages.*
Benucci et al., No correlations between the development of specific IgA and IgM antibodies against anti-TNF blocking agents, disease activity and adverse side reactions in patients with rheumatoid arthritis, The Open Rheumatology Journal, (2013), 7, p. 75-80.*
Hagg, D. et al. "Measurement and biological correlates of antibody bioactivity during antibody immunotherapies," J. of Immunological Methods, Oct. 1998; vol. 219, No. 1-2, pp. 7-21.
Hosono, M., et al. "Human/mouse chimeric antibodies show low reactivity with human anti-murine antibodies (HAMA)," Brit. J. Cancer; 1992; vol. 65, No. 2, pp. 197-200.
Reynolds, J., et al.; "Anti-murine antibody response to mouse monoclonal antibodies: clinical findings and implications," Int. J. Radiation Appl. Instrument, Part B: Nuclear Medicine and Biology; 1989; vol. 16, No. 2; pp. 121-125.
Van Schouwenburg, Pauline, et al.; "A novel method for the detection of antibodies to adalimumab in the presence of drug reveals 'hidden' immunogenicity in rheumatoid arthritis patients," J. Immunological Methods; Sep. 2010; vol. 362, No. 1-2; pp. 82-88.
Wang, Shui Long, et al.; "Analysis of Anti-drug Antibodies (ADA) to Adalimumab in Patient Serum Using a Novel Homogeneous Mobility Shift Assay," Amer. J. of Gastroenterology; Oct. 2010; vol. 105, suppl. 1; pp. S444-S445.
Int. Search Report of PCT/US2011/056777, mailed Feb. 14, 2012.
Aarden, L. et al., "Immunogenicity of anti-tumor necrosis factor antibodies—toward improved methods of anti-antibody measurement," Current Opinion in Immunology, 2008, 20(4): 431-435.
Arcangelo & Peterson, Pharmacotherapeutics for Advanced Practice: A Practical Approach, Philadelphia, PA, 2006, vol. 536, p. 18.
Aybay, C. et al., "Demonstration of specific antibodies against infliximab induced during treatment of a patient with ankylosing spondylitis," Rheumatology International, Clin. and Exper. Invest., 2006, 26(5):473-480.
Bendtzen, K. et al., "Individualized monitoring of drug bioavailability and immunogenicity in rheumatoid arthritis patients treated with the tumor necrosis factor alpha inhibitor infliximab," Arthritis & Rheumatism, 2006, 54(12):3782-3789.
Bourdage et al., "An affinity capture elution (ACE) assay for detection of anti-drug antibody to monoclonal antibody therapeutics in the presence of high levels of drug," J. Immunol. Methods, 2007, 327(1-2):10-17.
Cheifetz, A. et al., "Monoclonal antibodies: immunogenicity, and associated infusion reactions," Mount Sinai J. Medicine, 2005, 72(4):250-256.
Elliott, M. et al., "Repeated therapy with monoclonal antibody to tumour necrosis factor alpha (cA2) in patients with rheumatoid arthritis," Lancet, 1994, 334(8930):1125-1127.
Harris, Quantitative Chemical Analysis, Sixth Ed., New York, W.H. Freeman Co., 2003, p. 85-86.
Invitrogen, "Looking on the bright side with Alexa Fluor® secondary antibodies," 2008, URL http://www.jimmunol.org/content/181/3/local/advertising.pdf, retrieved on Oct. 11, 2013.
Kawate, T. et al., "Fluorescence-detection size-exclusion chromatography for precrystallization screening of integral membrane proteins," Structure, 2006, 14:673-681.
Lofgren, J. et al., "Detection of neutralizing anti-therapeutic protein antibodies in serum or plasma samples containing high levels of the therapeutic protein," J. Immunol. Meth., 2006, 308(1-2):101-108.
Panchuk-Voloshina, N. et al., "Alexa dyes, a series of new fluorescent dyes that yield exceptionally bright, photostable conjugates," J. Histochem & Cytochem., 1999, 47(9):1179-1188.
Patton et al., "An acid dissociation bridging ELISA for detection of antibodies directed against therapeutic proteins in the presence of antigen," J. Immunol. Meth., 2005, 304(1-2):189-195.
Scallon, B. et al., "Binding and functional comparisons of two types of tumor necrosis factor antagonists," J. Pharmacol. Exper. Ther., 2002, 301(2):418-426.
Sickert, D. et al., "Improvement of drug tolerance in immunogenicity testing by acid treatment on Biacore," J. Immunol. Meth., 2008, 334(1-2):29-36.
Smith et al., "Detection of antibodies against therapeutic proteins in the presence of residual therapeutic protein using a solid-phase extraction with acid dissociation (SPEAD) sample treatment prior to ELISA," Regulatory Toxicology and Pharmacology, 2007, 49(3): 230-237.
Tayyab, S. et al., "Size exclusion chromatography and size exclusion HPLC of proteins," Biochemical Education, 1991, 19(3):149-152.
Van Der Laken, C. et al., "Imaging and serum analysis of immune complex formation of radiolabeled infliximab and anti-infliximab in responders and non-responders to therapy for rheumatoid arthritis," Ann. Rheum. Dis., 2007, 66(2):253-256.
Flood, J., "Tumor necrosis factor inhibitors in the treatment of chronic inflammatory diseases: A review of immunogenicity and potential implications," Suppl. to Managed Care, 2009, 18(4):1-5.
Gisbert, Javier et al., "Loss of Response and Requirement of Infliximab Dose Intensification in Crohn's Disease: A Review," Journal of Gastroenterology, Mar. 2009, vol. 104, pp. 760-767.
Harris, Quantitative Chemical Analysis, Sixth Ed., New York, W.H. Freeman Co., 2003, p. 91.
O'Keefe, Michael, Ed., Residue Analysis in Food Principles and Applications, Amsterdam, Hardwood Academic Publishers, 2000, p. 20.
Rojas, J.R. et al., "Formation, distribution, and elimination of infliximab and anti-infliximab immune complexes in cynomolgus monkeys," JPET, May 1, 2005, 313(2):578-585.

(56) References Cited

OTHER PUBLICATIONS

Molecular Probes, Inc., "BioParticles® Fluorescent Particles and Opsonizing Reagents," Product Information, Mar. 9, 2001, pp. 1-3, found online at http://tools.lifetechnologies.com/content/sfs/manuals/mp02701.pdf on Dec. 8, 2014.

Chernesky & Mahony, "Immunoassays: principles and assay design," in Virology Methods Manuals, Mahy & Kangro (Eds.), pp. 123-124, San Diego, CA: Academic Press Inc.

Finckh et al., "Influence of anti-infliximab antibodies and residual infliximab concentrations on the occurrence of acquired drug resistance to infliximab in rheumatoid patients," Joint Bone Spine, 77:313-318, 2010.

Murtazina, N.R. et al., "Immunochemical detection of sulfamethazine in river water and medicines," Chemotherapeutic Magazine, 39(8):93-97, 2005.

Arends, S. et al., "The formation of autoantibodies and antibodies to TNF-α blocking agents in relation to clinical response in patients with ankylosing spondylitis," Clinical and Experimental Rheumatology, 28(5):661-8, 2010.

Brekke, O. et al., "Therapeutic antibodies for human diseases at the dawn of the twenty-first century," Nature Reviews Drug Discovery, 2:52-62, 2003.

Holmskov-Nielsen, U. et al., "Immune complex formation analysed by high-performance size exclusion chromatography (HPLC-SEC) using either 125I-labelled antigen or enzyme-linked immunosorbent assay (ELISA) for detection." Immunology, 51(4): 809-14, 1984.

Maier, K. et al., "Fluorescent HPLC assay for 20-HETE and other P-450 metabolites of arachidonic acid," A. J. Physiol. Heart Circ. Physiol., 279:H865-H871, 2000.

Palframan R. et al., "Use of biofluorescence imaging to compare the distribution of certolizumab pegol, adalimumab, and infliximab in the inflamed paws of mice with collagen-induced arthritis," J. Immunol. Methods., 348(1-2):36-41, 2009.

Steenholdt, C. et al. "Measurement of infliximab and anti-infliximab antibody levels can help distinguish maintenance versus loss of response," Gastroenterology & Hepatology, 8(2):131-134, 2012.

Tiittanen, M. et al., "Anti-insulin activity in IgG-fractions from children with newly-diagnosed type 1 diabetes and negative for insulin autoantibodies," Autoimmunity, 37(I): 45-9, 2004.

\* cited by examiner

|  | Bridge ELISA | | HACA Shift Assay | Mobility Shift Assay (4% Serum) | |
|---|---|---|---|---|---|
| Acession # | Quantitative Result | Qualitative Result | HACA Shift Assay | HACA Area/ Remicase-647 Area | Remicade (nM) |
| SK07010477 | 22.26 | Positive | Positive | 0.78 | 3.33 |
| SK07060083 | 1.41 | Negative | Negative | 0.1 | 4.06 |
| SK07070083 | 1.41 | Negative | Negative | 0.1 | 8.81 |
| SK07070305 | 1.41 | Negative | Positive | 0.46 | 7.34 |
| SK07070595 | 1.41 | Negative | Positive | 0.25 | 8.35 |
| SK07071213 | 2.48 | Positive | Positive | 0.16 | 5.30 |
| SK07081127 | 22.07 | Positive | Positive | 0.28 | 3.00 |
| SK07110035 | 1.41 | Negative | Positive | 0.18 | >66.7 |
| SK07141447 | 2.62 | Positive | Positive | 0.42 | 2.43 |
| SK07171059 | 10.11 | Positive | Positive | 18.02 | 2.59 |
| SK07171095 | 10.03 | Positive | Positive | 0.24 | 2.24 |
| SK07210210 | 9.26 | Positive | Positive | 0.8 | <0.67 |
| SK07231216 | 25.58 | Positive | Positive | Complete Shift | 1.34 |
| SK07310149 | 2.74 | Positive | Positive | 0.21 | <0.67 |
| SK08040168 | 22.21 | Positive | Positive | Complete Shift | <0.67 |
| SK08051035 | 9.72 | Positive | Positive | 8.7 | 1.89 |
| SK08070307 | 2.49 | Positive | Positive | 0.23 | 3.14 |
| SK08120222 | 9.2 | Positive | Positive | 0.25 | <0.67 |
| SK08260093 | 23.15 | Positive | Positive | 0.48 | 1.04 |
| SK08260783 | 2.67 | Positive | Positive | 0.25 | 3.30 |
| 62.5ng Remicade-647 | | | | 0.12 | |
| 100ng TNF-647 | | | | | <0.67 |

*FIG. 9*

| | Bridge HACA Assay | Biotin and DIG-Based Homogeneous Bridging ELISA | HACA Assay of the Present Invention |
|---|---|---|---|
| Assay Format | 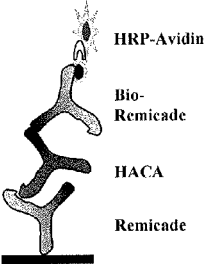 HRP-Avidin, Bio-Remicade, HACA, Remicade | 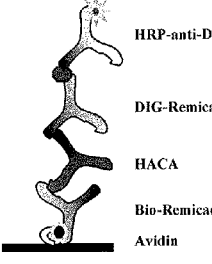 HRP-anti-DIG, DIG-Remicade, HACA, Bio-Remicade, Avidin | 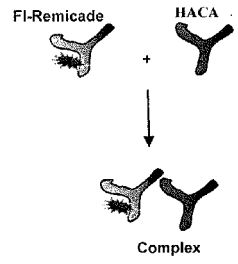 Fl-Remicade + HACA → Complex |
| Non-specific Background Interference | High | High | Low |
| Sensitivity | Low | Medium | High |
| Possibility of False-Positive and False-Negative | High | High | Low |
| IgG4 HACA Detection | No | No | Yes |
| Ig Isotype identification | No | No | Yes |
| Tolerance of Drug in the Sample | Poor | Poor | Good |

FIG. 10

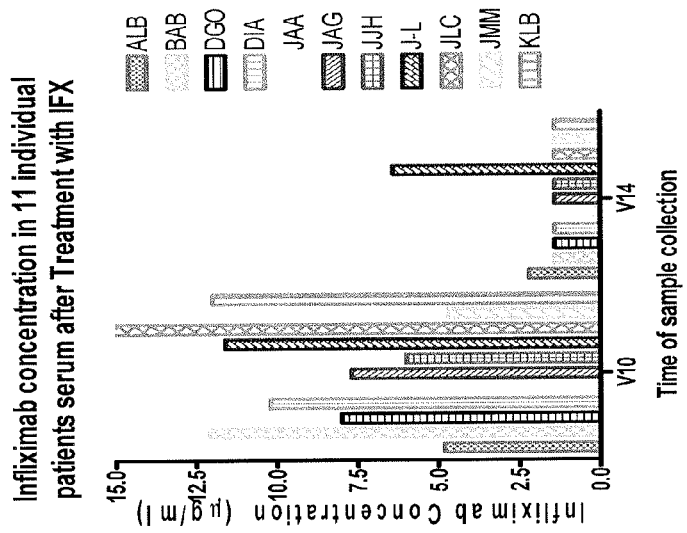
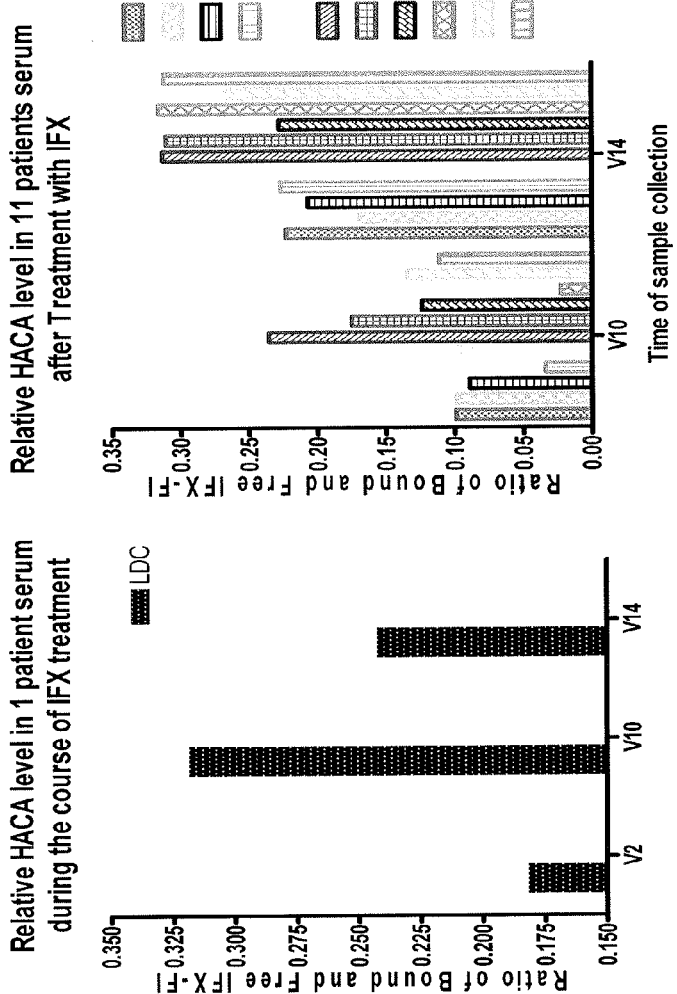
FIG. 16A
FIG. 16B
FIG. 16C

METHODS FOR DETERMINING ANTI-DRUG ANTIBODY ISOTYPES

CROSS-REFERENCE TO RELATED APPLICATION

This application is a continuation of PCT/US2011/056777, filed Oct. 18, 2011, which application claims priority to U.S. Provisional Application No. 61/394,269, filed Oct. 18, 2010, the disclosures of which are hereby incorporated by reference in their entirety for all purposes.

BACKGROUND OF THE INVENTION

Autoimmune disorders are a significant and widespread medical problem. For example, rheumatoid arthritis (RA) is an autoimmune disease affecting more than two million people in the United States. RA causes chronic inflammation of the joints and typically is a progressive illness that has the potential to cause joint destruction and functional disability. The cause of rheumatoid arthritis is unknown, although genetic predisposition, infectious agents and environmental factors have all been implicated in the etiology of the disease. In active RA, symptoms can include fatigue, lack of appetite, low grade fever, muscle and joint aches and stiffness. Also during disease flare ups, joints frequently become red, swollen, painful and tender, due to inflammation of the synovium. Furthermore, since RA is a systemic disease, inflammation can affect organs and areas of the body other than the joints, including glands of the eyes and mouth, the lung lining, the pericardium, and blood vessels.

Traditional treatments for the management of RA and other autoimmune disorders include fast acting "first line drugs" and slower acting "second line drugs." The first line drugs reduce pain and inflammation. Example of such first line drugs include aspirin, naproxen, ibuprofen etodolac and other non-steroidal anti-inflammatory drugs (NSAIDs), as well as corticosteroids, given orally or injected directly into tissues and joints. The second line drugs promote disease remission and prevent progressive joint destruction and are also referred to as disease-modifying anti-rheumatic drugs or DMARDs. Examples of second line drugs include gold, hydrochloroquine, azulfidine and immunosuppressive agents, such as methotrexate, azathioprine, cyclophosphamide, chlorambucil and cyclosporine. Many of these drugs, however, can have detrimental side-effects. Thus, additional therapies for rheumatoid arthritis and other autoimmune disorders have been sought.

Tumor necrosis factor alpha (TNFα) is a cytokine produced by numerous cell types, including monocytes and macrophages, that was originally identified based on its ability to induce the necrosis of certain mouse tumors. Subsequently, a factor termed cachectin, associated with cachexia, was shown to be identical to TNFα. TNFα has been implicated in the pathophysiology of a variety of other human diseases and disorders, including shock, sepsis, infections, autoimmune diseases, RA, Crohn's disease, transplant rejection and graft-versus-host disease.

Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity. Some of the earliest of such antibodies were mouse monoclonal antibodies (mAbs) secreted by hybridomas prepared from lymphocytes of mice immunized with hTNFα (see, e.g., U.S. Pat. No. 5,231,024). While these mouse anti-hTNFα antibodies often displayed high affinity for hTNFα and were able to neutralize hTNFα activity, their use in vivo has been limited by problems associated with the administration of mouse antibodies to humans, such as a short serum half-life, an inability to trigger certain human effector functions, and elicitation of an unwanted immune response against the mouse antibody in a human (the "human anti-mouse antibody" (HAMA) reaction).

More recently, biological therapies have been applied to the treatment of autoimmune disorders such as rheumatoid arthritis. For example, four TNFα inhibitors, REMICADE™ (infliximab), a chimeric anti-TNFα mAb, ENBREL™ (etanercept), a TNFR-Ig Fc fusion protein, HUMIRA™ (adalimumab), a human anti-TNFα mAb, and CIMZIA® (certolizumab pegol), a PEGylated Fab fragment, have been approved by the FDA for treatment of rheumatoid arthritis. CIMZIA® is also used for the treatment of moderate to severe Crohn's disease (CD). While such biologic therapies have demonstrated success in the treatment of rheumatoid arthritis and other autoimmune disorders such as CD, not all subjects treated respond, or respond well, to such therapy.

Moreover, administration of TNFα inhibitors can induce an immune response to the drug and lead to the production of anti-drug antibodies (ADA) such as human anti-chimeric antibodies (HACA), human anti-humanized antibodies (HAHA), and human anti-mouse antibodies (HAMA). Such HACA, HAHA, or HAMA immune responses can be associated with hypersensitive reactions and dramatic changes in pharmacokinetics and biodistribution of the immunotherapeutic TNFα inhibitor that preclude further treatment with the drug. In addition, the presence of particular isotypes of HACA, HAHA, or HAMA is associated with different clinical outcomes in subjects receiving anti-TNFα therapy.

Accordingly, there is a need in the art for assays to detect the presence or level of a specific ADA isotype or a particular combination of ADA isotypes in a sample. There is also a need in the art for methods to select an appropriate course of anti-TNFα therapy, to monitor anti-TNFα therapy, and/or to guide treatment decisions. The present invention satisfies these needs and provides related advantages as well.

BRIEF SUMMARY OF THE INVENTION

The present invention provides assay methods for the determination of one or more anti-drug antibody (ADA) isotypes in a sample. As a non-limiting example, the assays of the present invention are particularly useful for determining different ADA isotypes in samples from ADA-positive patients receiving an anti-TNFα drug such as REMICADE™ (infliximab) or HUMIRA™ (adalimumab). The present invention also provides methods for optimizing therapy and/or reducing toxicity in subjects receiving TNFα inhibitors for the treatment of TNFα-mediated disease or disorders.

In one aspect, the present invention provides a method for detecting the presence (or absence) or level of at least one isotype (e.g., a plurality of isotypes) of an autoantibody to an anti-TNFα drug in a sample, the method comprising:

(a) contacting a labeled anti-TNFα drug with a sample having or suspected of having at least one isotype of an autoantibody to the anti-TNFα drug to form labeled complexes between the labeled anti-TNFα drug and each autoantibody isotype;

(b) subjecting the labeled complexes to size exclusion chromatography to separate the labeled complexes having different autoantibody isotypes from each other and/or from free labeled anti-TNFα drug; and (c) detecting the labeled complexes, thereby detecting the presence (or absence) or level of at least one isotype of the autoantibody to the anti-TNFα drug.

In some embodiments, the anti-TNFα drug is selected from the group consisting of REMICADE™ (infliximab), HUMIRA™ (adalimumab), ENBREL™ (etanercept), CIMZIA® (certolizumab pegol), and combinations thereof. In other embodiments, the autoantibody to the anti-TNFα drug (e.g., anti-drug antibody or "ADA") is selected from the group consisting of a human anti-chimeric antibody (HACA), a human anti-humanized antibody (HAHA), a human anti-mouse antibody (HAMA), and combinations thereof.

In certain embodiments, the at least one isotype comprises a plurality of at least two, three, four, five, or more isotypes. In other embodiments, the at least one isotype is selected from the group consisting of IgA, IgD, IgE, IgG, and IgM isotypes, subclasses thereof; and combinations thereof. In some instances, the sample is whole blood, serum, or plasma.

In some embodiments, the autoantibody to the anti-TNFα drug is HACA and the sample is obtained from a subject on REMICADE™ (infliximab) therapy. In certain other embodiments, the autoantibody to the anti-TNFα drug is HAHA and the sample is obtained from a subject on HUMIRA™ (adalimumab) therapy.

In some instances, the labeled anti-TNFα drug is a fluorophore-labeled anti-TNFα drug. In particular embodiments, the labeled complexes are detected using fluorescence label detection. In certain embodiments, each autoantibody isotype is characterized or identified or detected by its retention time. In other embodiments, the size exclusion chromatography is size exclusion-high performance liquid chromatography (SE-HPLC).

In one related aspect, the present invention provides a method for detecting the presence (or absence) or level of at least one isotype (e.g., a plurality of isotypes) of an autoantibody to an anti-TNFα drug in a sample, the method comprising:

(a) contacting a labeled anti-TNFα drug and one or a plurality of labeled anti-Ig antibodies specific for different antibody isotypes with a sample having or suspected of having at least one isotype of an autoantibody to the anti-TNFα drug to form labeled complexes between the labeled anti-TNFα drug, the labeled anti-Ig antibodies, and each autoantibody isotype, wherein the labeled anti-TNFα drug and the labeled anti-Ig antibodies comprise different labels;

(b) subjecting the labeled complexes to size exclusion chromatography to separate the labeled complexes having different autoantibody isotypes from each other, from free labeled anti-TNFα drug, and/or from free labeled anti-Ig antibodies; and (c) detecting the labeled complexes, thereby detecting the presence (or absence) or level of at least one isotype of the autoantibody to the anti-TNFα drug.

In some embodiments, the anti-TNFα drug is selected from the group consisting of REMICADE™ (infliximab), HUMIRA™ (adalimumab), ENBREL™ (etanercept), CIMZIA® (certolizumab pegol), and combinations thereof. In other embodiments, the autoantibody to the anti-TNFα drug (e.g., anti-drug antibody or "ADA") is selected from the group consisting of a human anti-chimeric antibody (HACA), a human anti-humanized antibody (HAHA), a human anti-mouse antibody (HAMA), and combinations thereof.

In particular embodiments, the labeled anti-TNFα drug and the one or plurality of labeled anti-Ig antibodies bind to different epitopes of the at least one isotype. As one non-limiting example, the labeled anti-TNFα drug and labeled anti-Ig isotype-specific antibody bind to different epitopes of a particular autoantibody isotype.

In certain embodiments, the at least one isotype comprises a plurality of at least two, three, four, five, or more isotypes. In other embodiments, the at least one isotype is selected from the group consisting of IgA, IgD, IgE, IgG, and IgM isotypes, subclasses thereof, and combinations thereof.

In some embodiments, the plurality of labeled anti-Ig antibodies comprises at least two, three, four, five, or more labeled anti-Ig antibodies specific for different antibody isotypes. In other embodiments, the one or plurality of labeled anti-Ig antibodies is selected from the group consisting of antibodies specific for one or more of IgA, IgD, IgE, IgG, and IgM isotypes, subclasses thereof, and combinations thereof. In some instances, the sample is whole blood, serum, or plasma.

In some embodiments, the autoantibody to the anti-TNFα drug is HACA and the sample is obtained from a subject on REMICADE™ (infliximab) therapy. In certain other embodiments, the autoantibody to the anti-TNFα drug is HAHA and the sample is obtained from a subject on HUMIRA™ (adalimumab) therapy.

In some instances, the labeled anti-TNFα drug is a fluorophore-labeled anti-TNFα drug. In certain other instances, the labeled anti-Ig antibodies are fluorophore-labeled anti-Ig antibodies. The plurality of labeled anti-Ig antibodies specific for different antibody isotypes may each comprise the same label or different labels. In one non-limiting example, the plurality of labeled anti-Ig isotype-specific antibodies is each labeled with Alexa-532 and the labeled anti-TNFα drug is labeled with Alexa-488.

In some embodiments, the labeled complexes are detected using fluorescence label detection. In particular embodiments, the labeled complexes are detected upon a signal that is generated by the proximity binding of both the labeled anti-TNFα drug and the labeled anti-Ig antibodies to the autoantibody isotype. In certain instances, the signal comprises a fluorescent signal that is detected by fluorescence resonance energy transfer (FRET). In other embodiments, the size exclusion chromatography is size exclusion-high performance liquid chromatography (SE-HPLC). In certain embodiments, each autoantibody isotype is characterized or identified or detected by its retention time.

In yet another aspect, the present invention provides a method for optimizing therapy and/or reducing toxicity in a subject receiving a course of therapy for the treatment of a TNFα-mediated disease or disorder, the method comprising:

(a) analyzing a sample obtained from the subject to determine the presence, level, or genotype of one or more markers in the sample;

(b) applying a statistical algorithm to the presence, level, or genotype of the one or more markers determined in step (a); and (c) determining a subsequent dose of the course of therapy for the subject or whether a different course of therapy should be administered to the subject based upon the statistical algorithm applied in step (b).

As a non-limiting example, the presence, level, or genotype of one, two, three, four, five, or all six of the following classes of biochemical markers, serological markers, and/or genetic markers can be detected, measured, or determined in a patient sample (e.g., a serum sample from a patient on anti-TNF drug therapy):

(1) anti-TNF drug levels (e.g., levels of free anti-TNFα therapeutic antibody);
(2) anti-drug antibody (ADA) levels (e.g., level of autoantibody to the anti-TNF drug);
(3) TNFα levels;
(4) levels of one, two, three, four, five, six, seven, or more additional cytokines (e.g., IL-6, IL-1β, IFN-γ, IL-10, etc.) and/or markers for other mechanisms of inflammation (e.g., inflammatory markers such as CRP, SAA, ICAM-1, and/or VCAM-1);
(5) the presence or absence of one or more mutations in one or more genetic markers such as inflammatory pathway genes, e.g., the presence or absence of variant alleles (e.g., SNPs) in one or more inflammatory markers such as, e.g., NOD2/CARD15 (e.g., SNP 8, SNP 12, and/or SNP 13 described in U.S. Pat. No. 7,592,437), ATG16L1 (e.g., the rs2241880 (T300A) SNP described in Lakatos et al., *Digestive and Liver Disease*, 40 (2008) 867-873), IL23R (e.g., the rs11209026 (R381Q) SNP described in Lakatos et al.), the human leukocyte antigen (HLA) genes and/or cytokine genes described in, e.g., Gasche et al. (*Eur. J. Gastroenterology & Hepatology*, (2003) 15:599-606), and the DLG5 and/or OCTN genes from the IBD5 locus;
(6) levels of one or more of the above biochemical markers and/or serological markers at multiple time points (e.g., at 28 weeks, 60 weeks, etc.); and
(7) combinations thereof.

In particular embodiments, a single statistical algorithm or a combination of two or more statistical algorithms can then be applied to the presence, level (concentration level), or genotype of the one or more (e.g., a combination of two, three, four, five, six, seven, or more) markers detected, measured, or determined in the sample to thereby optimize therapy, reduce toxicity, and/or monitor the efficacy of therapeutic treatment with the anti-TNF drug. As such, the methods of the present invention find utility in determining patient management by determining patient immune status.

Methods for detecting anti-TNF drugs (e.g., anti-TNFα antibodies) and anti-drug antibodies (ADA) such as HACA and HAHA are further described in PCT Publication No. WO 2011/056590, the disclosure of which is hereby incorporated by reference in its entirety for all purposes.

Other objects, features, and advantages of the present invention will be apparent to one of skill in the art from the following detailed description and figures.

BRIEF DESCRIPTION OF THE DRAWINGS

FIG. 9 provides a summary of HACA measurements from 20 patient serum samples that were performed using the bridging assay or the mobility shift assay of the present invention.

FIG. 10 provides a summary and comparison of current methods for measuring serum concentrations of HACA to the novel HACA assay of the present invention.

FIGS. 16A-16C show patient management-measurement of HACA level and IFX concentration in the sera of IBD patients treated with IFX at different time points.

DETAILED DESCRIPTION OF THE INVENTION

I. Introduction

Figure 1:
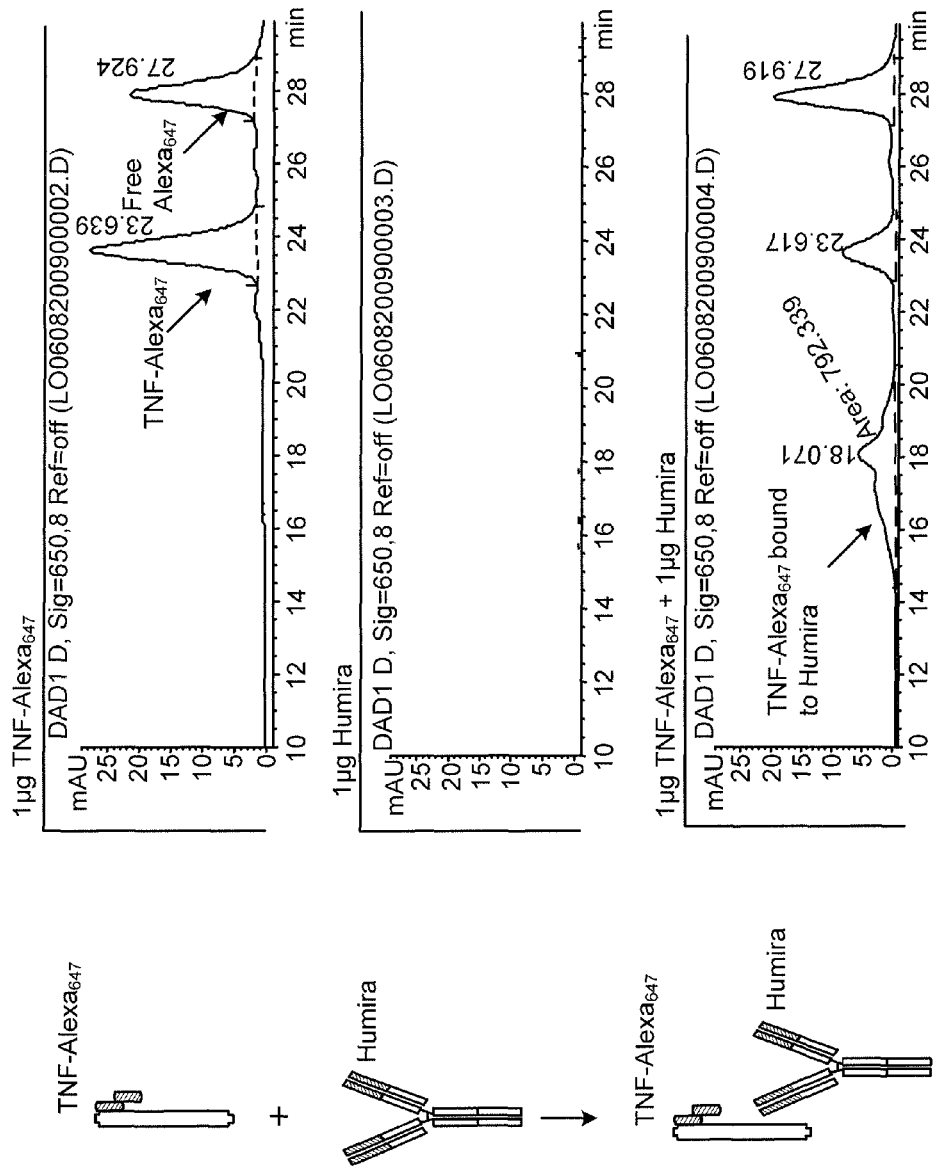
FIG. 1 shows an exemplary embodiment of the assays of the present invention wherein size exclusion HPLC is used to detect the binding between TNFα-Alexa$_{647}$ and HUMIRA™.

TNFα has been implicated in inflammatory diseases, autoimmune diseases, viral, bacterial and parasitic infections, malignancies, and/or neurodegenerative diseases and is a useful target for specific biological therapy in diseases such as rheumatoid arthritis (RA) and Crohn's disease (CD). TNFα inhibitors such as anti-TNFα antibodies are an important class of therapeutics. However, administration of TNFα inhibitors can induce an immune response to the drug and lead to the production of anti-drug antibodies (ADA), thereby precluding further treatment with the drug. In addition, the presence of particular ADA isotypes can be associated with different clinical outcomes in subjects receiving anti-TNFα therapy.

The present invention is based in part on the discovery that a homogeneous mobility shift assay using size exclusion chromatography is particularly advantageous for measuring the presence or level of one or more ADA isotypes in a sample. As a non-limiting example, the assays of the present invention are particularly useful for determining different ADA isotypes in samples from ADA-positive patients receiving an anti-TNFα drug such as REMICADE™ (infliximab) or HUMIRA™ (adalimumab).

In particular, the present invention provides "mix and read" ADA isotyping assays that do not require any wash steps. As a result, complexed and uncomplexed reagents are easily separated from each other. In addition, any potential interference from the free anti-TNFα drug is minimized using the assays of the present invention. In contrast, a typical ELISA for measuring autoantibody levels cannot be performed until the TNFα inhibitor is eliminated from the body, which can take up to 3 months. Moreover, the present invention is generally applicable to a wide variety of anti-TNFα therapeutics in addition to anti-TNFα antibodies. The assays of the present invention are also advantageous because they avoid the attachment of antigens to solid surfaces, eliminate the non-specific binding of irrelevant IgGs, detect antibodies with weak affinities, and exhibit increased sensitivity and specificity over currently available detection methods such as enzyme immunoassays.

The importance of measuring serum concentrations of anti-TNFα biologics (e.g., anti-TNFα antibodies) as well autoantibodies generated against them (e.g., ADA isotypes) is illustrated by the fact that the FDA requires pharmacokinetic and tolerability (e.g., immune response) studies to be performed during clinical trials. The present invention also finds utility in monitoring patients receiving these drugs to make sure they are getting the right dose, that the drug isn't being cleared from the body too quickly, and that they are not developing an immune response against the drug. Furthermore, the present invention is useful in guiding the switch between different drugs due to failure with the initial drug.

The present invention also provides methods for optimizing therapy and/or reducing toxicity in subjects receiving TNFα inhibitors for the treatment of TNFα-mediated diseases or disorders. Moreover, the present invention is particularly advantageous because it addresses and overcomes current limitations associated with the administration of anti-TNF drugs such as infliximab or adalimumab, in part, by providing information useful for guiding treatment decisions for those patients receiving or about to receive anti-TNF drug therapy.

II. Definitions

As used herein, the following terms have the meanings ascribed to them unless specified otherwise.

The term "TNFα" as used herein is intended to include a human cytokine that exists as a 17 kDa secreted form and a 26 kDa membrane associated form, the biologically active form of which is composed of a trimer of noncovalently bound 17 kDa molecules. The structure of TNFα is described further in, for example, Jones et al. (1989) *Nature*, 338:225-228. The term TNFα is intended to include human TNFα, a recombinant human TNFα (rhTNFα), or a polypeptide having at least about 80% identity to the human TNFα protein. Human TNFα consists of a 35 amino acid (aa) cytoplasmic domain, a 21 aa transmembrane segment, and a 177 aa extracellular domain (ECD) (Pennica et al. (1984) *Nature* 312:724). Within the ECD, human TNFα shares 97% aa sequence identity with rhesus and 71% to 92% with bovine, canine, cotton rat, equine, feline, mouse, porcine, and rat TNFα. TNFα can be prepared by standard recombinant expression methods or purchased commercially (e.g., R & D Systems, Catalog No. 210-TA, Minneapolis, Minn.).

The term "TNFα inhibitor" or "TNFα drug" is intended to encompass agents including proteins, antibodies, antibody fragments, fusion proteins (e.g., Ig fusion proteins or Fc fusion proteins), multivalent binding proteins (e.g., DVD Ig), small molecule TNFα antagonists and similar naturally- or normatively-occurring molecules, and/or recombinant and/or engineered forms thereof, that, directly or indirectly, inhibits TNFα activity, such as by inhibiting interaction of TNFα with a cell surface receptor for TNFα, inhibiting TNFα protein production, inhibiting TNFα gene expression, inhibiting TNFα secretion from cells, inhibiting TNFα receptor signaling or any other means resulting in decreased TNFα activity in a subject. The term "TNFα inhibitor" or "TNFα drug" preferably includes agents which interfere with TNFα activity. Examples of TNFα drugs include etanercept (ENBREL™, Amgen), infliximab (REMICADE™, Johnson and Johnson), human anti-TNF monoclonal antibody adalimumab (D2E7/HUMIRA™, Abbott Laboratories), CDP 571 (Celltech), and CDP 870 (Celltech), as well as other compounds which inhibit TNFα activity, such that when administered to a subject suffering from or at risk of suffering from a disorder in which TNFα activity is detrimental (e.g., RA), the disorder is treated.

The term "immunoglobulin isotype" or "antibody isotype" includes any member of a family of related antibodies comprising genetic variations and/or differences in the constant regions of the heavy and/or light chains. Non-limiting examples of antibody isotypes include (1) heavy chain isotypes such as a (e.g., IgA or a subclass thereof such as IgA1 and/or IgA2); δ (e.g., IgD); γ (e.g., IgG or a subclass thereof such as IgG1, IgG2, IgG3, and/or IgG4); ε (e.g., IgE); μ (e.g., IgM); and (2) light chain isotypes such as κ and λ.

The term "size exclusion chromatography" (SEC) is intended to include a chromatographic method in which molecules in solution are separated based on their size and/or hydrodynamic volume. It is applied to large molecules or macromolecular complexes such as proteins and their conjugates. Typically, when an aqueous solution is used to transport the sample through the column, the technique is known as gel filtration chromatography.

The terms "complex," "immuno-complex," "conjugate," and "immunoconjugate" include, but are not limited to, TNFα bound (e.g., by non-covalent means) to an anti-TNFα drug, an anti-TNFα drug bound (e.g., by non-covalent means) to an autoantibody against the anti-TNFα drug, an anti-TNFα drug bound (e.g., by non-covalent means) to both TNFα and an autoantibody against the anti-TNFα drug, an anti-TNFα drug bound (e.g., by non-covalent means) to an isotype of an autoantibody against the anti-TNFα drug, and an anti-TNFα drug and an anti-Ig isotype-specific antibody bound (e.g., by non-covalent means) to an isotype of an autoantibody against the anti-TNFα drug.

As used herein, an entity that is modified by the term "labeled" includes any entity, molecule, protein, enzyme, antibody, antibody fragment, cytokine, or related species that is conjugated with another molecule or chemical entity that is empirically detectable. Chemical species suitable as labels for labeled-entities include, but are not limited to, fluorescent dyes (e.g. Alexa Fluor® dyes such as Alexa Fluor® 488, 532, or 647); quantum dots; optical dyes; luminescent dyes; and radionuclides, e.g. $^{125}$I.

The phrase "fluorescence label detection" includes a means for detecting a fluorescent label. Means for detection include, but are not limited to, a spectrometer, a fluorimeter, a photometer, a detection device commonly incorporated with a chromatography instrument such as, but not limited to, a size exclusion-high performance liquid chromatography, such as, but not limited to, an Agilent-1200 HPLC System.

The term "optimizing therapy" or "optimize therapy" includes optimizing the dose (e.g., the effective amount or level) and/or the type of a particular therapy. For example, optimizing the dose of an anti-TNFα drug includes increasing or decreasing the amount of the anti-TNFα drug subsequently administered to a subject. In certain instances, optimizing the type of an anti-TNFα drug includes changing the administered anti-TNFα drug from one drug to a different drug (e.g., a different anti-TNFα drug). In certain other instances, optimizing therapy may include co-administering a dose of an anti-TNFα drug (e.g., at an increased, decreased, or same dose as the previous dose) in combination with an immunosuppressive drug.

The term "course of therapy" includes any therapeutic approach taken to relieve or prevent one or more symptoms associated with a TNFα-mediated disease or disorder. The term encompasses administering any compound, drug, procedure, and/or regimen useful for improving the health of an individual with a TNFα-mediated disease or disorder and includes any of the therapeutic agents described herein. One skilled in the art will appreciate that either the course of therapy or the dose of the current course of therapy can be changed (e.g., increased or decreased) based upon the presence or concentration level of TNFα, anti-TNFα drug, and/or anti-drug antibody using the methods of the present invention.

The term "immunosuppressive agent" includes any substance capable of producing an immunosuppressive effect, e.g., the prevention or diminution of the immune response, as by irradiation or by administration of drugs such as anti-metabolites, anti-lymphocyte sera, antibodies, etc. Examples of suitable immunosuppressive agents include, without limitation, thiopurine drugs such as azathioprine (AZA) and metabolites thereof; anti-metabolites such as methotrexate (MTX); sirolimus (rapamycin); temsirolimus; everolimus; tacrolimus (FK-506); FK-778; anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; metabolites thereof; pharmaceutically acceptable salts thereof; derivatives thereof; prodrugs thereof; and combinations thereof.

The term "thiopurine drug" includes azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof; analogues thereof, and combinations thereof.

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. One skilled in the art will appreciate that samples such as serum samples can be diluted prior to the analysis. In certain instances, the term "sample" includes, but is not limited to blood, body tissue, blood serum, lymph fluid, lymph node tissue, spleen tissue, bone marrow, or an immunoglobulin enriched fraction derived from one or more of these tissues. In certain other instances, the term "sample" includes blood serum or is an immunoglobulin enriched fraction derived from blood serum or blood. In certain instances, the term "sample" includes a bodily fluid.

The term "predicting responsiveness to a TNFα inhibitor" is intended to refer to an ability to assess the likelihood that treatment of a subject with a TNFα inhibitor will or will not be effective in (e.g., provide a measurable benefit to) the subject. In particular, such an ability to assess the likelihood that treatment will or will not be effective typically is exercised after treatment has begun, and an indicator of effectiveness (e.g., an indicator of measurable benefit) has been observed in the subject. Particularly preferred TNFα inhibitors are biologic agents that have been approved by the FDA for use in humans in the treatment of rheumatoid arthritis (RA), which agents are described herein and include, but are not limited to, adalimumab (HUMIRA™), infliximab (REMICADE™) and etanercept (ENBREL™)

The term "subject," "patient," or "individual" typically refers to humans, but also to other animals including, e.g., other primates, rodents, canines, felines, equines, ovines, porcines, and the like.

III. Description of the Embodiments

The present invention provides assay methods for the determination of one or more anti-drug antibody (ADA) isotypes in a sample. As a non-limiting example, the assays of the present invention are particularly useful for determining different ADA isotypes in samples from ADA-positive patients receiving an anti-TNFα drug such as REMI-CADE™ (infliximab) or HUMIRA™ (adalimumab). The present invention also provides methods for optimizing therapy and/or reducing toxicity in subjects receiving TNFα inhibitors for the treatment of TNFα-mediated disease or disorders.

In one aspect, the present invention provides a method for detecting the presence (or absence) or level of at least one isotype (e.g., a plurality of isotypes) of an autoantibody to an anti-TNFα drug in a sample, the method comprising:
- (a) contacting a labeled anti-TNFα drug (e.g., labeled anti-TNFα antibody) with a sample having or suspected of having at least one isotype of an autoantibody to the anti-TNFα drug (e.g., IgA, IgD, IgE, IgG, and/or IgM) to form labeled complexes (i.e., immuno-complexes or conjugates) between the labeled anti-TNFα drug and each autoantibody isotype (i.e., wherein the labeled anti-TNFα drug and autoantibody isotype are not covalently attached to each other);
- (b) subjecting the labeled complexes to size exclusion chromatography to separate the labeled complexes having different autoantibody isotypes from each other and/or from free labeled anti-TNFα drug; and
- (c) detecting the labeled complexes, thereby detecting the presence (or absence) or level of at least one isotype of the autoantibody to the anti-TNFα drug.

In one related aspect, the present invention provides a method for detecting the presence (or absence) or level of at least one isotype (e.g., a plurality of isotypes) of an autoantibody to an anti-TNFα drug in a sample, the method comprising:
- (a) contacting a labeled anti-TNFα drug (e.g., labeled anti-TNFα antibody) and one or a plurality of labeled anti-Ig antibodies specific for different antibody isotypes (e.g., IgA, IgD, IgE, IgG, and/or IgM isotypes) with a sample having or suspected of having at least one isotype of an autoantibody to the anti-TNFα drug to form labeled complexes (i.e., immuno-complexes or conjugates) between the labeled anti-TNFα drug, the labeled anti-Ig antibodies, and each autoantibody isotype (i.e., wherein the components of the labeled complexes are not covalently attached to each other), wherein the labeled anti-TNFα drug and the labeled anti-Ig antibodies comprise different labels;
- (b) subjecting the labeled complexes to size exclusion chromatography to separate the labeled complexes having different autoantibody isotypes from each other, from free labeled anti-TNFα drug, and/or from free labeled anti-Ig antibodies; and
- (c) detecting the labeled complexes, thereby detecting the presence (or absence) or level of at least one isotype of the autoantibody to the anti-TNFα drug.

In some embodiments, the anti-TNFα drug is selected from the group consisting of REMICADE™ (infliximab), HUMIRA™ (adalimumab), ENBREL™ (etanercept), CIM-ZIA® (certolizumab pegol), and combinations thereof.

In certain embodiments, the methods are useful for measuring the (concentration) levels of at least one, two, three, four, five, or more antibody isotypes in a sample such as a whole blood, serum, or plasma sample from a subject receiving anti-TNFα drug therapy. In some instances, the methods are useful for determining different anti-drug antibody (ADA) isotypes such as different isotypes of ATI (i.e., antibody to IFX; "HACA") in ADA-positive patients receiving anti-TNFα drug therapy such as infliximab (IFX). In other instances, the methods are useful for determining different ADA isotypes such as different isotypes of ATA (i.e., antibody to adalimumab; "HAHA") in ADA-positive patients receiving anti-TNFα drug therapy such as adalimumab. Non-limiting examples of antibody isotypes include IgA, IgD, IgE, IgG, and IgM. In particular embodiments, the methods of the invention aid or assist in associating different clinical outcomes in patients receiving anti-TNFα drug therapy based upon the presence or level of a specific ADA isotype or a particular combination of ADA isotypes.

An anti-TNFα drug or an anti-Ig antibody specific for an antibody isotype can be labeled with a variety of detectable group(s). In particular embodiments, the anti-TNFα drug and/or the anti-Ig isotype-specific antibody is labeled with a fluorophore or a fluorescent dye. Non-limiting examples of fluorophores suitable for use as labels that can be attached to the anti-TNFα drugs and anti-Ig isotype-specific antibodies described herein include those listed in the Molecular Probes Catalogue, which is herein incorporated by reference in its entirety for all purposes (see, R. Haugland, *The Handbook-A Guide to Fluorescent Probes and Labeling Technologies*, 10$^{th}$ Edition, Molecular probes, Inc. (2005)). Such exemplary fluorophores include, but are not limited to, Alexa Fluor® dyes such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790, as well as other fluorophores including, without limitation, Dansyl Chloride (DNS-Cl), 5-(iodoacetamida)fluoroscein (5-IAF), fluoroscein 5-isothiocyanate (FITC), tetramethylrhodamine 5-(and 6-)isothiocyanate (TRITC), 6-acryloyl-2-dimethyl-aminonaphthalene(acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids (e.g., 1-anilinonaphthalene-8-sulfonic acid (ANS), 6-(p-toluidinyl) naphthalen-e-2-sulfonic acid (TNS), and the like), Anthroyl fatty acid, DPH, Parinaric acid, TMA-DPH, Fluorenyl fatty acid, fluorescein-phosphatidylethanolamine, Texas Red-phosphatidylethanolamine, Pyrenyl-phophatidylcholine, Fluorenyl-phosphotidylcholine, Merocyanine 540,1-(3-sulfonatopropyl)-4-[β-[2[(di-n-butylamino)-6 naphthyl]vinyl] pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, IRDye° 700DX, IRDye® 700, IRDye® 800RS, IRDye® 800CW, IRDye® 800, Cy5, Cy5.5, Cy7, DY 676, DY680, DY682, DY780, and mixtures thereof. Additional suitable fluorophores include enzyme-cofactors; lanthanide, green fluorescent protein, yellow fluorescent protein, red fluorescent protein, or mutants and derivates thereof. In one non-limiting example, the plurality of anti-Ig isotype-specific antibodies is each labeled with Alexa-532 and the anti-TNFα drug is labeled with Alexa-488.

Typically, the fluorescent group is a fluorophore selected from the category of dyes comprising polymethines, pthalocyanines, cyanines, xanthenes, fluorenes, rhodamines, coumarins, fluoresceins, and BODIPY™.

In one embodiment, the fluorescent group is a near-infrared (NIR) fluorophore that emits in the range of between about 650 to about 900 nm. Use of near infrared fluorescence technology is advantageous in biological assays as it substantially eliminates or reduces background from auto-fluorescence of biosubstrates. Another benefit to the near-IR fluorescent technology is that the scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components. Within aspects of this embodiment, the near-infrared (NIR) fluorophore is preferably selected form the group consisting of IRDye® 700DX, IRDye® 700, IRDye® 800RS, IRDye® 800CW, IRDye® 800, Alexa Fluor® 660, Alexa Fluor® 680, Alexa Fluor® 700, Alexa Fluor® 750, Alexa Fluor® 790, Cy5, Cy5.5, Cy7, DY 676, DY680, DY682 and DY780. In certain embodiments, the near infrared group is IRDye® 800CW, IRDye® 800, IRDye® 700DX, IRDye® 700, or Dynomic DY676.

Fluorescent labeling is accomplished using a chemically reactive derivative of a fluorophore. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide, many of which are commercially available. Reaction of any of these reactive dyes with an anti-TNFα drug or an anti-Ig isotype-specific antibody results in a stable covalent bond formed between a fluorophore and the anti-TNFα drug or the anti-Ig isotype-specific antibody.

In certain instances, following a fluorescent labeling reaction, it is often necessary to remove any nonreacted fluorophore from the labeled target molecule. This is often accomplished by size exclusion chromatography, taking advantage of the size difference between fluorophore and labeled protein.

Reactive fluorescent dyes are available from many sources. They can be obtained with different reactive groups for attachment to various functional groups within the target molecule. They are also available in labeling kits that contain all the components to carry out a labeling reaction. In one particular embodiment, Alexa Fluor® 647 C2 maleimide is used from Invitrogen (Cat. No. A-20347).

Specific immunological binding of an anti-TNFα drug to an autoantibody isotype or of an anti-TNFα drug and an anti-Ig antibody to an autoantibody isotype can be detected directly or indirectly. Direct labels include fluorescent or luminescent tags, metals, dyes, radionuclides, and the like, attached to the antibody. In certain instances, an anti-TNFα drug or an anti-Ig antibody labeled with iodine-125 ($^{125}$I) can be used for determining the presence or concentration levels of one or a plurality of ADA isotypes in a sample. In other instances, a chemiluminescence assay using a chemiluminescent anti-TNFα drug or anti-Ig antibody is suitable for sensitive, non-radioactive detection of ADA isotypes in a sample. In particular instances, an anti-TNFα drug and/or an anti-Ig antibody labeled with a fluorochrome is also suitable for determining the concentration levels of one or a plurality of ADA isotypes in a sample. Examples of fluorochromes include, without limitation, Alexa Fluor® dyes, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially. As a non-limiting example, goat F(ab')$_2$ anti-human IgG-FITC is available from Tago Immunologicals (Burlingame, CA).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of one or a plurality of ADA isotypes can be made using a spectrophotometer such as an EMAX Microplate Reader (Molecular Devices; Menlo Park, CA) in accordance with the manufacturer's instructions. If desired, the assays of the present invention can be automated or performed robotically, and the signal from multiple samples can be detected simultaneously.

In particular embodiments, size exclusion chromatography (SEC) is used in the assays of the invention. The underlying principle of SEC is that particles of different sizes will elute (filter) through a stationary phase at different rates. This results in the separation of a solution of particles based on size. Provided that all the particles are loaded simultaneously or near simultaneously, particles of the same size elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

In certain embodiments, the eluent is collected in constant volumes, or fractions. The more similar the particles are in size, the more likely they will be in the same fraction and not detected separately. In preferred embodiments, the collected fractions are examined by spectroscopic techniques to determine the concentration of the particles eluted. Typically, the spectroscopy detection techniques useful in the present invention include, but are not limited to, fluorometry, refractive index (RI), and ultraviolet (UV). In certain instances, the elution volume decreases roughly linearly with the logarithm of the molecular hydrodynamic volume (i.e., heaver moieties come off first).

In some instances, the (concentration) level of the ADA isotype present in a sample such as a serum sample can be compared to a standard curve and/or one or more controls. In certain instances, a labeled anti-TNFα drug can be incubated with known amounts of an anti-Ig isotype-specific antibody in a liquid phase reaction to create a standard curve.

In certain instances, the autoantibody isotyping methods of the present invention are proximity-based such that they rely upon a signal that is generated by the proximity binding of both the labeled anti-TNFα drug and the labeled anti-Ig isotype-specific antibody to the autoantibody isotype. In particular embodiments, the signal generated by the proximity assay is a fluorescent signal that can be detected by fluorescence resonance energy transfer (FRET). In other embodiments, the signal is detected by another proximity-based method as described herein or known to one of skill in the art.

In some instances, the plurality of labeled anti-Ig antibodies specific for different antibody isotypes each comprise the same label. In other instances, the plurality of labeled anti-Ig antibodies specific for different antibody isotypes each comprise different labels. A skilled person in the art will appreciate that anti-Ig antibodies that bind to specific classes or subclasses of antibodies (e.g., IgA, IgD, IgE, IgG, or IgM isotypes, or Ig subclasses thereof such as IgG1, IgG2, IgG3, and/or IgG4) are commercially available from vendors such as, for example, Miltenyi Biotec GmbH, Jackson ImmunoResearch Laboratories, Inc., Santa Cruz Biotechnology, Inc., Abcam plc, and others. In certain instances, the anti-Ig antibody detects a specific Ig subclass (e.g., IgG1, IgG2, IgG3, or IgG4). In certain other instances, the anti-Ig antibody detects all Ig subclasses (e.g., IgG1, IgG2, IgG3, and IgG4). For example, anti-IgA antibodies (e.g., from clone IS11-8E10, which detects both subclasses of human IgA), anti IgG antibodies (e.g., from clone IS11-3B2.2.3, which detects all subclasses of the human IgG isotype), and anti-IgM antibodies (e.g., from clone PJ2-22H3, which detects the IgM isotype) can be obtained from Miltenyi Biotec GmbH and labeled by attaching a detectable label such as a fluorophore thereto using methods described herein and known to one of skill in the art. In some instances, Molecular Probes kits from Life Technologies such as the Alexa Fluor Protein Labeling Kits and the Alexa Fluor Monoclonal Labeling Kits, which include amine-reactive Alexa Fluor dyes (e.g., Alexa Fluor succinimidyl (NHS) esters and/or Alexa Fluor tetrafluorophenyl (TFP) esters), can be used to selectively link Alexa Fluor dyes to accessible primary amine groups on antibodies.

The term "proximity" as used herein includes reference to the spatial nearness or closeness of an anti-TNFα drug to an anti-Ig isotype-specific antibody when both are bound to the same autoantibody isotype (i.e., an anti-drug antibody isotype such as IgA ATI). In particular embodiments, the binding of an anti-TNFα drug to an autoantibody isotype at a distance near or close to the binding of an anti-Ig isotype-specific antibody to the same autoantibody isotype is sufficient to generate a detectable signal. In some embodiments, the term "proximity" includes those distances between the labeled antibodies, when bound to the same autoantibody isotype, that are sufficient to generate a detectable signal. In certain other embodiments, the term "proximity" includes those distances between the detectable labels (e.g., fluorescent labels) attached to the antibodies bound to the same autoantibody isotype that are sufficient to generate a detectable signal.

FRET describes an energy transfer mechanism between two fluorescent molecules. When a fluorescent donor is excited at its specific fluorescence excitation wavelength, this excited state is nonradiatively transferred to a second molecule, the acceptor, by a long-range dipole-dipole coupling mechanism. The donor then returns to the electronic ground state. See, e.g., Lakowicz, Principles of Fluorescence Spectroscopy, Plenum Publishing Corp., 2nd Ed. (1999). In the context of the invention, the anti-TNFα drug (e.g., IFX) can be labeled with a donor comprising a first fluorescent dye and the anti-Ig isotype-specific antibody (e.g., anti-IgA, anti-IgG) can be labeled with an acceptor comprising a second fluorescent dye that has a different excitation and emission spectra from the first fluorescent dye. Non-limiting examples of fluorescent dyes suitable for use as detectable labels are described above and include fluorophores such as Alexa Fluor® dyes (e.g., Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® Fluor 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790) and other fluorophores such as, for example, fluorescein, FITC, rhodamine, Texas Red, TRITC, Cy3, Cy5, Cy5.5, Cy7, derivatives thereof, and combinations thereof.

In some embodiments, a sample such as a serum sample that is to be interrogated for the presence (or absence) or level of the autoantibody isotype (i.e., the isotype of the autoantibody to the anti-TNFα drug) is incubated with both the labeled anti-TNFα drug and the labeled anti-Ig isotype-specific antibody. If the autoantibody isotype (e.g., IgA ADA) that is detected by the particular anti-Ig isotype-specific antibody (e.g., anti-IgA) is not present in the sample, the donor emission is detected upon donor excitation. On the other hand, if the autoantibody isotype (e.g., IgA ADA) that is detected by the particular anti-Ig isotype-specific antibody (e.g., anti-IgA) is present in the sample, the donor and acceptor fluorophores are brought into proximity (e.g., from about 1 to about 300 nm or from about 1 to about 200 nm of each other, such as, for example, about 1, 5, 10, 25, 50, 75, 100, 125, 150, 175, 200, 225, 250, 275, 300 nm or any range thereof, or from about 1 to about 10 nm, e.g., about 1, 2, 3, 4, 5, 6, 7, 8, 9, or 10 nm or any range thereof) due to the interaction of both the labeled anti-TNFα drug and the particular labeled anti-Ig isotype-specific antibody with the autoantibody isotype (e.g., IgA ATI). The intermolecular FRET from the donor fluorophore to the acceptor fluorophore results in the acceptor emission being predominantly observed. For example, excitation at 480 nm for Alexa-488 as the donor fluorophore on the anti-TNFα drug induces formation of singlet oxygen molecules that react with thioxene derivatives, generating chemiluminescence, which in turn excites the acceptor fluorophore Alexa-532 on the anti-Ig isotype-specific antibody to emit at 575 nm.

Example 29 describes an exemplary proximity-based isotyping assay of the present invention for determining the presence (or absence) or level of at least one, two, three, four, five, or more ATI isotypes such as, e.g., IgA ATI, IgD ATI, IgE ATI, IgG ATI, and/or IgM ATI isotypes using FRET. As a non-limiting example, IFX labeled with a first fluorophore ("F1") and an anti-IgA antibody labeled with a second fluorophore ("F2") are incubated with a sample such as a serum sample containing one or more ATI isotypes such as IgA ATI. In some embodiments, F2 is excited by F1 only when both fluorophores are in close proximity, and the presence and/or level of a ternary complex of F1-IFX, F2-anti-IgA, and IgA ATI is indicative of the presence and/or level of the IgA ATI isotype that is present in the sample.

In other embodiments, the signal that is generated by the autoantibody isotyping proximity assay is a fluorescent signal that can be detected using an electrophoretic technique such as capillary electrophoresis (CE). CE analysis generally occurs inside a small-diameter quartz capillary in the presence of high (kilovolt-level) separating voltages with separation times of a few minutes. In the context of the present invention, the anti-TNFα drug (e.g., IFX) can be labeled with a photoactivatable enzymatic scissor and the anti-Ig isotype-specific antibody (e.g., anti-IgA, anti-IgD, anti-IgE, anti-IgG, and/or anti-IgM) can be labeled with an electrophoretic tag reporter. Non-limiting examples of photoactivatable enzymatic scissors and electrophoretic tag reporters such as the eTag™ family of small fluorescent reporter molecules are described in U.S. Pat. No. 6,673,550. The binding of the labeled anti-TNFα drug to the autoantibody isotype (e.g., IgA ATI) in proximity (e.g., from about 1 to about 300 nm or from about 1 to about 200 nm of each other, such as, for example, about 1, 5, 10, 25, 50, 75, 100, 125, 150, 175, 200, 225, 250, 275, 300 nm or any range thereof, or from about 1 to about 10 nm, e.g., about 1, 2, 3, 4, 5, 6, 7, 8, 9, or 10 nm or any range thereof) of the binding of the labeled anti-Ig isotype-specific antibody to the same autoantibody isotype triggers the cleavage of the electrophoretic tag reporter by the photoactivatable enzymatic scissor. Following photoactive cleavage, released electrophoretic tag reporter molecules are analyzed by CE separation as described in, e.g., Chan-Hui et al., Clin. Immun., 111:162-174 (2004). Alternatively, the anti-TNFα drug can be labeled with an electrophoretic tag reporter and the anti-Ig isotype-specific antibody can be labeled with a photoactivatable enzymatic scissor. In some embodiments, a plurality of electrophoretic tag reporters can be attached to a plurality of distinct anti-Ig isotype-specific antibodies and used in a multiplex assay to determine the presence (or absence) or level of multiple autoantibody isotypes of interest.

In yet other embodiments, the signal that is generated by the autoantibody isotyping proximity assay is a DNA amplification signal that can be detected using a nucleic acid amplification technique such as the polymerase chain reaction (PCR). The use of PCR for the amplification of nucleic acids is well known in the art and is described in, e.g., Mullis et al., The Polymerase Chain Reaction, Birkhäuser, Boston (1994); and Innis et al., PCR Applications: Protocols for Functional Genomics, 1st Ed., Academic Press (1999). In the context of the present invention, the anti-TNFα drug (e.g., IFX) can be labeled with a first oligonucleotide extension and the anti-Ig isotype-specific antibody (e.g., anti-IgA, anti-IgD, anti-IgE, anti-IgG, and/or anti-IgM) can be labeled with a second oligonucleotide extension. If the autoantibody isotype (e.g., IgA ATI) that is detected by the particular anti-Ig isotype-specific antibody (e.g., anti-IgA) is not present in the sample, a connector oligonucleotide independently hybridizes to each oligonucleotide extension, which does not promote their ligation. On the other hand, if the autoantibody isotype (e.g., IgA ATI) that is detected by the particular anti-Ig isotype-specific antibody (e.g., anti-IgA) is present in the sample, the binding of the labeled anti-TNFα drug to the autoantibody isotype (e.g., IgA ATI) in proximity (e.g., from about 1 to about 300 nm or from about 1 to about 200 nm of each other, such as, for example, about 1, 5, 10, 25, 50, 75, 100, 125, 150, 175, 200, 225, 250, 275, 300 nm or any range thereof, or from about 1 to about 10 nm, e.g., about 1, 2, 3, 4, 5, 6, 7, 8, 9, or 10 nm or any range thereof) of the binding of the labeled anti-Ig isotype-specific antibody to the same autoantibody isotype enables the connector oligonucleotide to simultaneously hybridize to both oligonucleotide extensions, thereby triggering the ligation of the oligonucleotide extensions by DNA ligase. One of skill in the art will appreciate that the proximity of the anti-TNFα drug to the anti-Ig isotype-specific antibody may vary depending on the length of the oligonucleotide extension. Thus, a new species of DNA sequence is created, not previously present in the reaction, which can be amplified using standard DNA amplification techniques such as PCR. The oligonucleotide extensions and connector oligonucleotides are typically chemically synthesized by any method known in the art and independently comprise a nucleotide sequence of at least about 10, 15, 20, 25, 30, 35, 40, 45, 50, 55, or 60 nucleotides in length.

In further embodiments, the signal that is generated by the autoantibody isotyping proximity assay is a chemiluminescent or fluorescent signal that can be detected using signal amplification such as tyramide signal amplification. In the context of the present invention, the anti-TNFα drug (e.g., IFX) can be labeled with glucose oxidase (GO) or any other enzyme that catalyzes an oxidation/reduction reaction involving molecular oxygen ($O_2$) as the electron acceptor. The anti-Ig isotype-specific antibody (e.g., anti-IgA, anti-IgD, anti-IgE, anti-IgG, and/or anti-IgM) can be labeled with a peroxidase such as horseradish peroxidase (HRP), e.g., directly or indirectly via binding pair members such as biotin/streptavidin. Other examples of peroxidases include, but are not limited to, catalase, chloroperoxidase, cytochrome c peroxidase, eosinophil peroxidase, glutathione peroxidase, lactoperoxidase, myeloperoxidase, thyroid peroxidase, deiodinase, and the like. When the GO is contacted with a substrate such as glucose, it generates an oxidizing agent (i.e., hydrogen peroxide ($H_2O_2$)). If the autoantibody isotype (e.g., IgA ATI) that is detected by the particular anti-Ig isotype-specific antibody (e.g., anti-IgA) is present in the sample, the binding of the labeled anti-TNFα drug to the autoantibody isotype (e.g., IgA ATI) in proximity (e.g., from about 1 to about 300 nm or from about 1 to about 200 nm of each other, such as, for example, about 1, 5, 10, 25, 50, 75, 100, 125, 150, 175, 200, 225, 250, 275, 300 nm or any range thereof, or from about 1 to about 10 nm, e.g., about 1, 2, 3, 4, 5, 6, 7, 8, 9, or 10 nm or any range thereof) of the binding of the labeled anti-Ig isotype-specific antibody to the same autoantibody isotype enables the $H_2O_2$ generated by the GO to channel to and complex with the HRP to form an $HRP-H_2O_2$ complex, which, in the presence of a chemiluminescent substrate (e.g., luminol, isoluminol) or a fluorogenic substrate (e.g., tyramide, biotin-tyramide, homovanillic acid, 4-hydroxyphenyl acetic acid), generates an amplified signal.

Methods of using GO and HRP in a proximity assay are described in, e.g., PCT Patent Publication No. WO 2008/036802, the disclosure of which is hereby incorporated by reference in its entirety for all purposes. When biotin-tyramide is used as the fluorogenic substrate, the $HRP-H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, any of the fluorophores described herein including an Alexa Fluor® dye (e.g., Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790), fluorescein, fluorescein isothiocyanate (FITC), Oregon Green™, rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

Additional proximity-based techniques suitable for use in the assay methods of the present invention for autoantibody isotyping are described in PCT Patent Publication No. WO 2008/036802, the disclosure of which is hereby incorporated by reference in its entirety for all purposes.

Methods for detecting anti-TNF antibodies and anti-drug antibodies such as HACA and HAHA are further described in PCT Publication No. WO 2011/056590, the disclosure of which is hereby incorporated by reference in its entirety for all purposes.

In another aspect, the present invention provides a method for optimizing therapy and/or reducing toxicity in a subject receiving a course of therapy for the treatment of a TNFα-mediated disease or disorder, the method comprising:
 (a) analyzing a sample obtained from the subject to determine the presence, level, or genotype of one or more markers in the sample;
 (b) applying a statistical algorithm to the presence, level, or genotype of the one or more markers determined in step (a); and
 (c) determining a subsequent dose of the course of therapy for the subject or whether a different course of therapy should be administered to the subject based upon the statistical algorithm applied in step (b).

In some embodiments, the course of therapy comprises an anti-TNFα drug such as an anti-TNFα antibody. In certain instances, the anti-TNFα antibody is selected from the group consisting of REMICADE™ (infliximab), ENBREL™ (etanercept), HUMIRA™ (adalimumab), CIMZIA® (certolizumab pegol), and combinations thereof.

In certain embodiments, the one or more (e.g., a plurality of) markers comprise an anti-TNFα drug (e.g., anti-TNFα antibody), an autoantibody to an anti-TNFα drug such as an anti-TNFα antibody (e.g., HACA, HAHA, HAMA, and/or isotypes thereof), a cytokine, a genetic marker, or combinations thereof. In certain instances, the cytokine is a member selected from the group consisting of TNFα, IL-6, IL-1β, IFN-γ, IL-10, and combinations thereof. In certain other instances, the genetic marker is a mutation in an inflammatory pathway gene. In particular embodiments, the genetic marker is a mutation in a gene selected from the group consisting of NOD2/CARD15, ATG16L1, IL23R, a human leukocyte antigen (HLA) gene, a cytokine gene, DLG5, OCTN, and combinations thereof.

In other embodiments, step (a) of the method for optimizing therapy and/or reducing toxicity comprises determining the presence, level, or genotype of two, three, four, five, six, seven, eight, nine, ten, or more markers in said sample. In certain embodiments, the sample is selected from the group consisting of serum, plasma, whole blood, and stool.

In yet other embodiments, the statistical algorithm comprises a learning statistical classifier system. In certain instances, the learning statistical classifier system is selected from the group consisting of a random forest, classification and regression tree, boosted tree, neural network, support vector machine, general chi-squared automatic interaction detector model, interactive tree, multiadaptive regression spline, machine learning classifier, and combinations thereof. In some embodiments, the statistical algorithm comprises a single learning statistical classifier system. In other embodiments, the statistical algorithm comprises a combination of at least two learning statistical classifier systems. In some instances, at least two learning statistical classifier systems are applied in tandem.

In some embodiments, the method for optimizing therapy and/or reducing toxicity further comprises sending the results from said determination of step (c) to a clinician. In other embodiments, step (b) of the method for optimizing therapy and/or reducing toxicity further comprises applying the statistical algorithm to the presence, level, or genotype of the one or more markers determined at an earlier time during the course of therapy.

In further embodiments, the subsequent dose of the course of therapy is increased, decreased, or maintained based upon the statistical algorithm applied in step (b). In certain instances, the different course of therapy comprises a different anti-TNFα drug (e.g., anti-TNFα antibody). In other instances, the different course of therapy comprises the current course of therapy along with an immunosuppressive agent.

In some embodiments, the anti-TNFα drug (e.g., anti-TNFα antibody) is detected with an assay comprising:
 (a) contacting labeled TNFα with the sample to form a labeled complex with the anti-TNFα drug;
 (b) subjecting the labeled complex to size exclusion chromatography to separate the labeled complex; and (c) detecting the labeled complex, thereby detecting the anti-TNFα drug.

In certain instances, the anti-TNFα drug (e.g., anti-TNFα antibody) is a member selected from the group consisting of REMICADE™ (infliximab), ENBREL™ (etanercept), HUMIRA™ (adalimumab), CIMZIA® (certolizumab pegol), and combinations thereof. In some instances, the labeled TNFα is a fluorophore labeled TNFα. In other instances, the detected anti-TNFα drug (e.g., anti-TNFα antibody) is quantitated. In some embodiments, the labeled complex is eluted first, followed by free labeled TNFα. In other embodiments, the size exclusion chromatography is size exclusion-high performance liquid chromatography (SE-HPLC).

In other embodiments, the autoantibody to the anti-TNFα drug (e.g., anti-TNFα antibody) is detected with an assay comprising:
  (a) contacting labeled anti-TNFα drug with the sample to form a labeled complex with the autoantibody;
  (b) subjecting the labeled complex to size exclusion chromatography to separate the labeled complex; and
  (c) detecting the labeled complex, thereby detecting the autoantibody.

In certain instances, the autoantibody is selected from the group consisting of human anti-mouse antibody (HAMA), human anti-chimeric antibody (HACA), human anti-humanized antibody (HAHA), and combinations thereof. In certain other instances, the labeled anti-TNFα drug (e.g., anti-TNFα antibody) is selected from the group consisting of REMICADE™ (infliximab), ENBREL™ (etanercept), HUMIRA™ (adalimumab), CIMZIA® (certolizumab pegol), and combinations thereof.

In some embodiments, the labeled anti-TNFα drug (e.g., anti-TNFα antibody) is a fluorophore labeled anti-TNFα drug (e.g., anti-TNFα antibody). In other embodiments, the detected autoantibody is quantitated. In further embodiments, the labeled complex is eluted first, followed by free labeled anti-TNFα drug (e.g., anti-TNFα antibody). In particular embodiments, the size exclusion chromatography is size exclusion-high performance liquid chromatography (SE-HPLC).

In certain embodiments, the autoantibody to the anti-TNFα drug (e.g., anti-TNFα antibody) is detected with any of the assays described herein for detecting the presence (or absence) or level of at least one isotype (e.g., a plurality of isotypes) of an autoantibody to an anti-TNFα drug.

In other embodiments, the assay methods described in PCT Publication No. WO 2011/056590 (the disclosure of which is hereby incorporated by reference in its entirety for all purposes) for detecting anti-TNFα drugs (e.g., anti-TNFα antibodies) and autoantibodies to anti-TNFα drugs (e.g., HACA, HAHA, HAMA, etc.) can be used in the methods described herein for optimizing therapy and/or reducing toxicity.

In certain embodiments, the methods of the present invention provide information useful for guiding treatment decisions for patients receiving anti-TNF drug therapy, e.g., by determining when or how to adjust or modify (e.g., increase or decrease) the subsequent dose of an anti-TNF drug, by determining when or how to combine an anti-TNF drug (e.g., at an increased, decreased, or same dose) with one or more immunosuppressive agents such as methotrexate (MTX) or azathioprine (AZA), and/or by determining when or how to change the current course of therapy (e.g., switch to a different anti-TNF drug). Accordingly, the present invention finds utility in aiding or assisting in patient management by determining patient immune status.

In other embodiments, the assay methods described herein can be used to predict tolerability (e.g., toxicity) to an anti-TNF drug, especially to an anti-TNFα antibody in a subject having an autoimmune disorder (e.g., rheumatoid arthritis, Crohn's Disease, and the like). In this method, by assaying the subject for the presence (or absence) or level of one or more ADA isotypes, it is possible to predict whether the subject will tolerate the anti-TNF drug therapy (e.g., not develop or experience side-effects such as an immune response to the anti-TNF drug).

In yet other embodiments, the assay methods described herein can be used to monitor an autoimmune disorder in a subject having the autoimmune disorder comprising assaying the subject for the presence (or absence) or level of one or more ADA isotypes over time. In this method, it is possible to monitor whether the subject tolerates the anti-TNF drug therapy over the given time period.

IV. Statistical Analysis

In some aspects, the present invention provides methods for optimizing anti-TNF drug therapy, reducing toxicity associated with anti-TNF drug therapy, and/or monitoring the efficacy of anti-TNF drug treatment by applying a statistical algorithm to one or more (e.g., a combination of two, three, four, five, six, seven, or more) biochemical markers, serological markers, and/or genetic markers. In particular embodiments, quantile analysis is applied to the presence, level, and/or genotype of one or more markers to guide treatment decisions for patients receiving anti-TNF drug therapy. In other embodiments, one or a combination of two of more learning statistical classifier systems are applied to the presence, level, and/or genotype of one or more markers to guide treatment decisions for patients receiving anti-TNF drug therapy. The statistical analyses of the methods of the present invention advantageously provide improved sensitivity, specificity, negative predictive value, positive predictive value, and/or overall accuracy for determining when or how to adjust or modify (e.g., increase or decrease) the subsequent dose of an anti-TNF drug, to combine an anti-TNF drug (e.g., at an increased, decreased, or same dose) with one or more immunosuppressive agents such as methotrexate (MTX) or azathioprine (AZA), and/or to change the current course of therapy (e.g., switch to a different anti-TNF drug).

The term "statistical analysis" or "statistical algorithm" or "statistical process" includes any of a variety of statistical methods and models used to determine relationships between variables. In the present invention, the variables are the presence, level, or genotype of at least one marker of interest. Any number of markers can be analyzed using a statistical analysis described herein. For example, the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In certain preferred embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In certain embodiments, the present invention involves detecting or determining the presence, level (e.g., magnitude), and/or genotype of one or more markers of interest using quartile analysis. In this type of statistical analysis, the level of a marker of interest is defined as being in the first quartile (<25%), second quartile (25-50%), third quartile (51%-<75%), or fourth quartile (75-100%) in relation to a reference database of samples. These quartiles may be assigned a quartile score of 1, 2, 3, and 4, respectively. In certain instances, a marker that is not detected in a sample is assigned a quartile score of 0 or 1, while a marker that is detected (e.g., present) in a sample (e.g., sample is positive for the marker) is assigned a quartile score of 4. In some embodiments, quartile 1 represents samples with the lowest marker levels, while quartile 4 represent samples with the highest marker levels. In other embodiments, quartile 1 represents samples with a particular marker genotype (e.g., wild-type allele), while quartile 4 represent samples with another particular marker genotype (e.g., allelic variant). The reference database of samples can include a large spectrum of patients with a TNFα-mediated disease or disorder such as, e.g., IBD. From such a database, quartile cut-offs can be established. A non-limiting example of quartile analysis suitable for use in the present invention is described in, e.g., Mow et al., *Gastroenterology*, 126:414-24 (2004).

In some embodiments, the statistical analyses of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological and/or genomic samples) from healthy individuals and patients with a TNFα-mediated disease or disorder such as, e.g., IBD (e.g., CD and/or UC). For example, samples from patients diagnosed by a physician, preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

As used herein, the term "sensitivity" includes the probability that a method of the present invention for optimizing anti-TNF drug therapy, reducing toxicity associated with anti-TNF drug therapy, and/or monitoring the efficacy of anti-TNF drug treatment gives a positive result when the sample is positive, e.g., having the predicted therapeutic response to anti-TNF drug therapy or toxicity associated with anti-TNF drug therapy. Sensitivity is calculated as the number of true positive results divided by the sum of the true positives and false negatives. Sensitivity essentially is a measure of how well the present invention correctly identifies those who have the predicted therapeutic response to anti-TNF drug therapy or toxicity associated with anti-TNF drug therapy from those who do not have the predicted therapeutic response or toxicity. The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" includes the probability that a method of the present invention for optimizing anti-TNF drug therapy, reducing toxicity associated with anti-TNF drug therapy, and/or monitoring the efficacy of anti-TNF drug treatment gives a negative result when the sample is not positive, e.g., not having the predicted therapeutic response to anti-TNF drug therapy or toxicity associated with anti-TNF drug therapy. Specificity is calculated as the number of true negative results divided by the sum of the true negatives and false positives. Specificity essentially is a measure of how well the present invention excludes those who do not have the predicted therapeutic response to anti-TNF drug therapy or toxicity associated with anti-TNF drug therapy from those who do have the predicted therapeutic response or toxicity. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "negative predictive value" or "NPV" includes the probability that an individual identified as not having the predicted therapeutic response to anti-TNF drug therapy or toxicity associated with anti-TNF drug therapy actually does not have the predicted therapeutic response or toxicity. Negative predictive value can be calculated as the number of true negatives divided by the sum of the true negatives and false negatives. Negative predictive value is determined by the characteristics of the methods of the present invention as well as the prevalence of the disease in the population analyzed. The statistical methods and models can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" includes the probability that an individual identified as having the predicted therapeutic response to anti-TNF drug therapy or toxicity associated with anti-TNF drug therapy actually has the predicted therapeutic response or toxicity. Positive predictive value can be calculated as the number of true positives divided by the sum of the true positives and false positives. Positive predictive value is determined by the characteristics of the methods of the present invention as well as the prevalence of the disease in the population analyzed. The statistical methods and models can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the present invention, the statistical methods and models can be selected to produce a desired clinical parameter for a clinical population with a particular prevalence for a TNFα-mediated disease or disorder such as, e.g., IBD. As a non-limiting example, statistical methods and models can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" includes the accuracy with which a method of the present invention optimizes anti-TNF drug therapy, reduces toxicity associated with anti-TNF drug therapy, and/or monitors the efficacy of anti-TNF drug treatment. Overall accuracy is calculated as the sum of the true positives and true negatives divided by the total number of sample results and is affected by the prevalence of the disease in the population analyzed. For example, the statistical methods and models can be selected such that the overall accuracy in a patient population having a disease prevalence is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

V. Inflammatory Markers

A variety of inflammatory markers, including biochemical markers, serological markers, protein markers, genetic markers, and other clinical or echographic characteristics, are suitable for use in the methods of the present invention for optimizing therapy, reducing toxicity, and/or monitoring the efficacy of therapeutic treatment with therapeutic agents such as biologics (e.g., anti-TNF drugs). In certain aspects, the methods described herein utilize the application of an algorithm (e.g., statistical analysis) to the presence, concentration level, and/or genotype determined for one or more of the inflammatory markers to aid or assist in optimizing anti-TNF drug therapy, reducing toxicity associated with anti-TNF drug therapy, or monitoring the efficacy of therapeutic treatment with an anti-TNF drug.

Non-limiting examples of inflammatory markers include: (i) biochemical, serological, and protein markers such as, e.g., cytokines, acute phase proteins, cellular adhesion molecules, and combinations thereof; and (ii) genetic markers such as, e.g., any of the genes set forth in Table 1 (e.g., NOD2).

A. Cytokines

The determination of the presence or level of at least one cytokine in a sample is particularly useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain aspects, the presence or level of at least one cytokine including, but not limited to, TNF-α, TNF-related weak inducer of apoptosis (TWEAK), osteoprotegerin (OPG), IFN-α, IFN-β, IFN-γ, IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27 is determined in a sample. In certain other aspects, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and CX$_3$CL1 is determined in a sample. In certain further aspects, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample. Preferably, the presence or level of TNFα, IL-6, IL-1β, IFN-γ, and/or IL-10 is determined.

In certain instances, the presence or level of a particular cytokine is detected at the level of mRNA expression with an assay such as, for example, a hybridization assay or an amplification-based assay. In certain other instances, the presence or level of a particular cytokine is detected at the level of protein expression using, for example, an immunoassay (e.g., ELISA) or an immunohistochemical assay. Suitable ELISA kits for determining the presence or level of a cytokine such as IL-6, IL-1β, or TWEAK in a serum, plasma, saliva, or urine sample are available from, e.g., R&D Systems, Inc. (Minneapolis, Minn.), Neogen Corp. (Lexington, K.Y.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

The human IL-6 polypeptide sequence is set forth in, e.g., Genbank Accession No. NP_000591. The human IL-6 mRNA (coding) sequence is set forth in, e.g., Genbank Accession No. NM_000600. One skilled in the art will appreciate that IL-6 is also known as interferon beta 2 (IFNB2), HGF, HSF, and BSF2.

The human IL-1β polypeptide sequence is set forth in, e.g., Genbank Accession No. NP_000567. The human IL-1β mRNA (coding) sequence is set forth in, e.g., Genbank Accession No. NM_000576. One skilled in the art will appreciate that IL-1β is also known as IL1F2 and IL-1beta.

The human TWEAK polypeptide sequence is set forth in, e.g., Genbank Accession Nos. NP_003800 and AAC51923. The human TWEAK mRNA (coding) sequence is set forth in, e.g., Genbank Accession Nos. NM_003809 and BC104420. One skilled in the art will appreciate that TWEAK is also known as tumor necrosis factor ligand superfamily member 12 (TNFSF12), APO3 ligand (APO3L), CD255, DR3 ligand, growth factor-inducible 14 (Fn14) ligand, and UNQ181/PRO207.

B. Acute Phase Proteins

The determination of the presence or level of one or more acute-phase proteins in a sample is also useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. Preferably, the presence or level of CRP and/or SAA is determined.

In certain instances, the presence or level of a particular acute-phase protein is detected at the level of mRNA expression with an assay such as, for example, a hybridization assay or an amplification-based assay. In certain other instances, the presence or level of a particular acute-phase protein is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. Additional methods for determining CRP levels include, e.g., immunoturbidimetry assays, rapid immunodiffusion assays, and visual agglutination assays. Suitable ELISA kits for determining the presence or level of SAA in a sample such as serum, plasma, saliva, urine, or stool are available from, e.g., Antigenix America Inc. (Huntington Station, N.Y.), Abazyme (Needham, Mass.), USCN Life (Missouri City, Tex.), and/or U.S. Biological (Swampscott, Mass.).

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322. The human SAA mRNA (coding) sequence is set forth in, e.g., Genbank Accession No. NM_000331. One skilled in the art will appreciate that SAA is also known as PIG4, TP53I4, MGC111216, and SAA1.

C. Cellular Adhesion Molecules (IgSF CAMs)

The determination of the presence or level of one or more immunoglobulin superfamily cellular adhesion molecules in a sample is also useful in the present invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (L1CAM), cell adhesion molecule with homology to L1CAM (close homolog of L1) (CRL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). Preferably, the presence or level of ICAM-1 and/or VCAM-1 is determined.

1. Intercellular Adhesion Molecule-1 (ICAM-1)

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., J., Gastroenterol., 32:480 (1997); and Rijcken et al., Gut, 51:529 (2002)). ICAM-1 is encoded by the intercellular adhesion molecule 1 gene (ICAM1; Entrez GeneID:3383; Genbank Accession No. NM_000201) and is produced after processing of the intercellular adhesion molecule 1 precursor polypeptide (Genbank Accession No. NP_000192).

2. Vascular Cell Adhesion Molecule-1 (VCAM-1)

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In certain instances, the presence or level of an IgSF CAM is detected at the level of mRNA expression with an assay such as, for example, a hybridization assay or an amplification-based assay. In certain other instances, the presence or level of an IgSF CAM is detected at the level of protein expression using, for example, an immunoassay (e.g., ELISA) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

D. Genetic Markers

The determination of the presence or absence of allelic variants in one or more genetic markers in a sample is also useful in the present invention. Non-limiting examples of genetic markers include, but are not limited to, any of the inflammatory pathway genes and corresponding SNPs that can be genotyped as set forth in Table 1 (e.g., a NOD2/CARD15 gene, an IL12/IL23 pathway gene, etc.). Preferably, the presence or absence of at least one allelic variant, e.g., a single nucleotide polymorphism (SNP), in the NOD2/CARD15 gene and/or one or more genes in the IL12/IL23 pathway is determined. See, e.g., Barrett et al., Nat. Genet., 40:955-62 (2008) and Wang et al., Amer. J. Hum. Genet., 84:399-405 (2009).

TABLE 1

| Gene | SNP |
|---|---|
| NOD2 (R702W) - SNP8 | rs2066844 |
| NOD2 (G908R) - SNP12 | rs2066845 |
| NOD2 (3020insC) - SNP13 | rs5743293 |
| ATG16L1 (T300A) | rs2241880 |
| IL23R (R381Q) | rs11209026 |
| DLG5 | rs2165047 |
| NOD2/CARD15 | rs2066847 |
| IL23R | rs11465804 |
| ATG16L1 | rs3828309 |
| MST1 | rs3197999 |
| PTGER4 | rs4613763 |
| IRGM | rs11747270 |
| TNFSF15 | rs4263839 |
| ZNF365 | rs10995271 |
| NKX2-3 | rs11190140 |
| PTPN2 | rs2542151 |
| PTPN22 | rs2476601 |
| ITLN1 | rs2274910 |
| IL12B | rs10045431 |
| CDKAL1 | rs6908425 |
| CCR6 | rs2301436 |
| JAK2 | rs10758669 |

TABLE 1-continued

| Gene | SNP |
| --- | --- |
| C11orf30 | rs7927894 |
| LRRK2, MUC19 | rs11175593 |
| ORMDL3 | rs2872507 |
| STAT3 | rs744166 |
| ICOSLG | rs762421 |
| GCKR | rs780094 |
| BTNL2, SLC26A3, HLA-DRB1, HLA-DQA1 | rs3763313 |
| PUS10 | rs13003464 |
| CCL2, CCL7 | rs991804 |
| LYRM4 | rs12529198 |
| SLC22A23 | rs17309827 |
| IL18RAP | rs917997 |
| IL12RB2 | rs7546245 |
| IL12RB1 | rs374326 |
| CD3D | rs3212262 |
| CD3G | rs3212262 |
| CD247 | rs704853 |
| JUN | rs6661505 |
| CD3E | rs7937334 |
| IL18R1 | rs1035127 |
| CCR5 | |
| MAPK14 | rs2237093 |
| IL18 | rs11214108 |
| IFNG | rs10878698 |
| MAP2K6 | rs2905443 |
| STAT4 | rs1584945 |
| IL12A | rs6800657 |
| TYK2 | rs12720356 |
| ETV5 | rs9867846 |
| MAPK8 | rs17697885 |
| IRGM | rs13361189 |
| IRGM | rs4958847 |
| IRGM | rs1000113 |
| IRGM | rs11747270 |
| TL1A/TNFSF15 | rs6478109 |
| TL1A/TNFSF15 | rs6478108 |
| TL1A/TNFSF15 | rs4263839 |
| PTN22 | rs2476601 |
| CCR6 | rs1456893 |
| CCR6 | rs2301436 |
| 5p13/PTGER4 | rs1373692 |
| 5p13/PTGER4 | rs4495224 |
| 5p13/PTGER4 | rs7720838 |
| 5p13/PTGER4 | rs4613763 |
| ITLN1 | rs2274910 |
| ITLN1 | rs9286879 |
| ITLN1 | rs11584383 |
| IBD5/5q31 | rs2188962 |
| IBD5/5q31 | rs252057 |
| IBD5/5q31 | rs10067603 |
| GCKR | rs780094 |
| TNFRSF6B | rs1736135 |
| ZNF365 | rs224136 |
| ZNF365 | rs10995271 |
| C11orf30 | rs7927894 |
| LRRK2; MUC19 | rs1175593 |
| IL-27 | rs8049439 |
| TLR2 | rs4696480 |
| TLR2 | rs3804099 |
| TLR2 | rs3804100 |
| TLR2 | rs55743704 |
| TLR2 | rs2405432 |
| TLR4 (D299G) | rs4986790 |
| TLR4 (T399I) | rs4986791 |
| TLR4 (S360N) | rs4987233 |
| TLR9 | rs187084 |
| TLR9 | rs352140 |
| NFC4 | rs4821544 |
| KIF21B | rs11584383 |
| IKZF1 | rs1456893 |
| C11orf30 | rs7927894 |
| CCL2, CCL7 | rs991804 |
| ICOSLG | rs762421 |
| TNFAIP3 | rs7753394 |
| FLJ45139 | rs2836754 |
| PTGER4 | rs4613763 |
| ECM1 | rs7511649 |
| ECM1 (T130M) | rs3737240 |
| ECM1 (G290S) | rs13294 |
| GLI1 (G933D) | rs2228224 |
| GLI1 (Q1100E) | rs2228226 |
| MDR1 (3435C > T) | rs1045642 |
| MDR1 (A893S/T) | rs2032582 |
| MAGI2 | rs6962966 |
| MAGI2 | rs2160322 |
| IL26 | rs12815372 |
| IFNG, IL26 | rs1558744 |
| IFNG, IL26 | rs971545 |
| IL26 | rs2870946 |
| ARPC2 | rs12612347 |
| IL10, IL19 | rs3024493 |
| IL10, IL19 | rs3024505 |
| IL23R | rs1004819 |
| IL23R | rs2201841 |
| IL23R | rs11465804 |
| IL23R | rs10889677 |
| BTLN2 | rs9268480 |
| HLA-DRB1 | rs660895 |
| MEP1 | rs6920863 |
| MEP1 | rs2274658 |
| MEP1 | rs4714952 |
| MEP1 | rs1059276 |
| PUS10 | rs13003464 |
| PUS10 | rs6706689 |
| RNF186 | rs3806308 |
| RNF186 | rs1317209 |
| RNF186 | rs6426833 |
| FCGR2A, C | rs10800309 |
| CEP72 | rs4957048 |
| DLD, LAMB1 | rs4598195 |
| CAPN10, KIF1A | rs4676410 |
| IL23R | rs11805303 |
| IL23R | rs7517847 |
| IL12B/p40 | rs1368438 |
| IL12B/p40 | rs10045431 |
| IL12B/p40 | rs6556416 |
| IL12B/p40 | rs6887695 |
| IL12B/p40 | rs3212227 |
| STAT3 | rs744166 |
| JAK2 | rs10974914 |
| JAK2 | rs10758669 |
| NKX2-3 | rs6584283 |
| NKX2-3 | rs10883365 |
| NKX2-3 | rs11190140 |
| IL18RAP | rs917997 |
| LYRM4 | rs12529198 |
| CDKAL1 | rs6908425 |
| MAGI2 | rs2160322 |
| TNFRSF6B | rs2160322 |
| TNFRSF6B | rs2315008 |
| TNFRSF6B | rs4809330 |
| PSMG1 | rs2094871 |
| PSMG1 | rs2836878 |
| PTPN2 | rs2542151 |
| MST1/3p21 | rs9858542 |
| MST1/3p21 | rs3197999 |
| SLC22A23 | rs17309827 |
| MHC | rs660895 |
| XBP1 | rs35873774 |
| ICOSLG1 | rs762421 |
| BTLN2 | rs3763313 |
| BTLN2 | rs2395185 |
| BTLN2 | rs9268480 |
| ATG5 | rs7746082 |
| CUL2, CREM | rs17582416 |
| CARD9 | rs4077515 |
| ORMDL3 | rs2872507 |
| ORMDL3 | rs2305480 |

Additional SNPs useful in the present invention include, e.g., rs2188962, rs9286879, rs11584383, rs7746082, rs1456893, rs1551398, rs17582416, rs3764147, rs1736135, rs4807569, rs7758080, and rs8098673. See, e.g., Barrett et al., Nat. Genet., 40:955-62 (2008).

1. NOD2/CARD15

The determination of the presence or absence of allelic variants such as SNPs in the NOD2/CARD15 gene is particularly useful in the present invention. As used herein, the term "NOD2/CARD15 variant" or "NOD2 variant" includes a nucleotide sequence of a NOD2 gene containing one or more changes as compared to the wild-type NOD2 gene or an amino acid sequence of a NOD2 polypeptide containing one or more changes as compared to the wild-type NOD2 polypeptide sequence. NOD2, also known as CARD15, has been localized to the IBD1 locus on chromosome 16 and identified by positional-cloning (Hugot et al., Nature, 411:599-603 (2001)) as well as a positional candidate gene strategy (Ogura et al., Nature, 411:603-606 (2001); Hampe et al., Lancet, 357:1925-1928 (2001)). The IBD1 locus has a high multipoint linkage score (MLS) for inflammatory bowel disease (MLS=5.7 at marker D16S411 in 16q12). See, e.g., Cho et al., Inflamm. Bowel Dis., 3:186-190 (1997); Akolkar et al., Am. J. Gastroenterol., 96:1127-1132 (2001); Ohmen et al., Hum. Mol. Genet., 5:1679-1683 (1996); Parkes et al., Lancet, 348:1588 (1996); Cavanaugh et al., Ann. Hum. Genet., 62:291-8 (1998); Brant et al., Gastroenterology, 115:1056-1061 (1998); Curran et al., Gastroenterology, 115:1066-1071 (1998); Hampe et al., Am. J. Hum. Genet., 64:808-816 (1999); and Annese et al., Eur. J. Hum. Genet., 7:567-573 (1999).

The mRNA (coding) and polypeptide sequences of human NOD2 are set forth in, e.g., Genbank Accession Nos. NM_022162 and NP_071445, respectively. In addition, the complete sequence of human chromosome 16 clone RP11-327F22, which includes NOD2, is set forth in, e.g., Genbank Accession No. AC007728. Furthermore, the sequence of NOD2 from other species can be found in the GenBank database.

The NOD2 protein contains amino-terminal caspase recruitment domains (CARDs), which can activate NF-kappa B (NF-kB), and several carboxy-terminal leucine-rich repeat domains (Ogura et al., J. Biol. Chem., 276:4812-4818 (2001)). NOD2 has structural homology with the apoptosis regulator Apaf-1/CED-4 and a class of plant disease resistant gene products (Ogura et al., supra). Similar to plant disease resistant gene products, NOD2 has an amino-terminal effector domain, a nucleotide-binding domain and leucine rich repeats (LRRs). Wild-type NOD2 activates nuclear factor NF-kappa B, making it responsive to bacterial lipopolysaccharides (LPS; Ogura et al., supra; Inohara et al., J. Biol. Chem., 276:2551-2554 (2001). NOD2 can function as an intercellular receptor for LPS, with the leucine rich repeats required for responsiveness.

Variations at three single nucleotide polymorphisms in the coding region of NOD2 have been previously described. These three SNPs, designated R702W ("SNP 8"), G908R ("SNP 12"), and 1007fs ("SNP 13"), are located in the carboxy-terminal region of the NOD2 gene (Hugot et al., supra). A further description of SNP 8, SNP 12, and SNP 13, as well as additional SNPs in the NOD2 gene suitable for use in the invention, can be found in, e.g., U.S. Pat. Nos. 6,835,815; 6,858,391; and 7,592,437; and U.S. Patent Publication Nos. 20030190639, 20050054021, and 20070072180.

In some embodiments, a NOD2 variant is located in a coding region of the NOD2 locus, for example, within a region encoding several leucine-rich repeats in the carboxy-terminal portion of the NOD2 polypeptide. Such NOD2 variants located in the leucine-rich repeat region of NOD2 include, without limitation, R702W ("SNP 8") and G908R ("SNP 12"). A NOD2 variant useful in the invention can also encode a NOD2 polypeptide with reduced ability to activate NF-kappa B as compared to NF-kappa B activation by a wild-type NOD2 polypeptide. As a non-limiting example, the NOD2 variant 1007fs ("SNP 13") results in a truncated NOD2 polypeptide which has reduced ability to induce NF-kappa B in response to LPS stimulation (Ogura et al., Nature, 411:603-606 (2001)).

A NOD2 variant useful in the invention can be, for example, R702W, G908R, or 1007fs. R702W, G908R, and 1007fs are located within the coding region of NOD2. In one embodiment, a method of the invention is practiced with the R702W NOD2 variant. As used herein, the term "R702W" includes a single nucleotide polymorphism within exon 4 of the NOD2 gene, which occurs within a triplet encoding amino acid 702 of the NOD2 protein. The wild-type NOD2 allele contains a cytosine (c) residue at position 138,991 of the AC007728 sequence, which occurs within a triplet encoding an arginine at amino acid 702. The R702W NOD2 variant contains a thymine (t) residue at position 138,991 of the AC007728 sequence, resulting in an arginine (R) to tryptophan (W) substitution at amino acid 702 of the NOD2 protein. Accordingly, this NOD2 variant is denoted "R702W" or "702W" and can also be denoted "R675W" based on the earlier numbering system of Hugot et al., supra. In addition, the R702W variant is also known as the "SNP 8" allele or a "2" allele at SNP 8. The NCBI SNP ID number for R702W or SNP 8 is rs2066844. The presence of the R702W NOD2 variant and other NOD2 variants can be conveniently detected, for example, by allelic discrimination assays or sequence analysis.

A method of the invention can also be practiced with the G908R NOD2 variant. As used herein, the term "G908R" includes a single nucleotide polymorphism within exon 8 of the NOD2 gene, which occurs within a triplet encoding amino acid 908 of the NOD2 protein. Amino acid 908 is located within the leucine rich repeat region of the NOD2 gene. The wild-type NOD2 allele contains a guanine (g) residue at position 128,377 of the AC007728 sequence, which occurs within a triplet encoding glycine at amino acid 908. The G908R NOD2 variant contains a cytosine (c) residue at position 128,377 of the AC007728 sequence, resulting in a glycine (G) to arginine (R) substitution at amino acid 908 of the NOD2 protein. Accordingly, this NOD2 variant is denoted "G908R" or "908R" and can also be denoted "G881R" based on the earlier numbering system of Hugot et al., supra. In addition, the G908R variant is also known as the "SNP 12" allele or a "2" allele at SNP 12. The NCBI SNP ID number for G908R SNP 12 is rs2066845.

A method of the invention can also be practiced with the 1007fs NOD2 variant. This variant is an insertion of a single nucleotide that results in a frame shift in the tenth leucine-rich repeat of the NOD2 protein and is followed by a premature stop codon. The resulting truncation of the NOD2 protein appears to prevent activation of NF-kappaB in response to bacterial lipopolysaccharides (Ogura et al., supra). As used herein, the term "1007fs" includes a single nucleotide polymorphism within exon 11 of the NOD2 gene, which occurs in a triplet encoding amino acid 1007 of the NOD2 protein. The 1007fs variant contains a cytosine which has been added at position 121,139 of the AC007728 sequence, resulting in a frame shift mutation at amino acid 1007. Accordingly, this NOD2 variant is denoted "1007fs" and can also be denoted "3020insC" or "980fs" based on the earlier numbering system of Hugot et al., supra. In addition, the 1007fs NOD2 variant is also known as the "SNP 13" allele or a "2" allele at SNP 13. The NCBI SNP ID number for 1007fs or SNP 13 is rs2066847.

One skilled in the art recognizes that a particular NOD2 variant allele or other polymorphic allele can be conveniently defined, for example, in comparison to a Centre d'Etude du Polymorphisme Humain (CEPH) reference individual such as the individual designated 1347-02 (Dib et al., Nature, 380:152-154 (1996)), using commercially available reference DNA obtained, for example, from PE Biosystems (Foster City, CA). In addition, specific information on SNPs can be obtained from the dbSNP of the National Center for Biotechnology Information (NCBI).

A NOD2 variant can also be located in a non-coding region of the NOD2 locus. Non-coding regions include, for example, intron sequences as well as 5' and 3' untranslated sequences. A non-limiting example of a NOD2 variant allele located in a non-coding region of the NOD2 gene is the JW1 variant, which is described in Sugimura et al., Am. J. Hum. Genet., 72:509-518 (2003) and U.S. Patent Publication No. 20070072180. Examples of NOD2 variant alleles located in the 3' untranslated region of the NOD2 gene include, without limitation, the JW15 and JW16 variant alleles, which are described in U.S. Patent Publication No. 20070072180. Examples of NOD2 variant alleles located in the 5' untranslated region (e.g., promoter region) of the NOD2 gene include, without limitation, the JW17 and JW18 variant alleles, which are described in U.S. Patent Publication No. 20070072180.

As used herein, the term "JW1 variant allele" includes a genetic variation at nucleotide 158 of intervening sequence 8 (intron 8) of the NOD2 gene. In relation to the AC007728 sequence, the JW1 variant allele is located at position 128,143. The genetic variation at nucleotide 158 of intron 8 can be, but is not limited to, a single nucleotide substitution, multiple nucleotide substitutions, or a deletion or insertion of one or more nucleotides. The wild-type sequence of intron 8 has a cytosine at position 158. As non-limiting examples, a JW1 variant allele can have a cytosine (c) to adenine (a), cytosine (c) to guanine (g), or cytosine (c) to thymine (t) substitution at nucleotide 158 of intron 8. In one embodiment, the JW1 variant allele is a change from a cytosine (c) to a thymine (t) at nucleotide 158 of NOD2 intron 8.

The term "JW15 variant allele" includes a genetic variation in the 3' untranslated region of NOD2 at nucleotide position 118,790 of the AC007728 sequence. The genetic variation at nucleotide 118,790 can be, but is not limited to, a single nucleotide substitution, multiple nucleotide substitutions, or a deletion or insertion of one or more nucleotides. The wild-type sequence has an adenine (a) at position 118,790. As non-limiting examples, a JW15 variant allele can have an adenine (a) to cytosine (c), adenine (a) to guanine (g), or adenine (a) to thymine (t) substitution at nucleotide 118,790. In one embodiment, the JW15 variant allele is a change from an adenine (a) to a cytosine (c) at nucleotide 118,790.

As used herein, the term "JW16 variant allele" includes a genetic variation in the 3' untranslated region of NOD2 at nucleotide position 118,031 of the AC007728 sequence. The genetic variation at nucleotide 118,031 can be, but is not limited to, a single nucleotide substitution, multiple nucleotide substitutions, or a deletion or insertion of one or more nucleotides. The wild-type sequence has a guanine (g) at position 118,031. As non-limiting examples, a JW16 variant allele can have a guanine (g) to cytosine (c), guanine (g) to adenine (a), or guanine (g) to thymine (t) substitution at nucleotide 118,031. In one embodiment, the JW16 variant allele is a change from a guanine (g) to an adenine (a) at nucleotide 118,031.

The term "JW17 variant allele" includes a genetic variation in the 5' untranslated region of NOD2 at nucleotide position 154,688 of the AC007728 sequence. The genetic variation at nucleotide 154,688 can be, but is not limited to, a single nucleotide substitution, multiple nucleotide substitutions, or a deletion or insertion of one or more nucleotides. The wild-type sequence has a cytosine (c) at position 154,688. As non-limiting examples, a JW17 variant allele can have a cytosine (c) to guanine (g), cytosine (c) to adenine (a), or cytosine (c) to thymine (t) substitution at nucleotide 154,688. In one embodiment, the JW17 variant allele is a change from a cytosine (c) to a thymine (t) at nucleotide 154,688.

As used herein, the term "JW18 variant allele" includes a genetic variation in the 5' untranslated region of NOD2 at nucleotide position 154,471 of the AC007728 sequence. The genetic variation at nucleotide 154,471 can be, but is not limited to, a single nucleotide substitution, multiple nucleotide substitutions, or a deletion or insertion of one or more nucleotides. The wild-type sequence has a cytosine (c) at position 154,471. As non-limiting examples, a JW 18 variant allele can have a cytosine (c) to guanine (g), cytosine (c) to adenine (a), or cytosine (c) to thymine (t) substitution at nucleotide 154,471. In one embodiment, the JW18 variant allele is a change from a cytosine (c) to a thymine (t) at nucleotide 154,471.

It is understood that the methods of the invention can be practiced with these or other NOD2 variant alleles located in a coding region or non-coding region (e.g., intron or promoter region) of the NOD2 locus. It is further understood that the methods of the invention can involve determining the presence of one, two, three, four, or more NOD2 variants, including, but not limited to, the SNP 8, SNP 12, and SNP 13 alleles, and other coding as well as non-coding region variants.

VI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Novel Mobility Shift Assay for Measuring Levels of Anti-TNFα Biologics

This example illustrates a novel homogeneous assay for measuring anti-TNFα drug concentration in a patient sample (e.g., serum) using size exclusion chromatography to detect the binding of the anti-TNFα drug to fluorescently labeled TNFα. The assay is advantageous because it obviates the need for wash steps, uses fluorophores that allow for detection on the visible and/or IR spectra which decreases background and serum interference issues, increases the ability to detect anti-TNFα drugs in patients with a low titer due to the high sensitivity of fluorescent label detection, and occurs as a liquid phase reaction, thereby reducing the chance of any changes in the epitope by attachment to a solid surface such as an ELISA plate.

In one exemplary embodiment, TNFα is labeled with a fluorophore (e.g., Alexa$_{647}$), wherein the fluorophore can be detected on either or both the visible and IR spectra. The labeled TNFα is incubated with human serum in a liquid phase reaction to allow the anti-TNFα drug present in the serum to bind. The labeled TNFα can also be incubated with known amounts of the anti-TNFα drug in a liquid phase reaction to create a standard curve. Following incubation, the samples are loaded directly onto a size exclusion column. Binding of the anti-TNFα drug to the labeled TNFα results in a leftward shift of the peak compared to labeled TNFα alone. The concentration of the anti-TNFα drug present in the serum sample can then be compared to the standard curve and controls.

FIG. 1 shows an example of the assay of the present invention wherein size exclusion HPLC is used to detect the binding between TNFα-Alexa$_{647}$ and HUMIRA™ (adalimumab). As shown in FIG. 1, the binding of HUMIRA™ to TNFα-Alexa$_{647}$ caused a shift of the TNFα-Alexa$_{647}$ peak to the left.

Figure 2A:
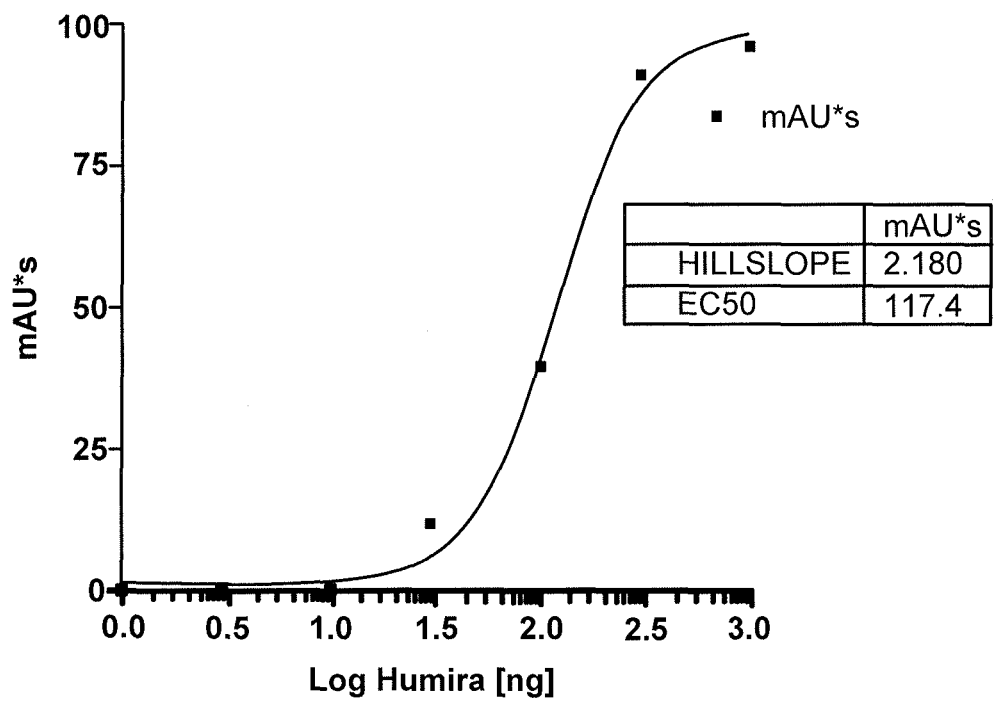
FIGS. 2A-2C show dose response curves of HUMIRA™ binding to TNFα-Alexa$_{647}$.
Figure 2B:
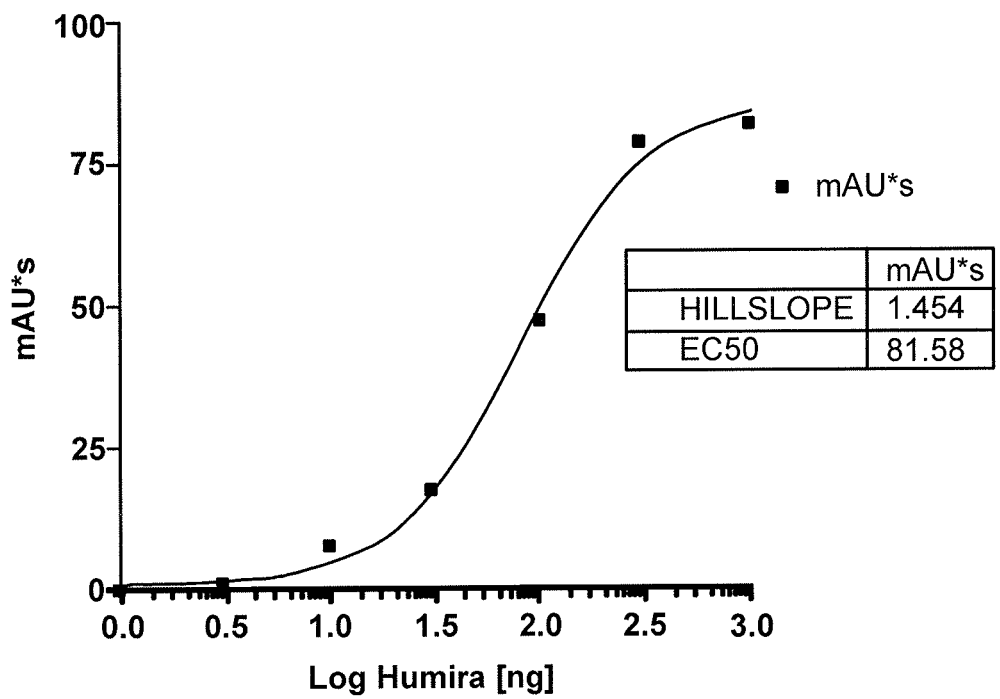
Figure 2C:
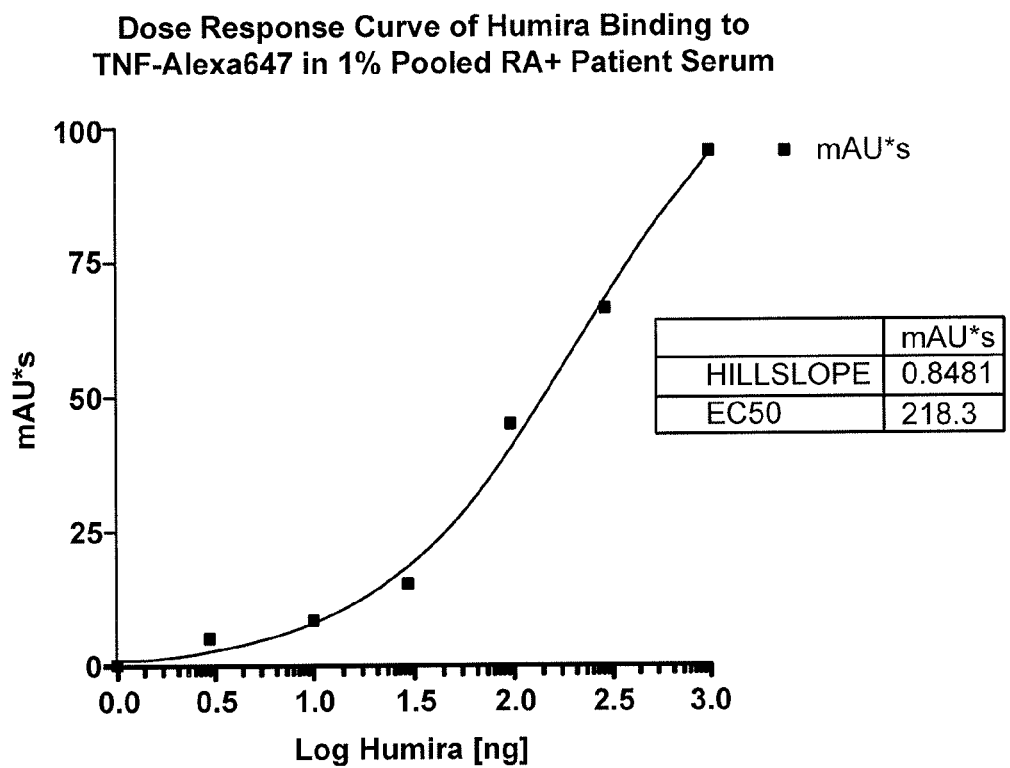

FIGS. 2A-2C show dose response curves of HUMIRA™ binding to TNFα-Alexa$_{647}$. In particular, FIG. 2A shows that HUMIRA™ dose-dependently increased the shift of TNFα-Alexa$_{647}$ in the size exclusion chromatography assay. FIG. 2B shows that the presence of 1% human serum did not have a significant effect on the shift of TNFα-Alexa$_{647}$ in the size exclusion chromatography assay. FIG. 2C shows that the presence of pooled RF-positive serum did not have a significant effect on the shift of TNFα-Alexa$_{647}$ in the size exclusion chromatography assay.

As such, this example demonstrates the utility of the present invention in monitoring patients receiving an anti-TNFα drug such as HUMIRA™: (1) to guide in the determination of the appropriate drug dosage; (2) to evaluate drug pharmacokinetics, e.g., to determine whether the drug is being cleared from the body too quickly; and (3) to guide treatment decisions, e.g., whether to switch from the current anti-TNFα drug to a different TNFα inhibitor or to another type of therapy.

Example 2

Novel Mobility Shift Assay for Measuring HACA and HAHA Levels

This example illustrates a novel homogeneous assay for measuring autoantibody (e.g., HACA and/or HAHA) concentrations in a patient sample (e.g., serum) using size exclusion chromatography to detect the binding of these autoantibodies to fluorescently labeled anti-TNFα drug. The assay is advantageous because it obviates the need for wash steps which remove low affinity HACA and HAHA, uses fluorophores that allow for detection on the visible and/or IR spectra which decreases background and serum interference issues, increases the ability to detect HACA and HAHA in patients with a low titer due to the high sensitivity of fluorescent label detection, and occurs as a liquid phase reaction, thereby reducing the chance of any changes in the epitope by attachment to a solid surface such as an ELISA plate.

The clinical utility of measuring autoantibodies (e.g., HACA, HAHA, etc.) that are generated against TNFα inhibitors is illustrated by the fact that HACAs were detected in 53%, 21%, and 7% of rheumatoid arthritis patients treated with 1 mg/kg, 3 mg/kg, and 10 mg/kg infliximab. When infliximab was combined with methotrexate, the incidence of antibodies was lower 15%, 7%, and 0%, which indicates that concurrent immunosuppressive therapy is effective in lowering anti-drug responses, but also indicates that a high dose of anti-TNFα antibody might lead to tolerance. In Crohn's disease, a much higher incidence was reported; after the fifth infusion, 61% of patients had HACA.

The clinical response was shortened when HACAs were present. See, Rutgeerts, N Engl. J. Med., 348:601-608 (2003). A retrospective study of infliximab and HACA levels measured over a 3 year period from 2005 to 2008 in 155 patients demonstrated that HACAs were detected in 22.6% (N=35) of patients with inflammatory bowel disease. See, Afif et al., "Clinical Utility of Measuring Infliximab and Human Anti-Chimeric Antibody Levels in Patients with Inflammatory Bowel Disease"; paper presented at Digestive Disease Week; May 30-Jun. 3, 2009; Chicago, Ill. The authors concluded that changing treatment based on clinical symptoms alone may lead to inappropriate management.

Figure 3:
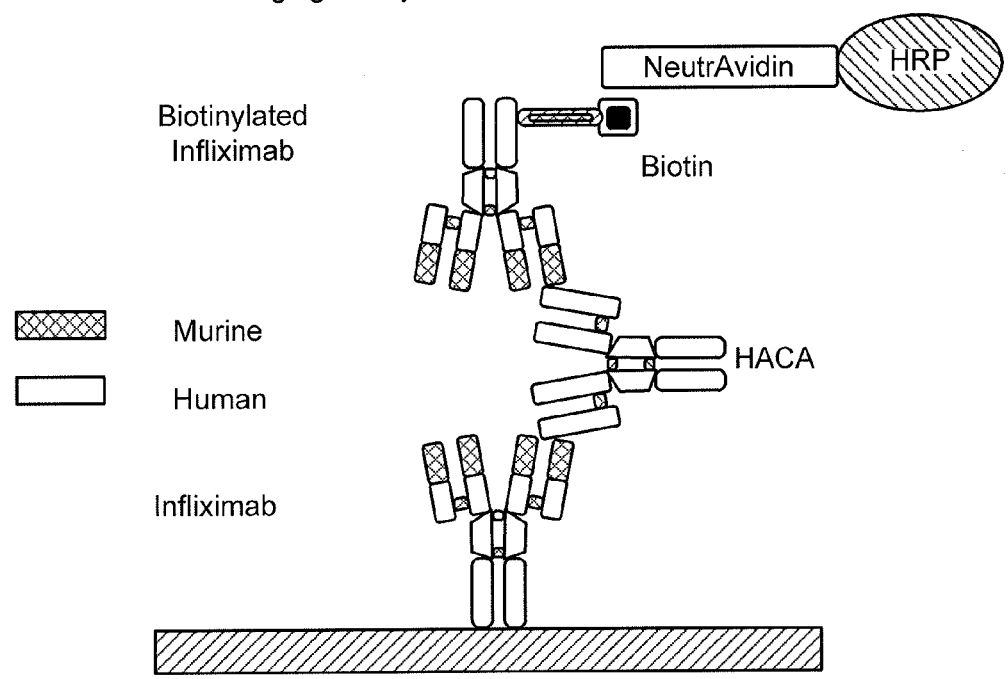
FIG. 3 shows a current ELISA-based method for measuring HACA levels, known as the bridging assay.

The homogeneous mobility shift assay is advantageous over current methods such as the bridging assay shown in FIG. 3 for measuring autoantibody (e.g., HACA and/or HAHA) concentrations in a patient sample because the inventive method is capable of measuring the concentration of autoantibodies such as HACA without non-specific binding and solid phase interference from the ELISA plate, without interference from the anti-TNFα drug (e.g., with the bridging assay, HACA measurements must be taken at anti-TNFα drug trough levels), and without any dependency on the multivalency of the antibody (e.g., IgG4 antibodies are not detected using the bridging assay because IgG4 antibodies are bispecific and cannot cross-link the same antigen). As such, the present invention has at least the following advantages over current methods: avoids attachment of antigens to solid surfaces (denaturation avoided); eliminates the IgG4 effect; overcomes therapeutic antibody trough issues; detects antibodies with weak affinities; eliminates non-specific binding of irrelevant IgGs; and increases the sensitivity and specificity of detection.

Figure 4:
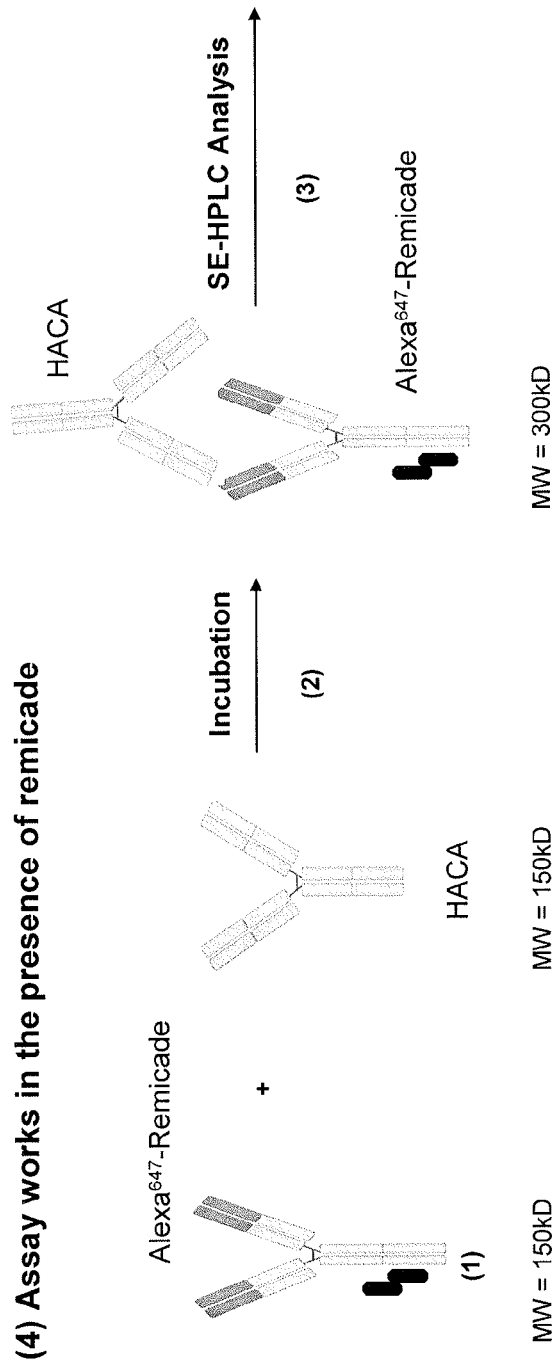
FIG. 4 illustrates an exemplary outline of the autoantibody detection assays of the present invention for measuring the concentrations of HACA/HAHA generated against REMICADE™.

In one exemplary embodiment, an anti-TNFα drug (e.g., REMICADE™) is labeled with a fluorophore (e.g., Alexa$_{647}$), wherein the fluorophore can be detected on either or both the visible and IR spectra. The labeled anti-TNFα drug is incubated with human serum in a liquid phase reaction to allow HACA and HAHA present in the serum to bind. The labeled anti-TNFα drug can also be incubated with known amounts of an anti-IgG antibody in a liquid phase reaction to create a standard curve. Following incubation, the samples are loaded directly onto a size exclusion column. Binding of the autoantibodies to the labeled anti-TNFα drug results in a leftward shift of the peak compared to labeled drug alone. The concentration of HACA and HAHA present in the serum sample can then be compared to the standard curve and controls. FIG. 4 illustrates an exemplary outline of the autoantibody detection assays of the present invention for measuring the concentrations of HACA/HAHA generated against REMICADE™. In certain instances, high HACA/HAHA levels indicate that the current therapy with REMICADE™ should be switched to another anti-TNFα drug such as HUMIRA™.

The principle of this assay is based on the mobility shift of the antibody bound Alexa$_{647}$-labeled Remicade complex versus free Alexa$_{647}$-labeled Remicade on size exclusion-high performance liquid chromatography (SE-HPLC) due to the increase in molecular weight of the complex.

The chromatography in this example was performed on an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.4, at a flow-rate of 0.5 mL/min with UV detection at 650 nm. A 100 μL sample volume is loaded onto the column for each analysis.

The antibody bound Alexa$_{647}$-labeled Remicade complex is formed by incubating a known amount of the antibody and Alexa₆₄₇-labeled Remicade in the 1×PBS, pH 7.3, elution buffer at room temperature for 1 hour before SE-HPLC analysis.

Figure 5:
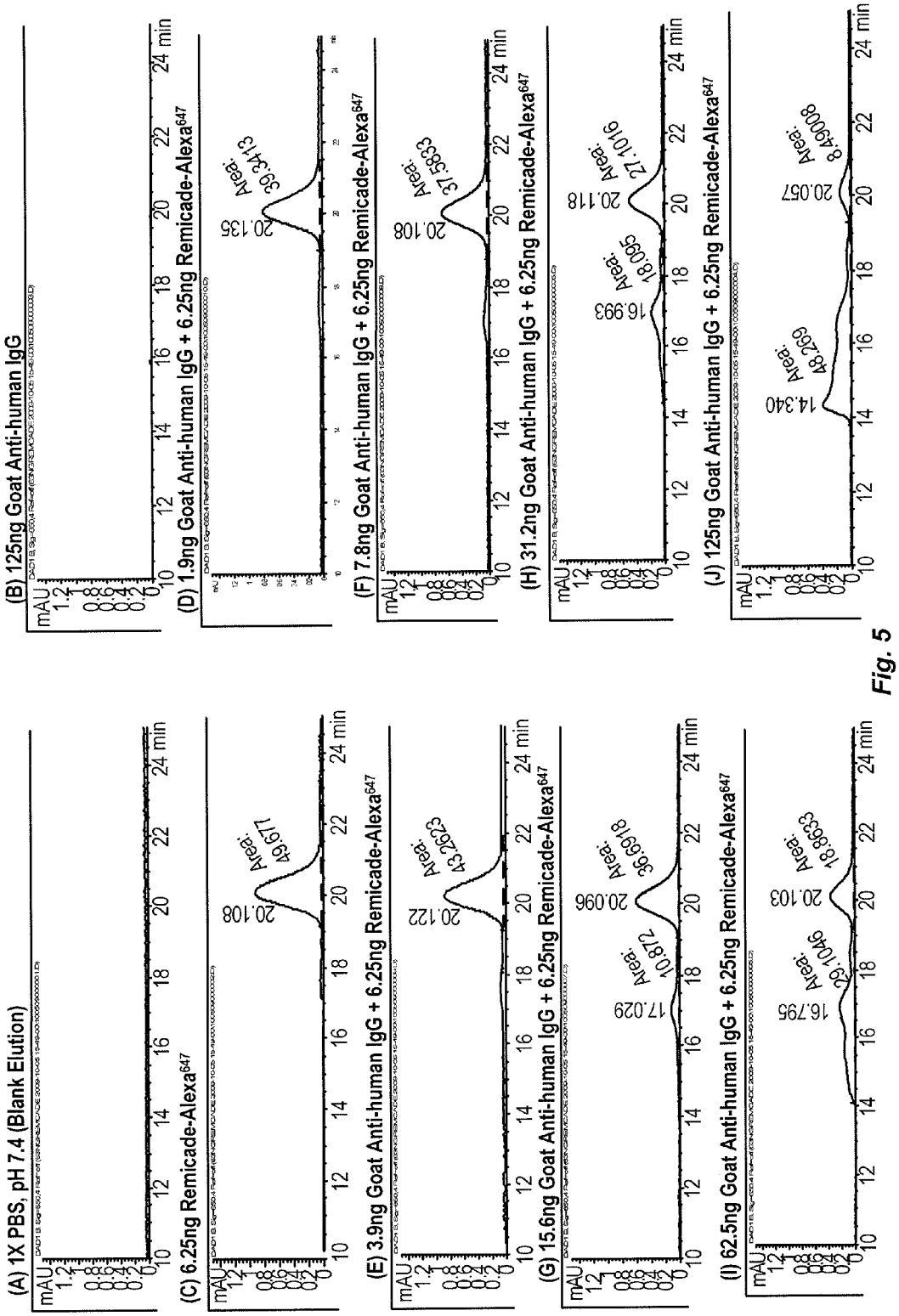
FIG. 5 shows a dose response analysis of anti-human IgG antibody binding to REMICADE™-Alexa$_{647}$.
Figure 6:
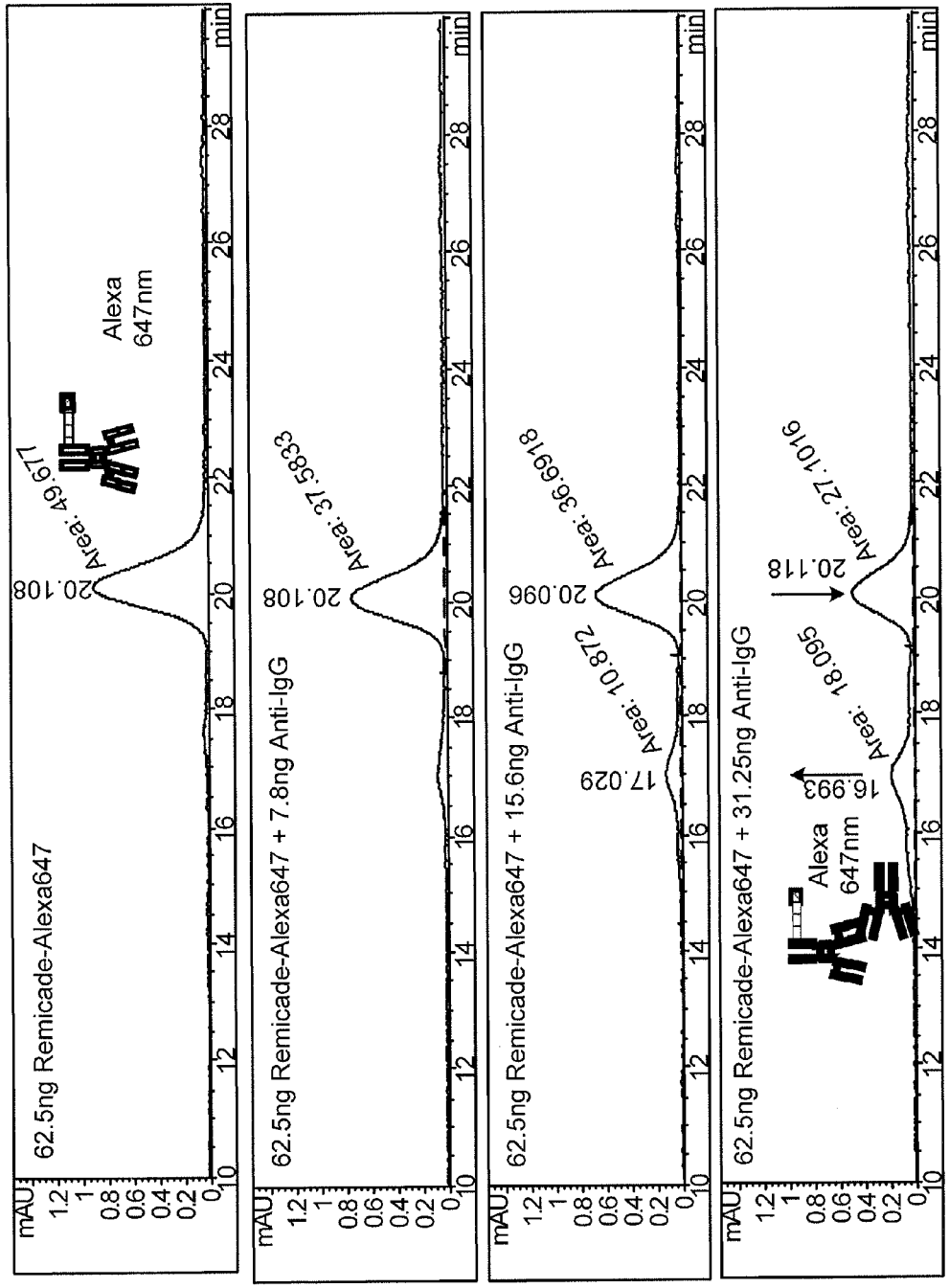
FIG. 6 shows a second dose response analysis of anti-human IgG antibody binding to REMICADE™-Alexa$_{647}$.
Figure 7A:
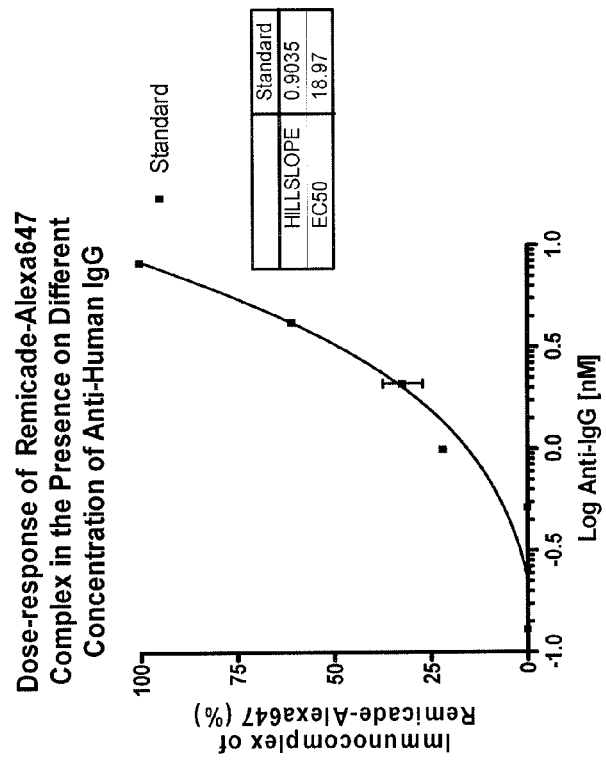
FIGS. 7A-7B show dose response curves of anti-human IgG antibody binding to REMICADE™-Alexa$_{647}$.
Figure 7B:
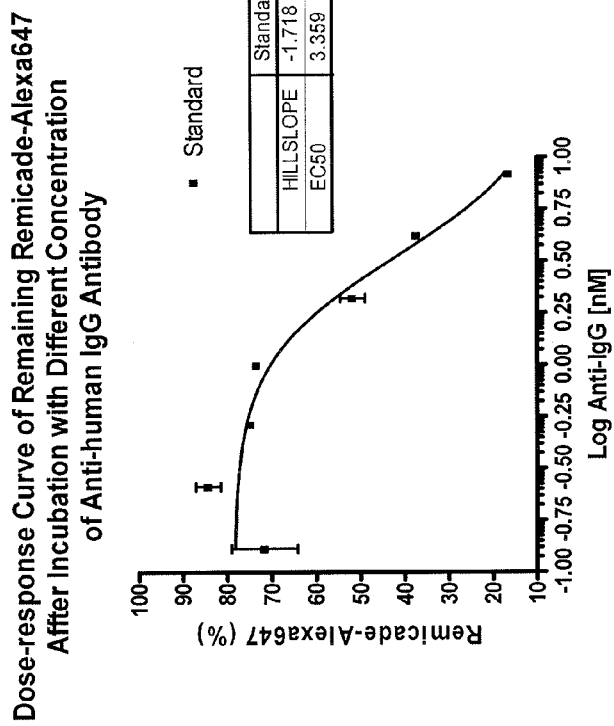
Figure 8A:
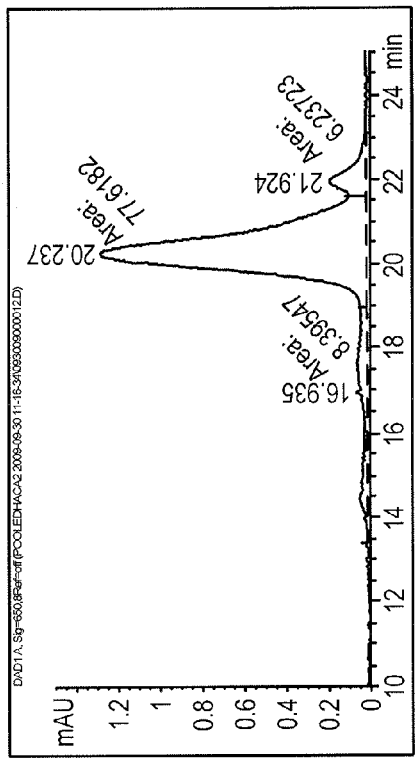
FIGS. 8A-8D show REMICADE™-Alexa$_{647}$ immunocomplex formation in normal human serum and HACA positive serum.
Figure 8B:
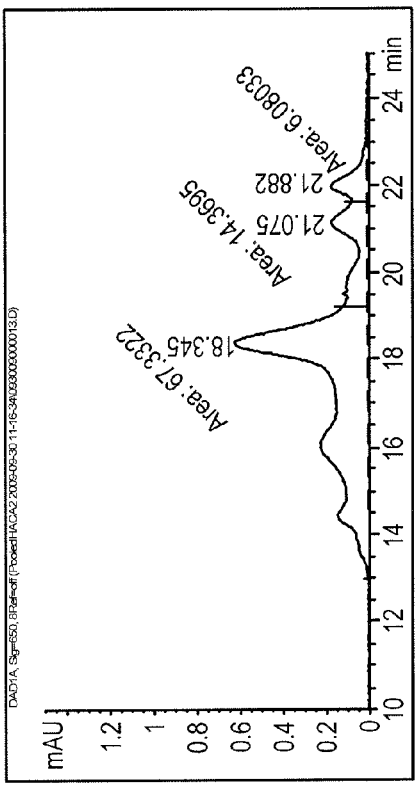
Figure 8C:
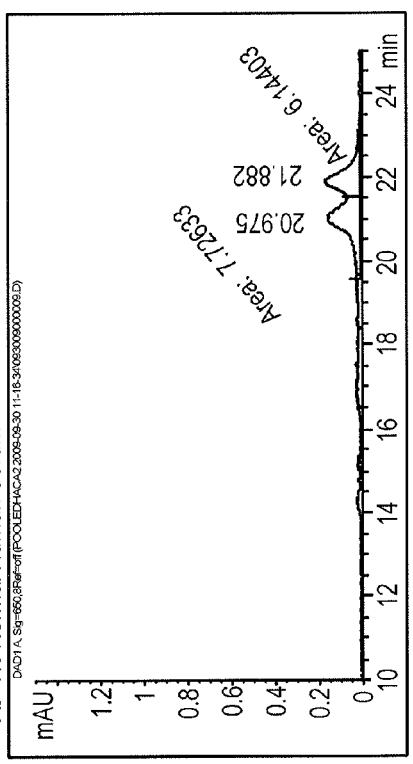
Figure 8D:
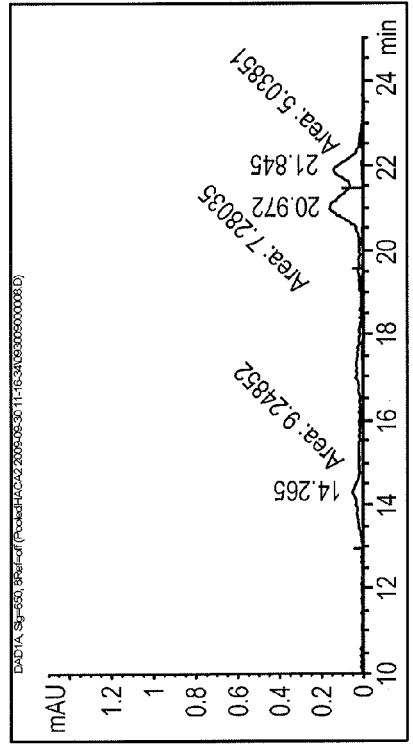
Figures 11A, 11B, 11C, 11D:
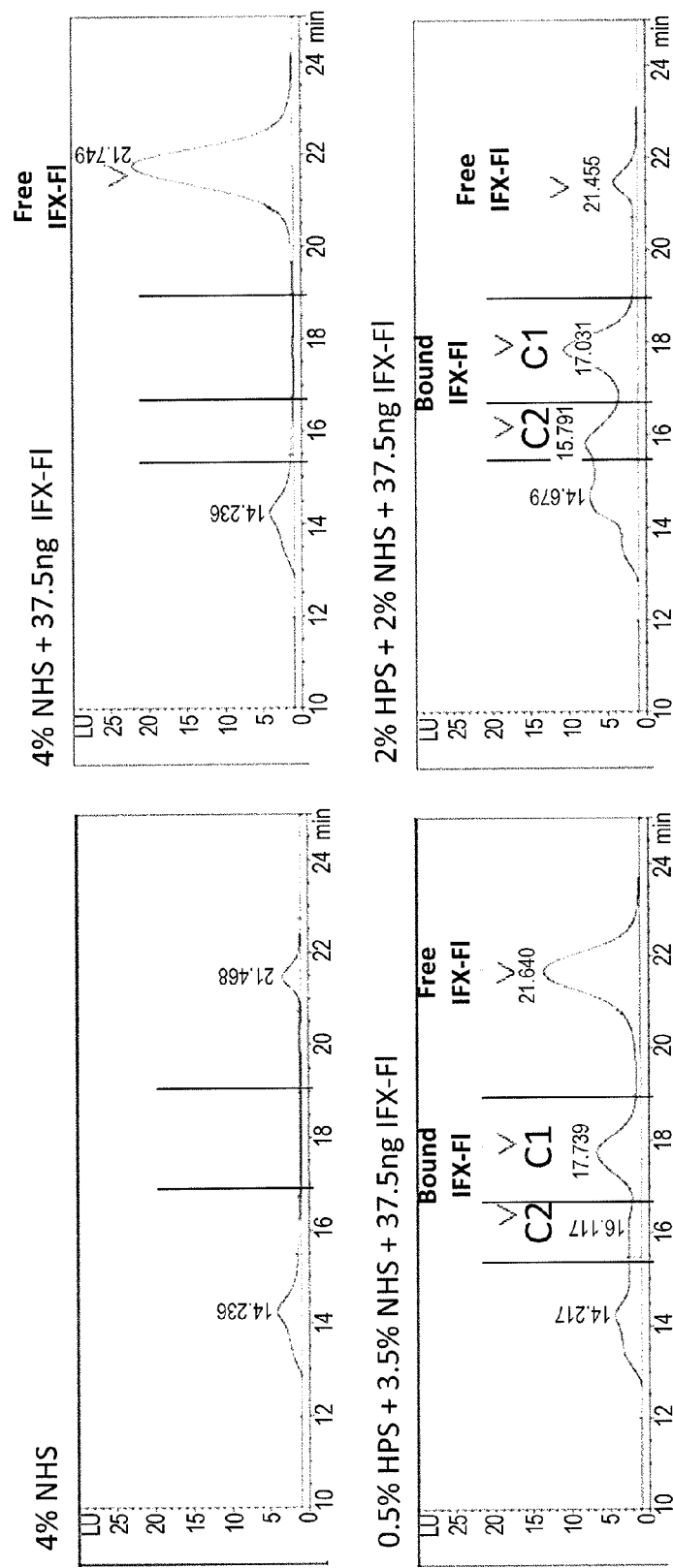
FIGS. 11A-11D show SE-HPLC profiles of fluorophore (Fl)-labeled infliximab (IFX) incubated with normal (NHS) or HACA-positive (HPS) serum. The addition of increasing amounts of HACA-positive serum to the incubation mixture dose-dependently shifted the IFX-Fl peak to the higher molecular mass eluting positions, C1 and C2.

FIG. 5 shows a dose response analysis of anti-human IgG antibody binding to REMICADE™-Alexa₆₄₇ as detected using the size exclusion chromatography assay of the present invention. The binding of anti-IgG antibody to REMICADE™-Alexa₆₄₇ caused a shift of the REMICADE™-Alexa₆₄₇ peak to the left. FIG. 6 shows a second dose response analysis of anti-human IgG antibody binding to REMICADE™-Alexa₆₄₇ as detected using the size exclusion chromatography assay of the present invention. Higher amounts of anti-IgG antibody resulted in a dose-dependent increase in the formation of anti-IgG/REMICADE™-Alexa₆₄₇ complexes, as indicated by a shift of the REMICADE™-Alexa₆₄₇ peak to the left. FIGS. 7A-7B show dose response curves of anti-IgG antibody binding to REMICADE™-Alexa₆₄₇.

FIGS. 8A-8D show REMICADE™-Alexa₆₄₇ immunocomplex formation in normal human serum and HACA positive serum as detected using the size exclusion chromatography assay of the present invention with 100 μA of injected sample. As shown in FIGS. 8A-8D, the binding of HACA present in patient samples to REMICADE™-Alexa₆₄₇ caused a shift of the REMICADE™-Alexa₆₄₇ peak to the left. As such, the size exclusion chromatography assay of the invention is particularly advantageous because it measures HACA in the presence of REMICADE™, can be utilized while the patient is on therapy, measures both weak and strong HACA binding, is a mix and read mobility shift assay, and can be extended to other approaches which use labeled REMICADE™ to equilibrate with HACA and REMICADE™.

FIG. 9 provides a summary of HACA measurements from 20 patient serum samples that were performed using the bridging assay or the mobility shift assay of the present invention. This comparative study demonstrates that the present methods have increased sensitivity over current methods because 3 samples that were negative for HACA as measured using the bridging assay were actually HACA positive when measured using the mobility shift assay of the present invention (see, Patient # SK07070305, SK07070595, and SK07110035).

As such, this example demonstrates the utility of the present invention in monitoring patients receiving an anti-TNFα drug (e.g., REMICADE™) to detect the presence or level of autoantibodies (e.g., HACA and/or HAHA) against the drug, because such immune responses can be associated with hypersensitive reactions and dramatic changes in pharmacokinetics and biodistribution of the anti-TNFα drug that preclude further treatment with the drug.

In conclusion, Examples 1 and 2 demonstrate that TNFα and anti-TNFα antibodies can be efficiently labeled with Alexa₆₄₇. When labeled TNFα-Alexa₆₄₇ was incubated with anti-TNFα antibodies, the retention time of the labeled TNFα/anti-TNFα antibody complex was shifted, and the amount of anti-TNFα antibody that caused the shift could be quantitated with HPLC. Furthermore, when labeled anti-TNFα antibody was incubated with anti-human IgG antibody, the retention time of the labeled anti-TNFα antibody/anti-IgG antibody complex was shifted, and the amount of anti-IgG antibody that caused the shift could be quantitated with HPLC. Moreover, low serum content in the assay system was shown to have little effect on HPLC analysis. Finally, a standard curve could be generated for the anti-TNFα antibody and HACA/HAHA assays and could be used to quantitate patient serum anti-TNFα antibody or HACA/HAHA levels. Advantageously, the present invention provides in certain aspects a mobility shift assay, such as a homogeneous mix and read assay developed to measure both drug and antibodies against the drug. A standard curve was generated for the anti-TNFα biologic Remicade and Humira and also for the HACA antibodies against Remicade. The mobility shift assay format, unlike ELISA, eliminates coating of antigens to solid surface and is not affected by non-specific binding of irrelevant IgGs. The assay format is simple, but very sensitive and can be used to detect all anti-TNFα biologic drugs (e.g., Remicade, Humira, Enbrel and Cimzia) as well as the neutralizing antibody (anti-Remicade™) in patient serum.

Example 3

Measurement of Human Anti-Chimeric Antibodies (HACA) and Infliximab (IFX) Levels in Patient Serum Using a Novel Mobility Shift Assay Abstract Background: Infliximab (IFX) is a chimeric monoclonal antibody therapeutic against TNFα that has been shown to be effective in treating autoimmune diseases such as rheumatoid arthritis (RA) and inflammatory bowel disease (IBD). However, antibodies against IFX were found in some IFX-treated patients through the detection of human anti-chimeric antibodies (HACA), which may reduce the drug's efficacy or induce adverse effects. Monitoring of HACA and IFX levels in individual patients may help to optimize the dosing and treatment with IFX. Current methods for detecting HACA are based on solid-phase assays, which are limited by the fact that the presence of IFX in the circulation may mask the presence of HACA and, therefore, measurement can only be done at least 8 weeks following a dose of IFX. Moreover, this time-lapse further confounds the assays because of the rapid clearance of the high molecular weight immune complexes in the blood circulation. To overcome these drawbacks, we have developed and evaluated a new method to measure serum IFX and HACA levels in patients treated with IFX.

Methods: A novel non-radiolabeled, liquid-phase, size-exclusion (SE)-HPLC mobility shift assay was developed to measure the HACA and IFX levels in serum from patients treated with IFX. The immuno-complex (e.g., TNFα/IFX or IFX/HACA), free TNFα or IFX, and the ratio of bound/free can be resolved and calculated with high sensitivity. Serum concentrations of IFX or HACA were determined with standard curves generated by incubating with different concentrations of IFX or pooled HACA-positive serum. Using this novel assay, we have measured IFX and HACA levels in sera collected from IBD patients treated with IFX who had relapsed and compared the results with those obtained by the traditional Bridge ELISA assay.

Results: Dose-response curves were generated from the novel assay with high sensitivity. Detection of HACA was demonstrated in the presence of excess IFX. In the 117 serum samples from patients treated with IFX, 65 samples were found to have IFX levels above the detection limit and the average was 11.0+6.9 mg/mL. For HACA levels, 33 (28.2%) samples were found to be positive while the Bridge ELISA assay detected only 24 positive samples. We also identified 9 false negatives and 9 false positives from the samples determined by the Bridge assay. HACA levels were found to be increased in 11 patients during the course of IFX treatment while the IFX levels were found to be significantly decreased.

Conclusions: A novel non-radiolabeled, liquid-phase, mobility shift assay has been developed to measure the IFX and HACA levels in serum from patients treated with IFX. The assay has high sensitivity and accuracy, and the obtained results were reproducible. This novel assay can advantageously be used to measure HACA and IFX levels while patients are on therapy.

Introduction

Tumor necrosis factor-alpha (TNFα) plays a pivotal role in the pathogenesis of autoimmune diseases such as Crohn's disease (CD) and rheumatoid arthritis (RA). It is well documented that blocking TNFα with therapeutic antibodies such as Infliximab (human-murine chimeric monoclonal IgG1κ) or adalimumab (fully human monoclonal antibody) reduces disease activity in CD and RA. However, about 30-40% of the patients do not respond to anti-TNFα therapy and some patients need higher doses or dosing frequency adjustments due to lack of sufficient response. Differences of drug bioavailability and pharmacokinetics in individual patients may contribute to the failure of the treatment. Immunogenicity of the drugs, which causes patients to develop HACA/HAHA, could result in a range of adverse reactions from mild allergic response to anaphylactic shock. These problems are now recognized by many investigators, drug-controlling agencies, health insurance companies, and drug manufacturers. Furthermore, many patients with secondary response failure to one anti-TNFα drug benefit from a switch to other anti-TNFα drugs, suggesting a role of neutralizing antibodies directed specifically against the protein used for treatment (Radstake et al., *Ann. Rheum. Dis.*, 68(11):1739-45 (2009)). Monitoring of patients for drug and HACA/HAHA levels is therefore warranted so that drug administration can be tailored to the individual patient and prolonged therapies can be given effectively and economically with little or no risk to patients (Bendtzen et al., *Scand. Gastroenterol.*, 44(7):774-81 (2009)).

Several enzyme-linked immunoassays have been used to assess the circulating levels of drugs and HACA/HAHA. FIG. 10 provides a summary of the current assays available for the measurement of HACA in comparison to the novel HACA assay of the present invention. One of the limitations of current methodologies is that antibody levels are difficult to measure when there is a measurable amount of drug in the circulation. In contrast to current solid-phase methods for detecting HACA in which measurements can only be performed at least 8 weeks following a dose of IFX, the novel assay of the present invention is a non-radiolabeled, liquid-phase, size-exclusion (SE)-HPLC assay that is capable of measuring HACA and IFX levels in serum from patients while being treated with IFX.

The following are rationales for measuring the serum concentrations of anti-TNFα biologic drugs and antibodies against TNFα biologic drugs in patients: (1) for PK studies in clinical trials; (2) it may be required by the FDA during clinical trials to monitor a patient's immune response to the biologic drug; (3) to monitor a patient's response to the biologic drug by measuring HACA or HAHA to guide the drug dosage for each patient; and (4) for use as a guide for switching to a different biologic drug when the initial drug fails.

Methods

SE-HPLC analysis of Infliximab (IFX) levels in patient serum. Human recombinant TNFα was labeled with a fluorophore ("Fl" such as, e.g., Alexa Fluor® 488) according to the manufacturer's instructions. Labeled TNFα was incubated with different amounts of IFX or patient serum for one hour at room temperature. Samples of 100 μL volume were analyzed by size-exclusion chromatography on an HPLC system. FLD was used to monitor the free TNFα-Fl and the bound TNFα-Fl immuno-complex based on their retention times. Serum IFX levels were calculated from the standard curve.

SE-HPLC analysis of HACA levels in patient serum. Purified IFX was labeled with Fl. Labeled IFX was incubated with different dilutions of pooled HACA-positive serum or diluted patient serum for one hour at room temperature. Samples of 100 μL volume were analyzed by size-exclusion chromatography on an HPLC system. FLD was used to monitor the free IFX-Fl and the bound IFX-Fl immuno-complex based on their retention times. The ratio of bound and free IFX-Fl was used to determine the HACA level.

Mobility Shift Assay Procedure to Measure HACA in Serum. The principle of this assay is based on the mobility shift of the HACA bound Fl-labeled Infliximab (IFX) complex versus free Fl-labeled IFX on size exclusion-high performance liquid chromatography (SE-HPLC) due to the increase in molecular weight of the complex. The chromatography is performed in an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.3, at a flow-rate of 0.5-1.0 mL/min with FLD detection. A 100 μL sample volume is loaded onto the column for each analysis. The HACA bound Fl-labeled IFX complex is formed by incubating serum from IFX treated patient and Fl-labeled IFX in the 1×PBS, pH 7.4, elution buffer at room temperature for 1 hour before SE-HPLC analysis. The assay was also run in the presence of varying interference agents, such as rheumatoid factor and TNF-α, in order to validate the assay.

Results

Figure 12A:
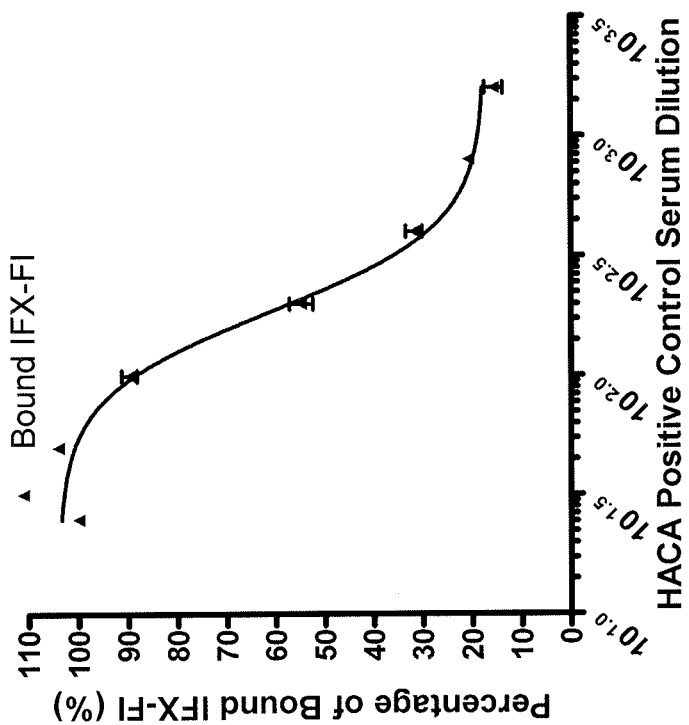
FIGS. 12A-12B show dose-response curves of the bound and free IFX-Fl generated with increasing dilutions of HACA-positive serum as determined by the mobility shift assay. (12A) Increasing dilutions of HACA-positive serum were incubated with 37.5 ng of IFX-Fl. The higher the dilution (less HACA) the more free IFX-Fl was found in the SE-HPLC analysis. (12B) Increasing dilutions of HACA-positive serum were incubated with 37.5 ng of IFX-Fl. The higher the dilution (less HACA) the less HACA bound IFX-Fl was found in the SE-HPLC analysis.
Figure 12B:
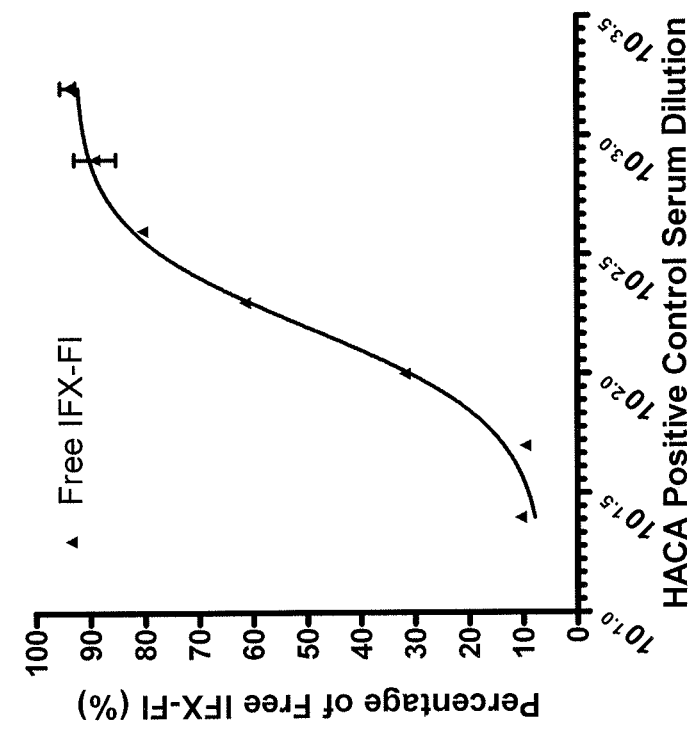
Figure 13A:
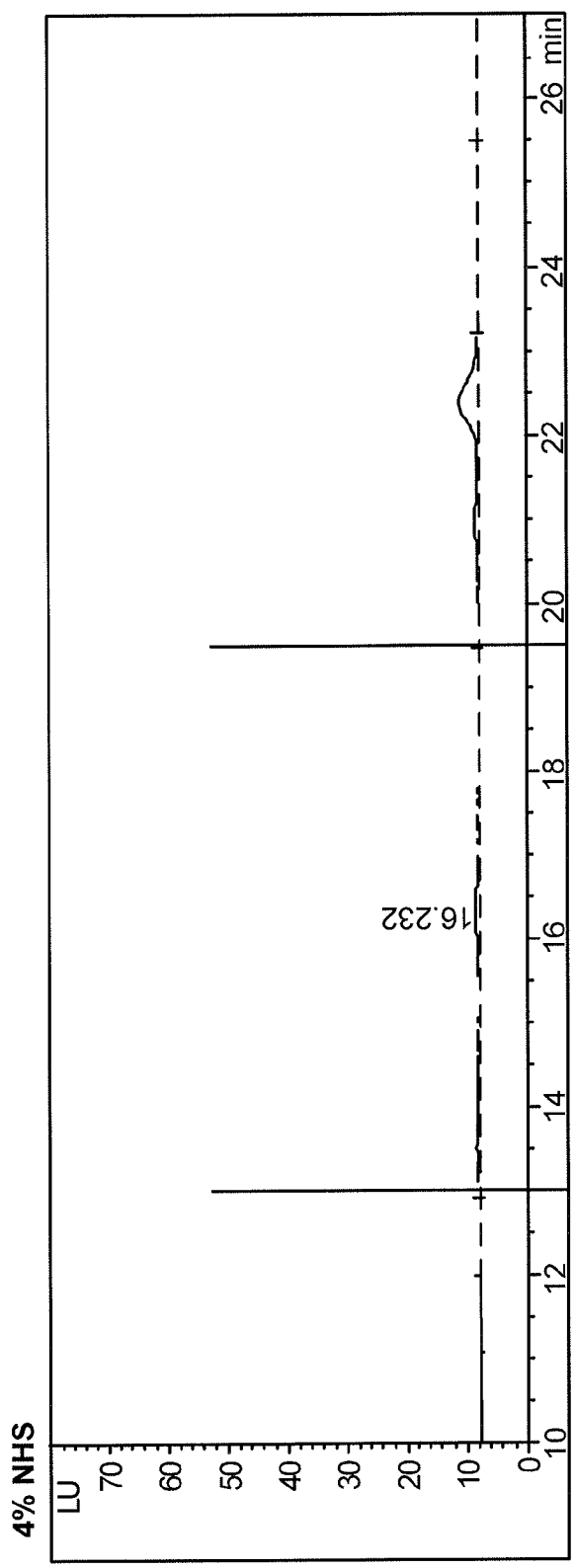
FIGS. 13A-13D show SE-HPLC profiles of TNFα-Fl incubated with normal (NHS) or IFX-spiked serum. The addition of increasing amounts of IFX-spiked serum to the incubation mixture dose-dependently shifted the fluorescent TNFα peak to the higher molecular mass eluting positions.
Figure 13B:
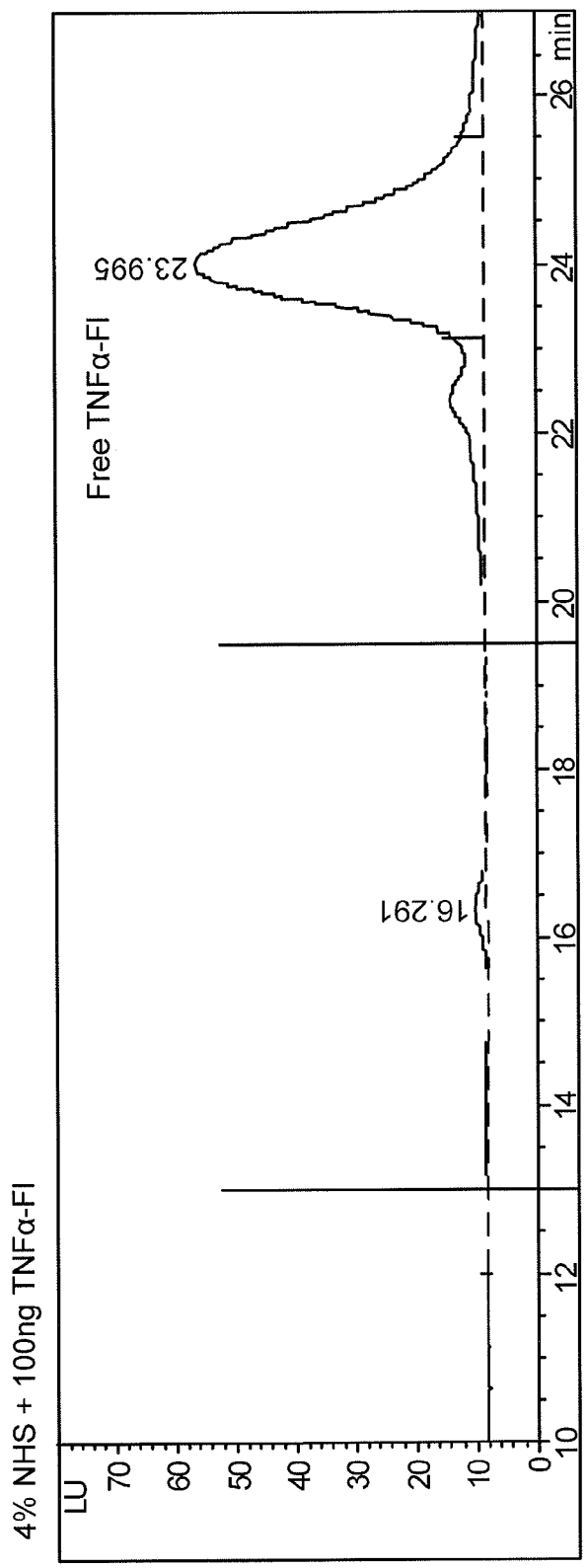
Figure 13C:
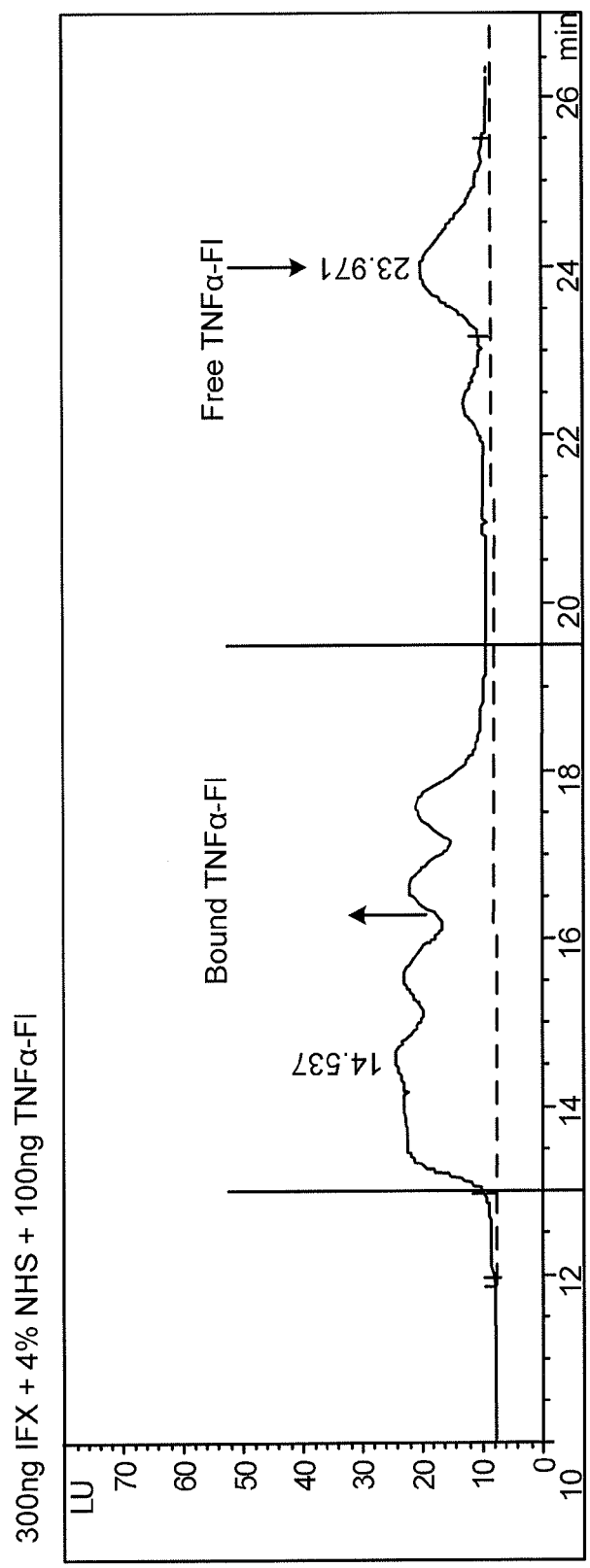
Figure 13D:
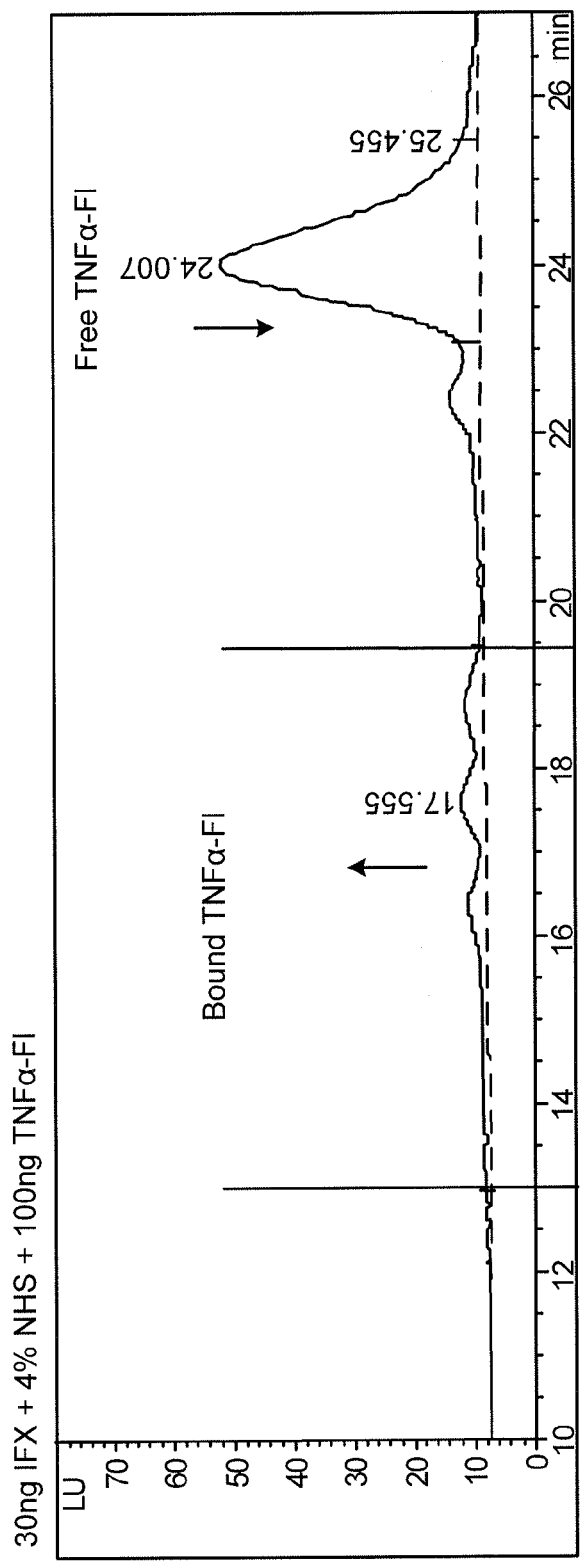

FIGS. 11A-11D show the separation of the HACA bound IFX-Fl complex from the free IFX-Fl due to the mobility shift of the high molecular weight complex. As seen in panels 11C and 11D, the retention time of the fluorescent peak shifted from 21.8 min to 15.5-19.0 min. The more the HACA is present in the reaction mixture, the less the free IFX-Fl remains in the chromatogram and the more the immuno-complex is formed. FIGS. 12A-12B show the dose-response curves of the fluorescent peak shift caused by the addition of HACA. Using the HACA positive sample, we could detect the peak shift with 1:1000 dilutions of the serum.

Figure 14A:
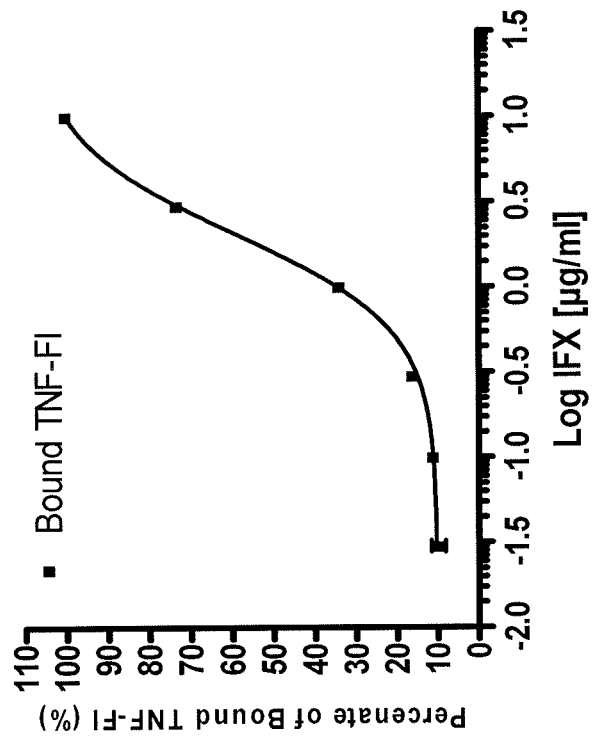
FIGS. 14A-14B show dose-response curves of the bound (14B) and free (14A) TNFα generated with increasing dilutions of IFX-spiked serum as determined by the mobility shift assay. Increasing concentrations of IFX added to the incubation mixture decreases the percentage of free TNFα while increasing the percentage of bound TNFα.
Figure 14B:
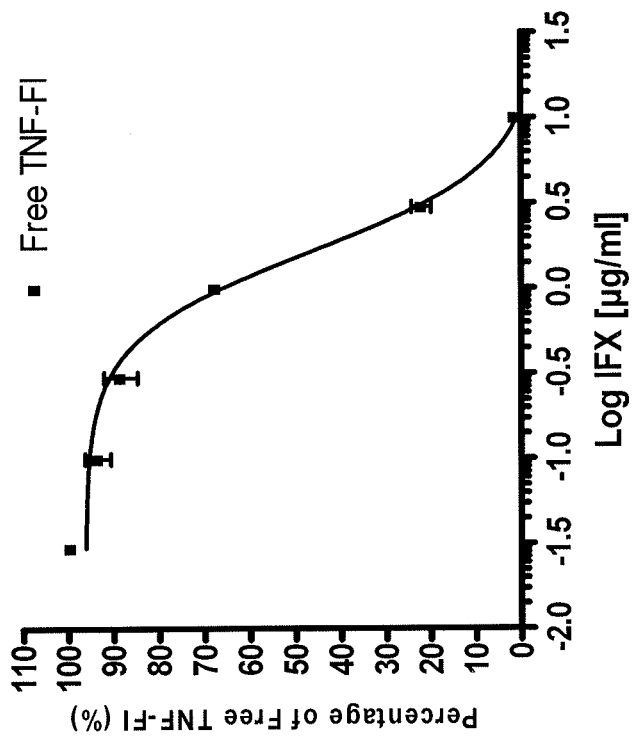

FIGS. 13A-13D show the separation of the IFX bound TNFα-Fl complex from the free TNFα-Fl due to the mobility shift of the high molecular weight complex. As seen in panels 13C and 13D, the retention time of the fluorescent peak shifted from 24 min to 13-19.5 min. The more the IFX is present in the reaction mixture, the less the free TNFα-Fl remains in the chromatogram and the more the immuno-complex is formed. FIGS. 14A-14B show the dose-response curves of the TNFα-Fl peak shift caused by the addition of IFX. Based on the added IFX, the detection limit is 10 ng/mL of IFX in serum.

The novel mobility shift assay of the present invention was validated by testing serum samples from HACA positive and negative patients measured by the Bridge assay (Table 2). Using this assay, we have analyzed serum samples from 50 healthy subjects and 117 IBD patients treated with IFX. All 50 healthy subject samples have an IFX level below the limit of detection, whereas 65 of the patient samples have an average IFX concentration of 11.0 μg/ml. Table 3 shows the HACA levels in the serum of healthy controls and IBD patients treated with IFX measured by the Bridge assay and the mobility shift assay. The Bridge assay detected less HACA-positive patients than the mobility shift assay and more false negatives as well as more false positives.

TABLE 2

Correlation of Relative HACA Levels in Patient Serum from Strong Positive and Negative on Bridge Assay to SE-HPLC Assay.

|  | Bridge assay | HPLC shift assay | Correlation |
|---|---|---|---|
| Positive | 82 | 81 | 99% |
| Negative | 12 | 12 | 100% |

TABLE 3

Patient Sample Analysis on Serum Levels of HACA with Bridge Assay (Cut Off 1.69 μg/ml) and HPLC Shift Assay (Cut Off 0.19, Ratio of Bound and Free IFX).

|  |  | HACA Positive | | Bridge Assay | |
|---|---|---|---|---|---|
|  | Subjects (n) | Bridge Assay | HPLC Assay | False Negative | False Positive |
| Healthy Control | 50 | N/A | 0 | N/A | N/A |
| Patient treated with IFX | 117 | 24 (20.5%) | 33 (28.2%) | 9 (High IFX) | 9 |

False negative results are caused by patient serum containing high levels of IFX which interferes with the Bridge assay on HACA determination while the SE-HPLC assay is not affected. False positive results are caused by patient serum containing high levels of non-specific interference substance which may interfere with the Bridge assay.

Figure 15B:
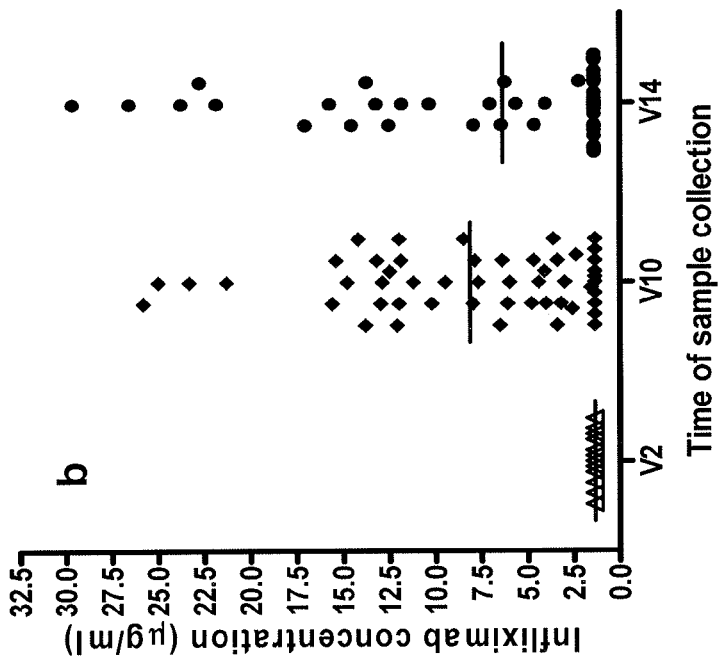
FIGS. 15A-15B show the measurement of relative HACA level (15A) and IFX concentration (15B) in inflammatory bowel disease (IBD) patients treated with IFX at different time points by the mobility shift assay.
Figure 15A:
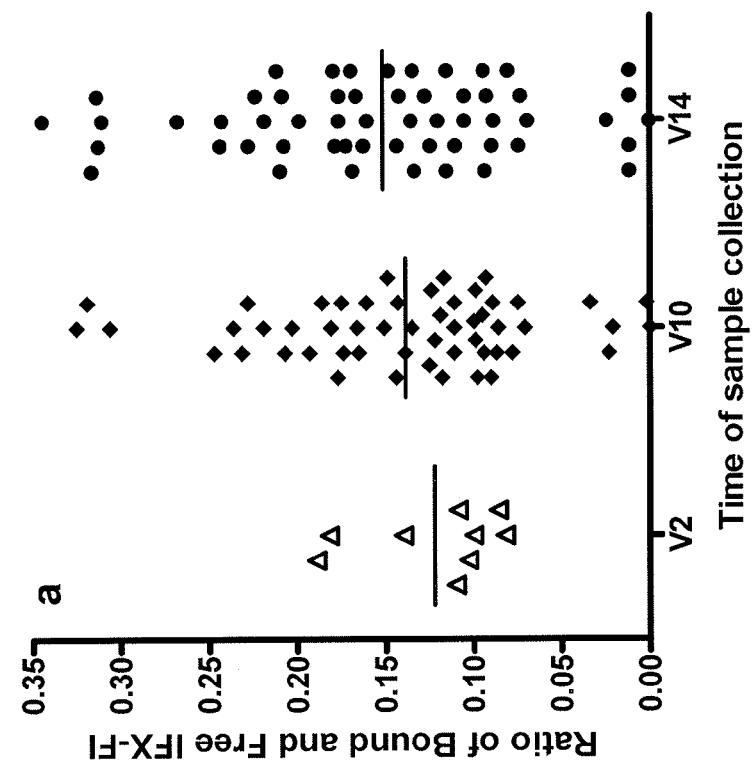

FIGS. 15A-15B show the relationship of the HACA level and IFX concentration in IBD patients during the course of IFX treatment. HACA could be detected as early as V10 (30 Weeks) and continued to increase in some patients during IFX treatment. FIGS. 16A-16C show that HACA can be detected in the presence of IFX using the assay of the present invention. A higher level of HACA in the serum was associated with a lower level of IFX that could be detected (e.g., reduced the bioavailability). As such, early detection of HACA while on treatment with IFX can guide the physician and/or patient to switch to other anti-TNF drugs or increase the dose of IFX.

The assays were validated in terms of intra- and inter-assay precision (based on the CV parameter) and susceptibility to interference agents. This analysis is presented in the following tables:

| Infliximab assay | |
|---|---|
| Parameter | CV % |
| Intra-assay Precision | 2.89 |
| Inter-assay Precision | |
| Run to Run | 4.57 |
| Analyst to Analyst | 6.06 |
| Instrument to Instrument | 2.73 |

| HACA assay | |
|---|---|
| Parameter | CV % |
| Intra-assay Precision | 3.96 |
| Inter-assay Precision | |
| Run to Run | 4.15 |
| Analyst to Analyst | 5.84 |
| Instrument to Instrument | 6.88 |

| Infliximab assay | | | |
|---|---|---|---|
| Interference Agent | Typical Range | Concentration tested | Interference |
| IgG, IgA, IgM | 0.4-16 mg/mL | 10, 2.0, 1.5 mg/mL | NA |
| ATI | 3.71-150 U/ml (0-60 μg/mL) | 100 U/mL (~55 μg/mL) | Interferes with detection of low concentration IFX samples (<5 μg/mL) |
| Rheumatoid Factor | >30 IU/mL (RA positive patients) | Up to 387 IU/mL | NA |
| TNF-α | 6.2-6.6 pg/mL | 0.0125 ng/mL-40 μg/mL | 100 ng/mL |
| TNFR1/TNFR2 | 1.9/4.5 ng/mL | 0.1-1000 ng/mL | NA |
| Hemolyzed Serum | >20 HI | 100-300 HI | NA |

The following agents were also tested and did not show interference: Azathioprine, Methotrexate, TNF-β, Lipemic serum, Hemoglobin

| HACA assay | | | |
|---|---|---|---|
| Interference Agent | Typical Range | Concentration tested | Interference |
| IgG, IgA, IgM | 0.4-16 mg/mL | 10, 2.0, 1.5 mg/mL | NA |
| Infliximab | 0-100 μg/mL | 0.78-100 μg/mL | NA |
| Rheumatoid Factor | >30 IU/mL (RA positive patients) | Up to 774 IU/mL | NA |
| TNF-α | 6.2-6.6 pg/mL | 0.0125 ng/mL-40 μg/mL | 250 ng/mL |
| TNFR1/TNFR2 | 1.9/4.5 ng/mL | 0.1-1000 ng/mL | NA |
| Hemolyzed Serum | >20 HI | 100-300 HI | NA |

The following agents were also tested and did not show interference: Azathioprine, Methotrexate, TNF-β, Lipemic serum, Hemoglobin Conclusion Anti-TNFα biologic drugs can be readily labeled with a fluorophore ("Fl") and the mobility shift assay format used for measuring HACA/HAHA is a homogeneous assay without the coating of antigens to a solid surface and multiple washing and incubation steps like a typical ELISA. Incubation of Fl-labeled IFX with HACA-positive serum results in the formation of an immune complex which elutes at a different position compared to free Fl-labeled IFX in SE-HPLC and thus the amount of HACA can be quantitated. The presence of other serum components has little effect on the mobility shift assay. The mobility shift assay format, unlike ELISA, is not affected by non-specific binding of irrelevant IgGs and detects the IgG4 isotype. Healthy serum samples do not cause mobility shift of the Fl-labeled IFX and 28.2% of the patients treated with IFX were found to have HACA by the assay of the present invention. As such, the assay format described herein is very sensitive and can be applied to detect all biologic drugs (e.g., Remicade, Humira, Enbrel and Cimzia) as well as their antibodies (e.g., anti-Remicade, anti-Humira, anti-Enbrel and anti-Cimzia) in patient serum. Notably, since HACA can be detected in the presence of IFX using the mobility shift assay of the invention, early detection of HACA while on treatment with IFX can guide the physician and/or patient to switch to other anti-TNF drugs or increase the subsequent dose of IFX.

We have developed a novel non-radiolabeled, liquid-phase, SE-HPLC assay to measure the IFX and HACA levels in serum samples obtained from patients treated with IFX. The novel assay has high sensitivity, accuracy, and precision, and the results are highly reproducible, which makes this assay suitable for routine testing of a large number of human serum samples. The new assay format, unlike ELISA, eliminates coating of antigens to solid surfaces and is not affected by non-specific binding of irrelevant IgGs. These advantages of the assay format described herein reduce the false negative and false positive results of the test. Advantageously, the assay format of the present invention is very sensitive and can be used to detect all biologic drugs as well as their antibodies present in the serum while the patient is on therapy.

Example 4

Differentiation Between Neutralizing and Non-Neutralizing Human Anti-Chimeric Antibodies (HACA) in Patient Serum Using Novel Mobility Shift Assays This example illustrates novel homogeneous assays for measuring autoantibody (e.g., HACA) concentrations in a patient sample (e.g., serum) and for determining whether such autoantibodies are neutralizing or non-neutralizing autoantibodies using size exclusion chromatography to detect the binding of these autoantibodies to fluorescently labeled anti-TNFα drug in the presence of fluorescently labeled TNFα. These assays are advantageous because they obviate the need for wash steps which remove low affinity HACA, use distinct fluorophores that allow for detection on the visible and/or IR spectra which decreases background and serum interference issues, increase the ability to detect neutralizing or non-neutralizing HACA in patients with a low titer due to the high sensitivity of fluorescent label detection, and occur as a liquid phase reaction, thereby reducing the chance of any changes in the epitope by attachment to a solid surface such as an ELISA plate.

Figure 17A:
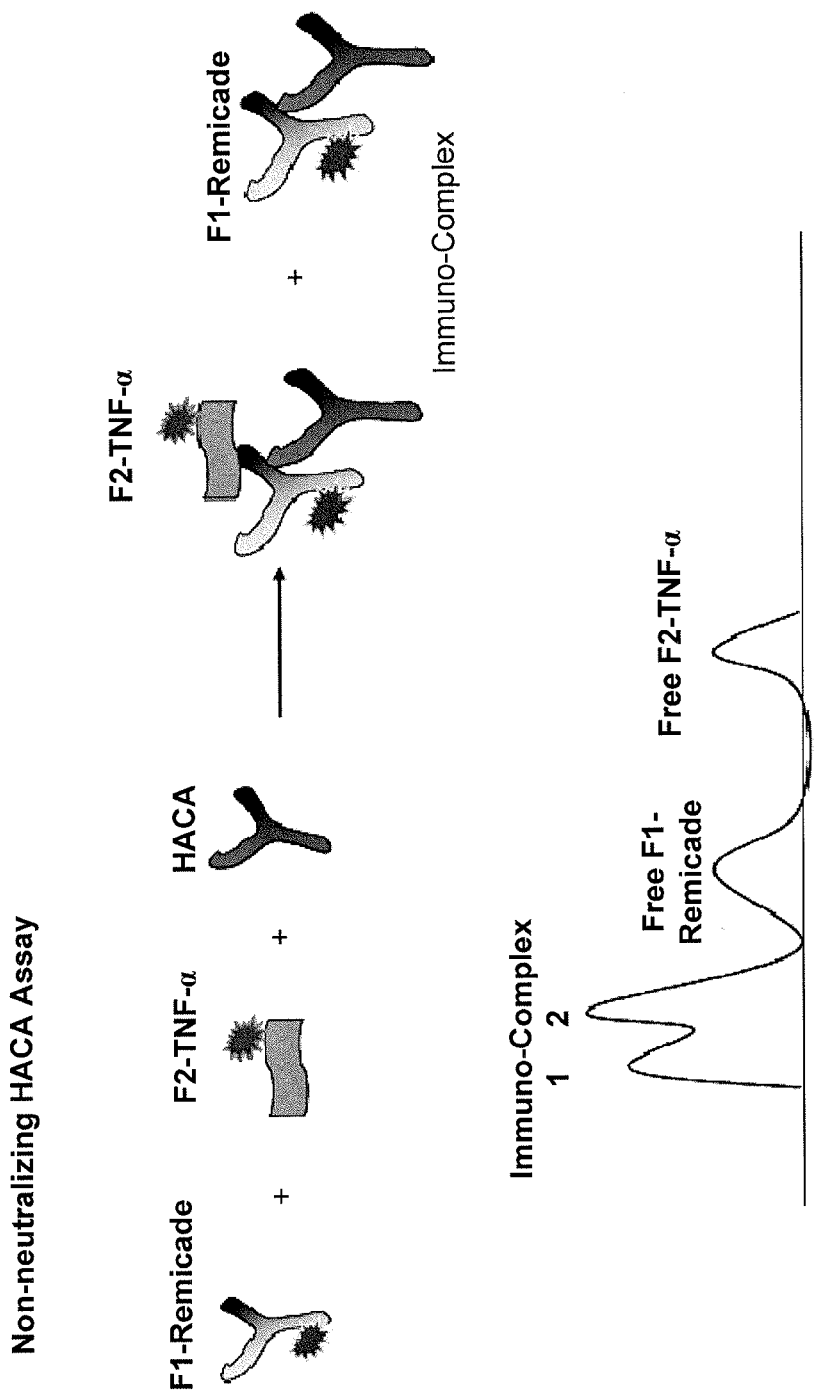
FIGS. 17A-17B show exemplary embodiments of the assays of the present invention to detect the presence of (17A) non-neutralizing or (17B) neutralizing autoantibodies such as HACA.
Figure 17B:
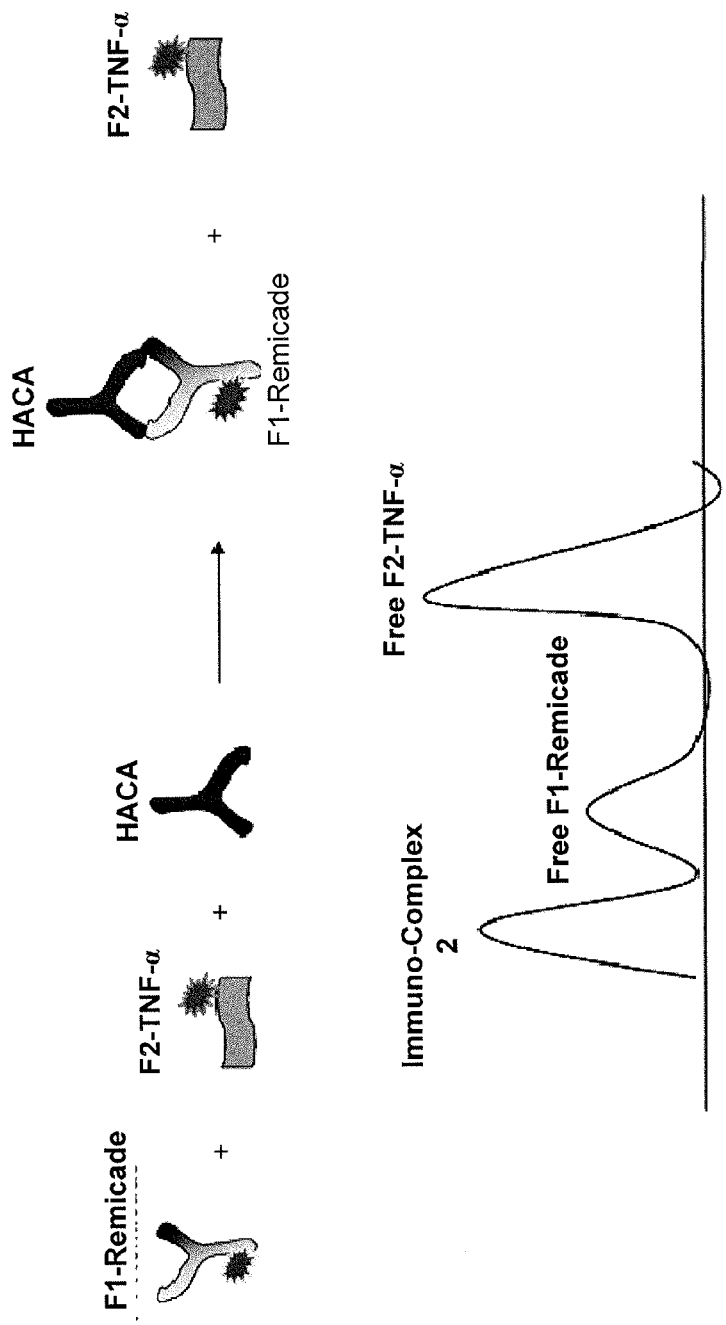

In one exemplary embodiment, an anti-TNFα drug (e.g., REMICADE™) is labeled with a fluorophore "F1" (see, e.g., FIG. 17A), wherein the fluorophore can be detected on either or both the visible and IR spectra. Similarly, TNFα is labeled with a fluorophore "F2" (see, e.g., FIG. 17A), wherein the fluorophore can also be detected on either or both the visible and IR spectra, and wherein "F1" and "F2" are different fluorophores. The labeled anti-TNFα drug is incubated with human serum in a liquid phase reaction and the labeled TNFα is added to the reaction to allow the formation of complexes (i.e., immuno-complexes) between the labeled anti-TNFα drug, labeled TNFα, and/or HACA present in the serum. Following incubation, the samples are loaded directly onto a size exclusion column. Binding of both the autoantibody (e.g., HACA) and the labeled TNFα to the labeled anti-TNFα drug results in a leftward shift of the peak (e.g., "Immuno-Complex 1" in FIG. 17A) compared to a binary complex between the autoantibody and the labeled anti-TNFα drug (e.g., "Immuno-Complex 2" in FIG. 17A), the labeled drug alone, or the labeled TNFα alone. The presence of this ternary complex of autoantibody (e.g., HACA), labeled TNFα, and labeled anti-TNFα drug indicates that the autoantibody present in the serum sample is a non-neutralizing form of the autoantibody (e.g., HACA), such that the autoantibody does not interfere with the binding between the anti-TNFα antibody and TNFα. In one particular embodiment, as shown in FIG. 17A, if non-neutralizing HACA is present in the serum, a shift will be observed for both F1-REMICADE™ and F2-TNFα, resulting in an increase in both the Immuno-Complex 1 and Immuno-Complex 2 peaks and a decrease in the free F1-REMICADE™ and free F2-TNFα peaks. However, the presence of the binary complex between the autoantibody (e.g., HACA) and the labeled anti-TNFα drug (e.g., "Immuno-Complex 2" in FIG. 17B) in the absence of the ternary complex of autoantibody (e.g., HACA), labeled TNFα, and labeled anti-TNFα drug indicates that the autoantibody present in the serum sample is a neutralizing form of the autoantibody (e.g., HACA), such that the autoantibody interferes with the binding between the anti-TNFα antibody and TNFα. In one particular embodiment, as shown in FIG. 17B, if neutralizing HACA is present in the serum, a shift will be observed for F1-REMICADE™, resulting in an increase in the Immuno-Complex 2 peak, a decrease in the free F1-REMICADE™ peak, and no change in the free F2-TNFα peak. In certain instances, the presence of neutralizing HACA indicates that the current therapy with REMICADE™ should be switched to another anti-TNFα drug such as HUMIRA™.

Figure 18:
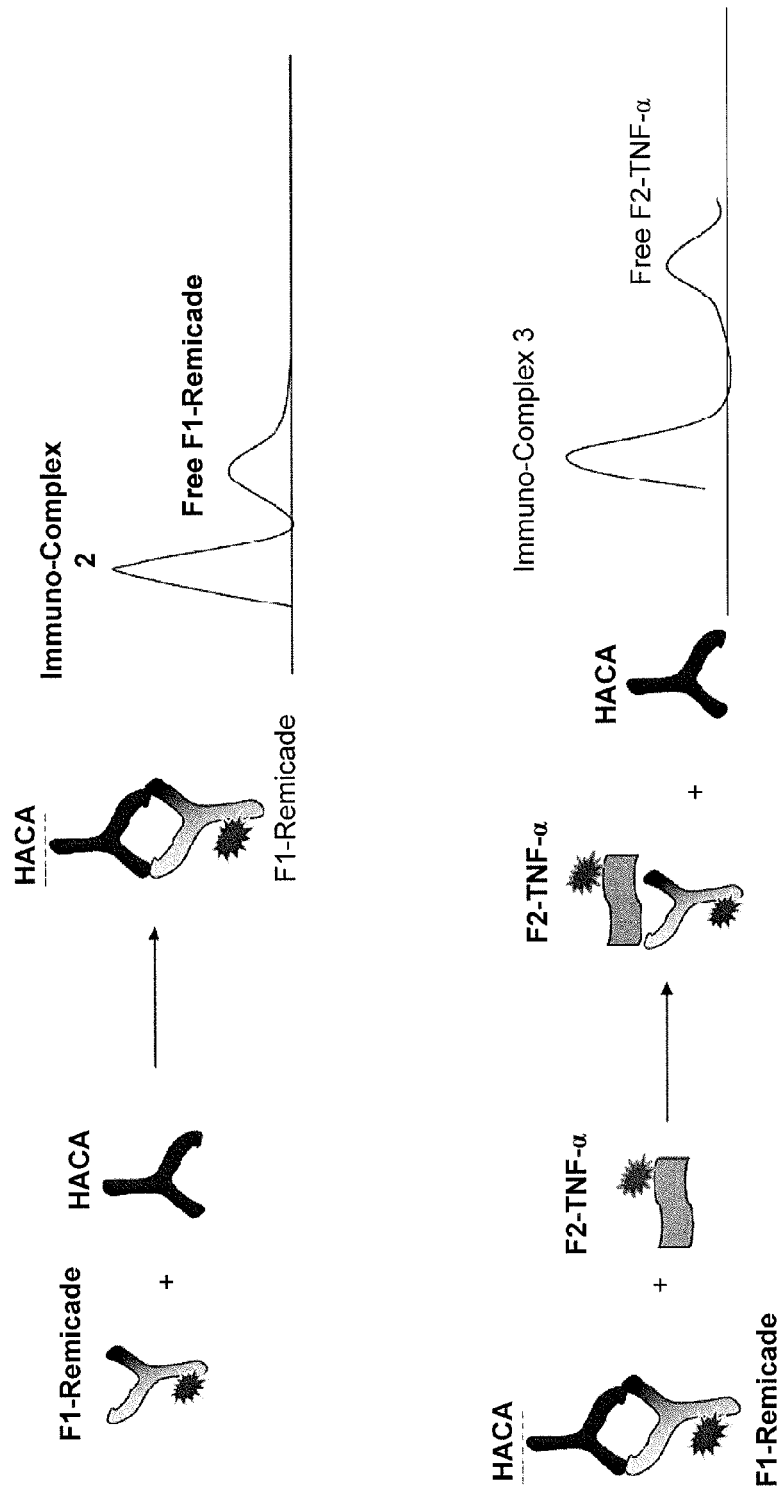
FIG. 18 shows an alternative embodiment of the assays of the present invention to detect the presence of neutralizing autoantibodies such as HACA.
Figure 19A:
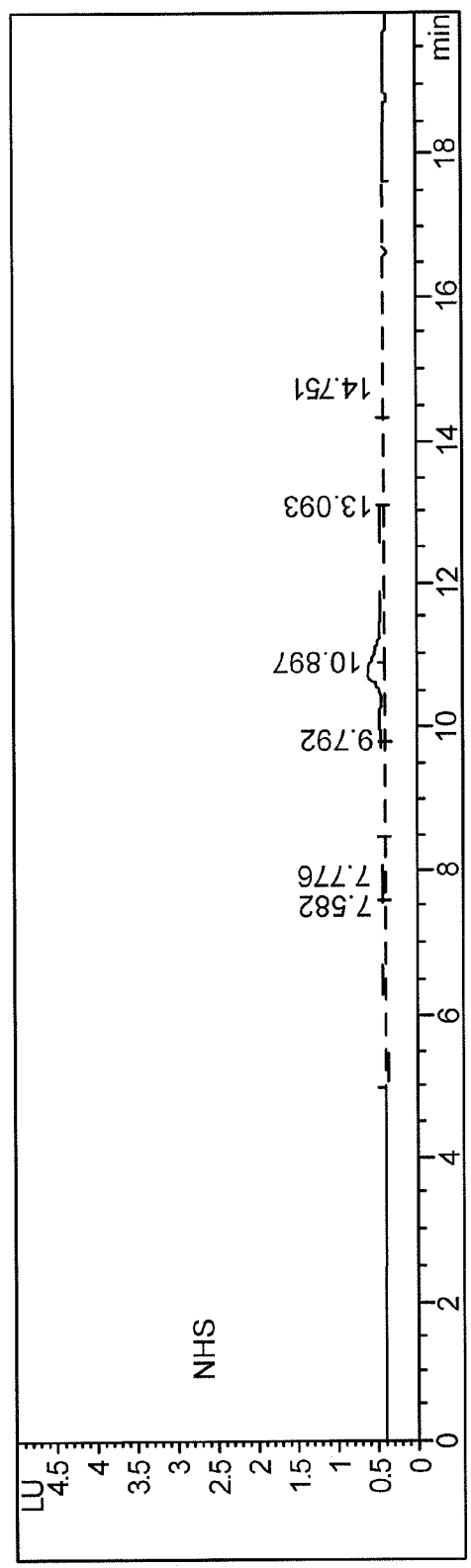
FIGS. 19A-19H show mobility shift profiles of Fl-labeled adalimumab (ADL) incubated with normal human serum (NHS) in the presence of different amounts of anti-human IgG. The addition of increasing amounts of anti-human IgG to the incubation mixture dose-dependently shifted the free Fl-ADL peak (FA) to the higher molecular mass eluting positions, C1 and C2, while the internal control (IC) did not change.
Figure 19B:
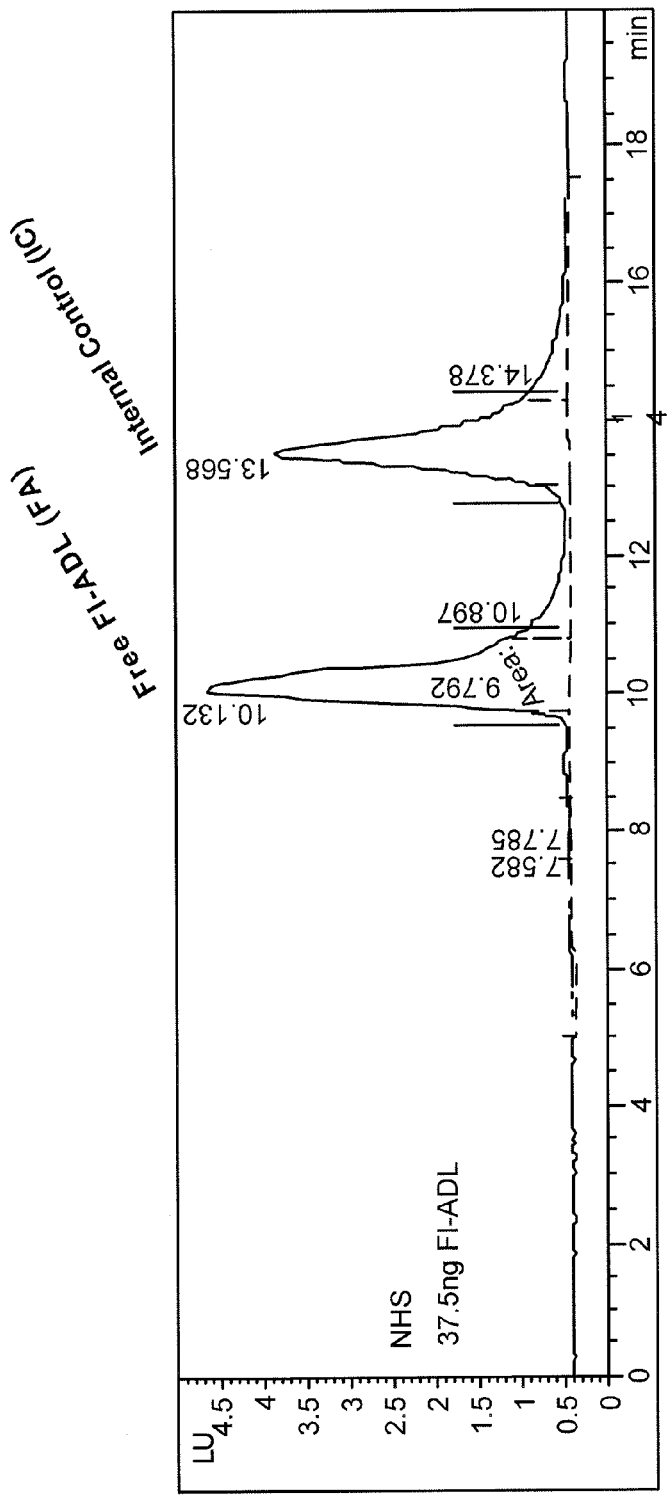
Figure 19C:
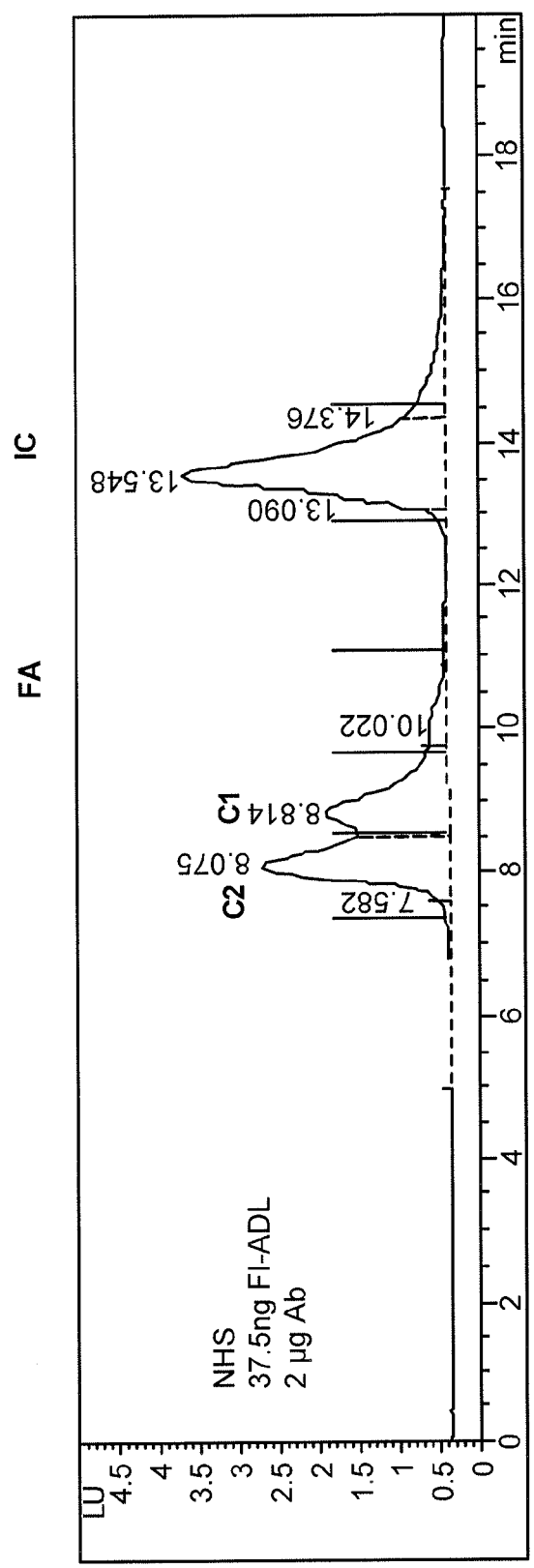
Figure 19D:
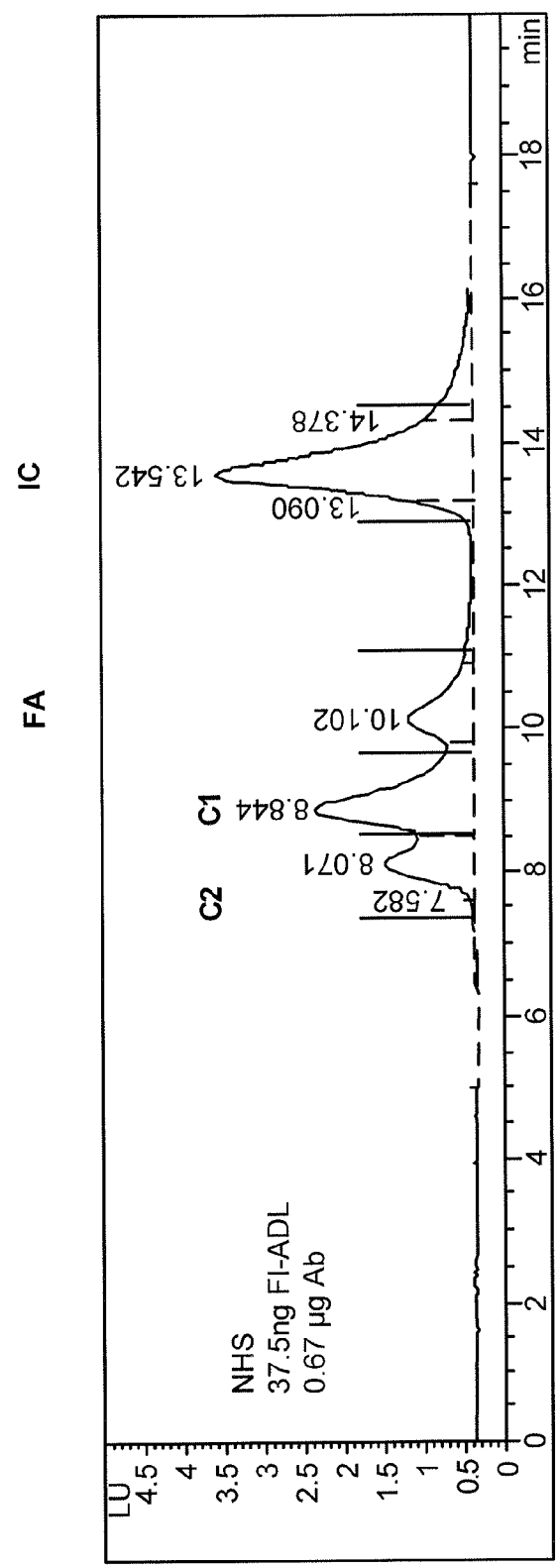
Figure 19E:
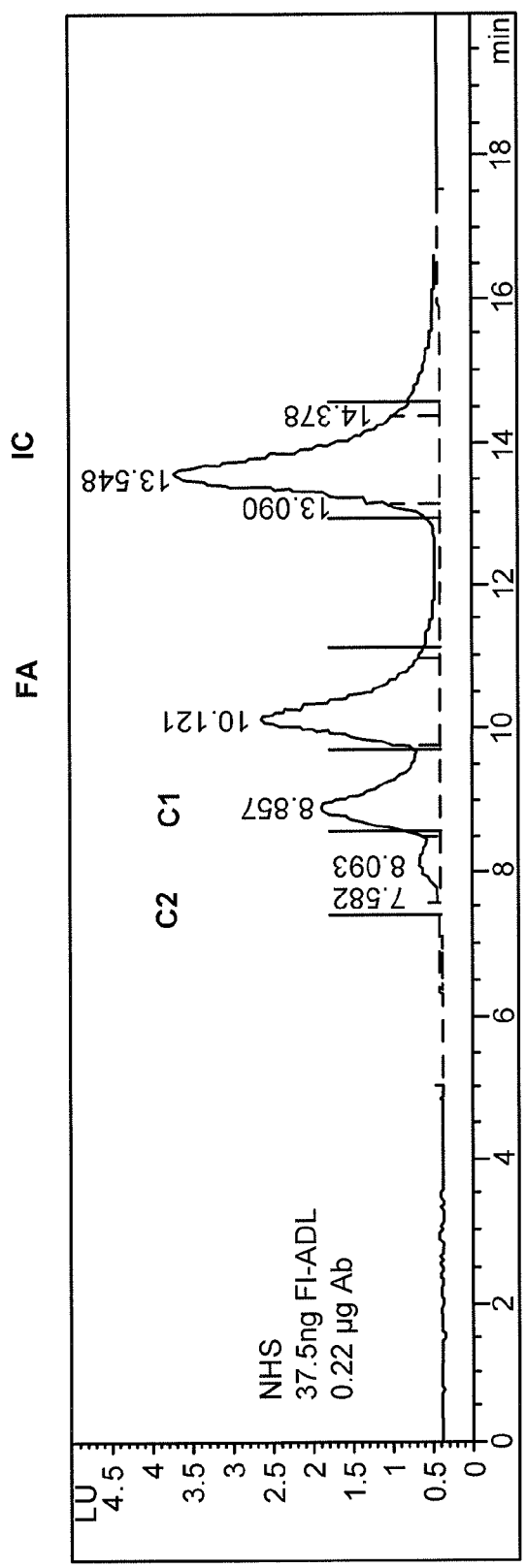
Figure 19F:
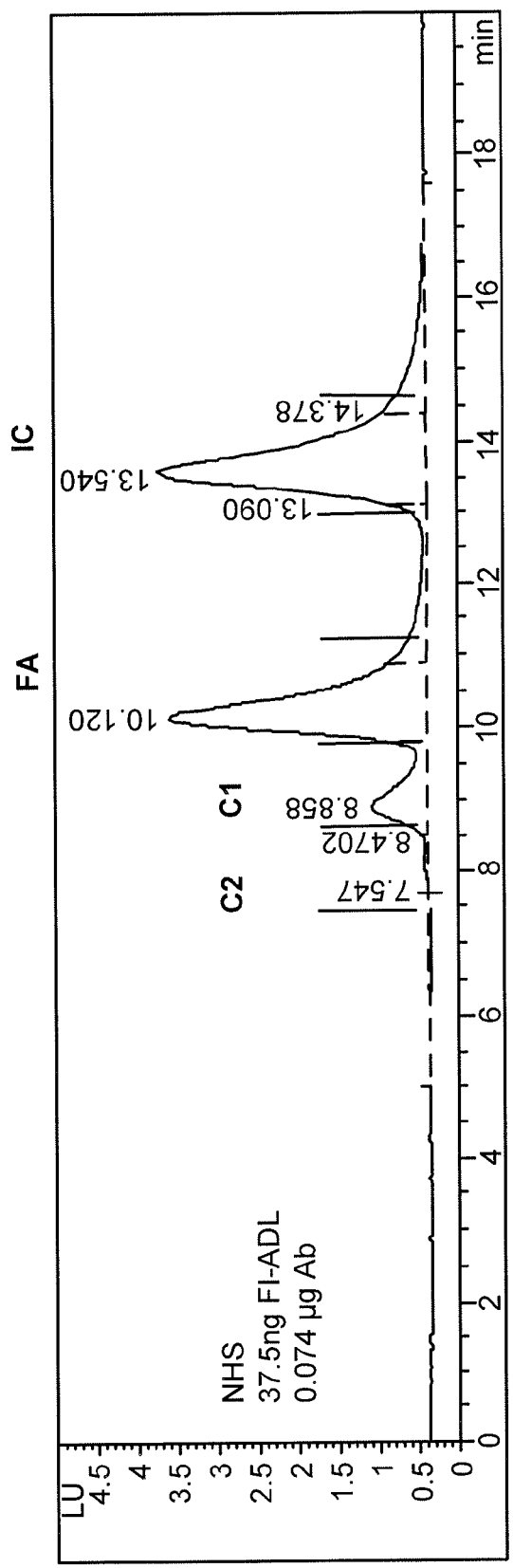
Figure 19G:
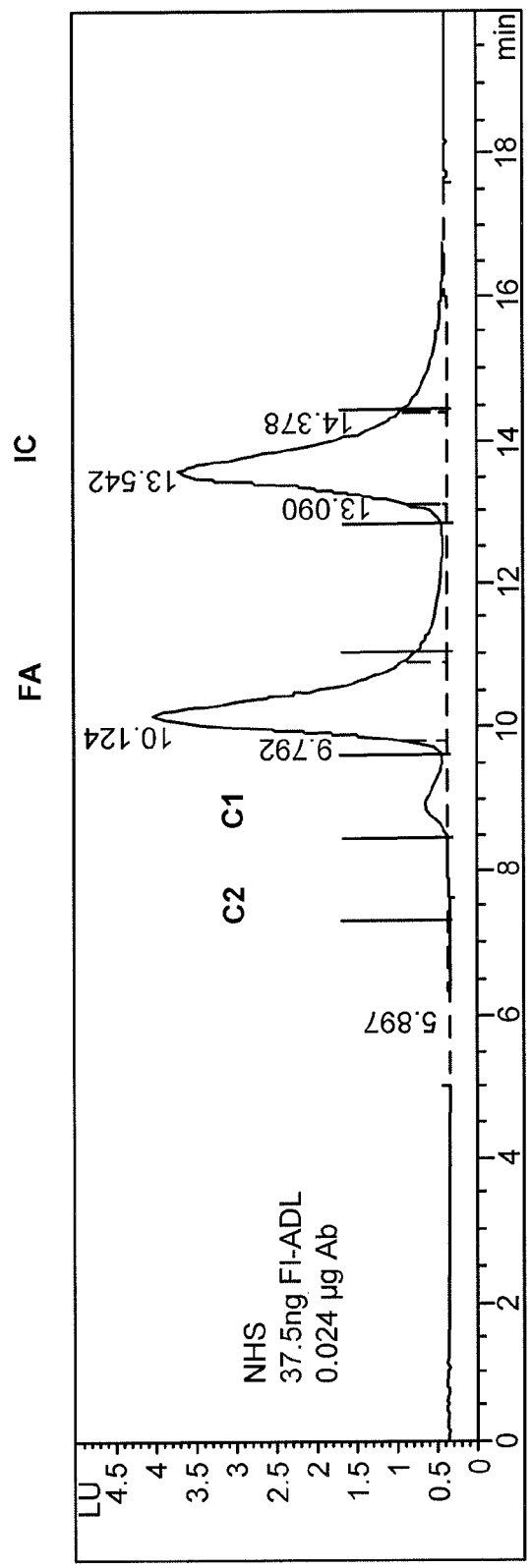
Figure 19H:
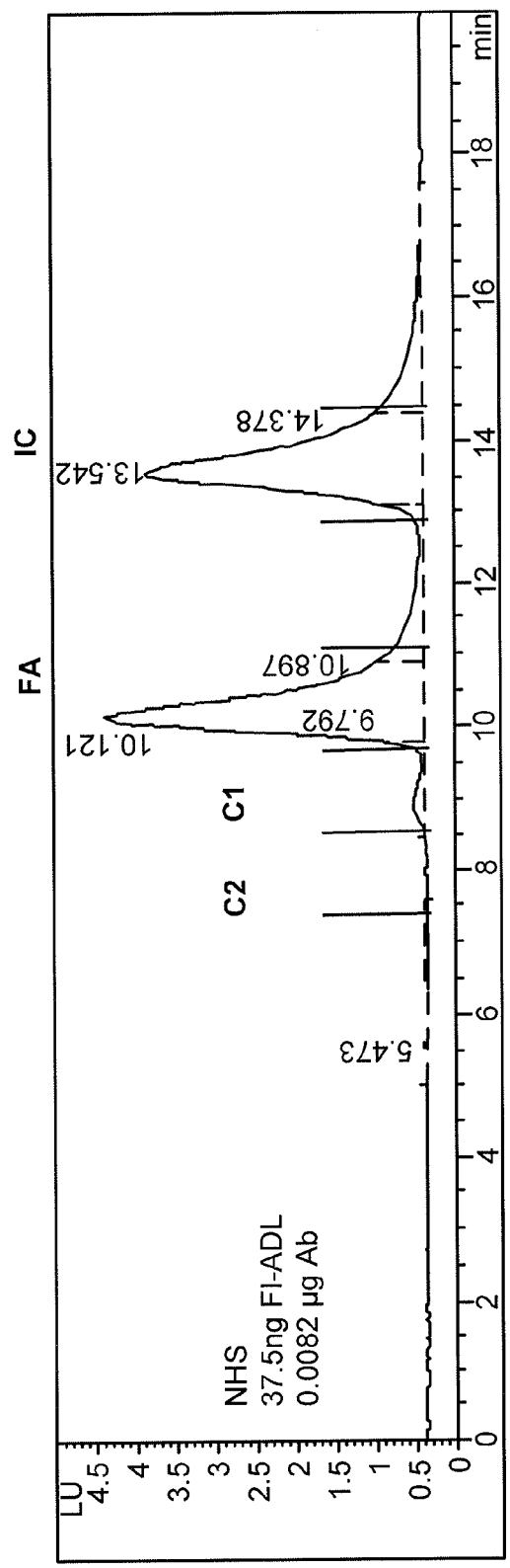

In an alternative embodiment, the labeled anti-TNFα drug is first incubated with human serum in a liquid phase reaction to allow the formation of complexes (i.e., immuno-complexes) between the labeled anti-TNFα drug and HACA present in the serum. Following incubation, the samples are loaded directly onto a first size exclusion column. Binding of the autoantibody (e.g., HACA) to the labeled anti-TNFα drug results in a leftward shift of the peak (e.g., "Immuno-Complex 2" in FIG. 18) compared to the labeled drug alone. The labeled TNFα is then added to the reaction to determine whether it is capable of displacing (e.g., competing with) the autoantibody (e.g., HACA) for binding to the labeled anti-TNFα drug, to thereby allow the formation of complexes (i.e., immuno-complexes) between the labeled anti-TNFα drug and the labeled TNFα. Following incubation, the samples are loaded directly onto a second size exclusion column. Binding of the labeled anti-TNFα drug to the labeled TNFα results in a leftward shift of the peak (e.g., "Immuno-Complex 3" in FIG. 18) compared to the labeled TNFα alone. Disruption of the binding between the autoantibody (e.g., HACA) and the labeled anti-TNFα drug by the addition of the labeled TNFα indicates that the autoantibody present in the serum sample is a neutralizing form of the autoantibody (e.g., HACA), such that the autoantibody interferes with the binding between the anti-TNFα antibody and TNFα. In certain instances, the presence of neutralizing HACA indicates that the current therapy with REMICADE™ should be switched to another anti-TNFα drug such as HUMIRA™.

Example 5

Analysis of Human Anti-Drug Antibodies (ADA) to Adalimumab in Patient Serum Using a Novel Homogeneous Mobility Shift Assay Background and Aim: Monoclonal antibodies against TNF-α such as infliximab (IFX), adalimumab (HUMIRA™), and certolizumab have been shown to be effective in treating inflammatory bowel disease (IBD) and other inflammatory disorders. Anti-drug antibodies (ADA) may reduce the drug's efficacy and/or induce adverse effects. However, ADAs have been found not only in patients treated with the chimeric antibody infliximab, but also in patients treated with the humanized antibody adalimumab. Monitoring of ADA and drug levels in individual patients may help optimize treatment and dosing of the patient. We have developed a non-radio labeled liquid-phase homogeneous mobility shift assay to accurately measure in the serum both HACA (Human Anti-Chimeric Antibody) and IFX from patients. This assay method overcomes a major limitation of the current solid-phase assays for detecting HACA, namely the inability to accurately detect HACA in the presence of IFX in circulation. In the present study, we have evaluated this new method for measuring serum ADA and drug levels in patients treated with the humanized antibody drug, adalimumab.

Methods: The mobility shift assay was based on the shift in retention time of a free antigen versus antigen-antibody immunocomplex on size-exclusion separation. Fluorophore-labeled adalimumab or TNF-α and internal control were mixed with serum samples to measure the mobility shift of free adalimumab and TNF-α in the presence of ADA or drug. The changes in the ratio of free adalimumab or TNF-α to internal control are indicators of immunocomplex formation. Serum concentrations of ADA or adalimumab were determined with standard curves generated by incubating with different concentrations of anti-human IgG antibody or purified adalimumab. Using the mobility shift assay, we measured adalimumab and ADA levels in sera collected from IBD patients treated with adalimumab who had lost response.

Results: Dose-response curves were generated with anti-human IgG antibody for the measurement of mobility shift of labeled adalimumab. The detection limit of the assay was 1 ng of anti-human IgG. Sera from fifty healthy controls were tested for ADA and all of the samples had ADA levels below the detection limit (i.e., no shift of the free labeled-adalimumab). Detection of ADA was also demonstrated in the presence of exogenously added adalimumab. To measure the drug concentration in patients treated with adalimumab, we generated a standard curve with different amounts of adalimumab on the mobility shift of labeled TNF-α, and the detection limit of adalimumab was 10 ng.

Conclusions: The non-radio labeled liquid-phase homogeneous mobility shift assay of the present invention has been applied to measure ADA and adalimumab levels in serum samples from patients treated with adalimumab. The assay is found to be reproducible with high sensitivity and accuracy, and can be used to evaluate ADA levels in serum samples from patients treated with adalimumab.

Example 6

Analysis of Anti-Drug Antibodies (ADA) to Adalimumab in Patient Serum Using a Novel Proprietary Mobility Shift Assay Abstract Background: Anti-TNF-α drugs such as infliximab (IFX) and adalimumab (ADL) have been shown to be effective in treating inflammatory bowel disease (IBD). However, induction of ADA in the treated patients may reduce the drug's efficacy and/or induce adverse effects. Indeed, ADAs have been found not only in patients treated with IFX, but also in patients treated with ADL. Monitoring of ADA and drug levels in individual patients may help to optimize treatment and dosing of the patient. We have developed a proprietary mobility shift assay to accurately measure in the serum both HACA (Human Anti-Chimeric Antibody) and IFX from IFX-treated patients. This assay overcomes the major limitation of the current solid-phase assays for detecting HACA, namely the inability to accurately detect HACA in the presence of IFX in circulation. In the present study, we have evaluated this new assay to measure serum ADA and drug levels in patients treated with the fully human antibody drug, ADL.

Methods: The mobility shift assay was based on the shift in retention time of the antigen-antibody immunocomplex versus free antigen on size-exclusion chromatography. Fluorophore-labeled ADL or TNF-α and internal control were mixed with serum samples to measure the mobility shift of labeled ADL and TNF-α in the presence of ADA or drug. The changes in the ratio of free ADL or TNF-α to internal control are the indicators of the immunocomplex formation. Serum concentrations of ADA or ADL were determined with standard curves generated by incubating with different concentrations of anti-human IgG antibody or purified ADL. Using this assay, we measured ADL and ADA levels in sera collected from IBD patients treated with ADL.

Results: Dose-response curves were generated with anti-human IgG antibody for the measurement of mobility shift of labeled ADL. The detection limit of the assay was 10 ng of anti-human IgG. Sera from 100 healthy controls were tested for the ADA and all of the samples had an ADA level below detection limit (no shift of free labeled ADL). Detection of ADA was demonstrated in five out of 114 IBD patient samples treated with ADL. To measure the drug concentration in patients treated with ADL, we generated a standard curve with different amounts of ADL on the shift of labeled TNF-α with the detection limit of 10 ng.

Conclusions: We have applied our proprietary non-radio labeled liquid-phase homogeneous mobility shift assay to measure the ADA and ADL levels in serum from patients treated with ADL. The assays are reproducible with high sensitivity and accuracy, and are useful for evaluating ADA levels in serum samples from patients treated with ADL.

Introduction

Anti-tumor necrosis factor-alpha (TNF-α) biologics such as infliximab (IFX), etanercept, adalimumab (ADL) and certolizumab pegol have been shown to reduce disease activity in a number of autoimmune diseases, including Crohn's Disease (CD) and rheumatoid arthritis (RA). However, some patients do not respond to anti-TNF-α therapy, while others need higher or more frequent dosage due to lack of sufficient response, or develop infusion reactions.

Immunogenicity of therapeutic antibodies which causes the patients to develop antibodies against the drugs may contribute to the failure of the treatments and infusion reactions. Chimeric antibodies like IFX have a higher potential of inducing antibody generation compared to fully humanized antibodies such as ADL. The prevalence of antibodies to IFX (HACA) in RA patients varies from 12% to 44% and seems to be inversely proportional to the level of IFX in patient serum and therapeutic response. While the fully humanized ADL is supposed to be less immunogenic than murine or chimeric antibodies, several studies have reported the formation of human anti-humanized antibodies (HAHA) and showed the prevalence of antibody generation from 1% to 87% in RA and CD patients (Aikawa et al., Immunogenicity of Anti-TNF-alpha agents in autoimmune diseases. *Clin. Rev. Allergy Immunol.*, 38(2-3):82-9 (2010)).

Many patients with secondary response failure to one anti-TNF-α drug may benefit from switching to another anti-TNF-α drug or increasing dosage and/or dosing frequency. Monitoring of patients for drug and anti-drug antibody (ADA) levels is therefore warranted so that drug administration can be tailored to the individual patient. This approach allows dose adjustment when warranted or cessation of medication when ADA levels are present. (Bendtzen et al., Individual medicine in inflammatory bowel disease: monitoring bioavailability, pharmacokinetics and immunogenicity of anti-tumour necrosis factor-alpha antibodies. *Scand. J. Gastroenterol.*, 44(7):774-81 (2009); Afif et al., Clinical utility of measuring infliximab and human anti-chimeric antibody concentrations in patients with inflammatory bowel disease. *Am. J. Gastroenterol.*, 105(5):1133-9 (2010)).

A number of assays have been developed to measure HACA and HAHA. One of the limitations of the current methodologies is that ADA levels cannot be reliably measured when there is a high level of drugs in the circulation.

We have developed a proprietary non-radiolabeled, liquid-phase, mobility shift assay to measure the ADA and ADL levels in serum from patients treated with ADL which is not affected by the presence of the drug in the serum.

Methods

Fluorophore (Fl)-labeled ADL was incubated with patient serum to form the immunocomplex. A Fl-labeled small peptide was included as an internal control in each reaction. Different amounts of anti-human IgG were used to generate a standard curve to determine the serum ADA level. Free Fl-labeled ADL was separated from the antibody bound complex based on its molecular weight by size-exclusion chromatography. The ratio of free Fl-labeled ADL to internal control from each sample was used to extrapolate the HAHA concentration from the standard curve. A similar methodology was used to measure ADL levels in patient serum samples with Fl-labeled TNF-α.

Results

FIGS. 19A-19H show the separation of the anti-human IgG bound Fl-ADL complex from the free Fl-ADL due to the mobility shift of the high molecular weight complex. As seen in panels 19C to 19H, the retention time of the fluorescent peak shifted from 10.1 min to 7.3-9.5 min. The more the anti-human IgG is added in the reaction mixture, the less the free ADL remains in the chromatogram and the more the immunocomplex is formed (h to c). The retention time for the internal control is 13.5 min.

Figure 20:
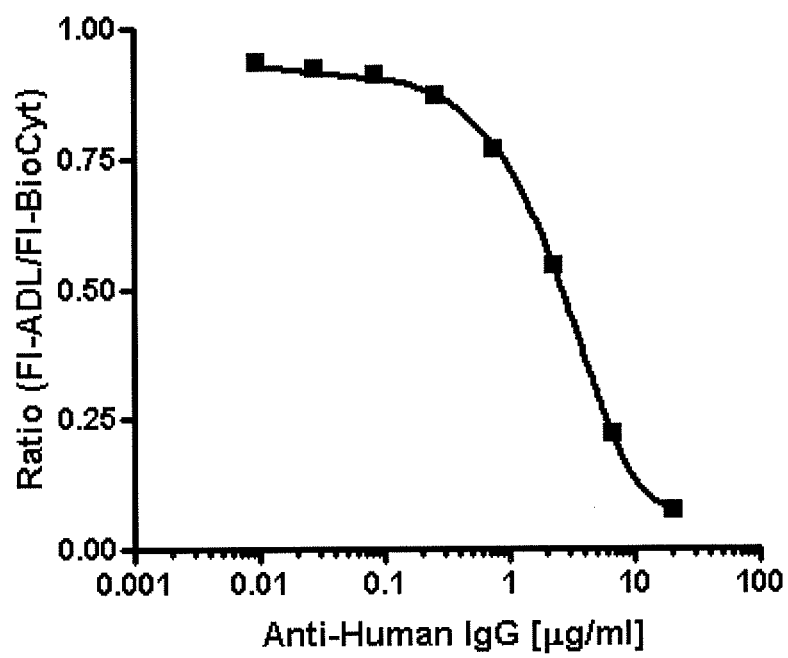
FIG. 20 shows a dose-response curve of anti-human IgG on the shift of free Fl-ADL. Increasing amounts of anti-human IgG were incubated with 37.5 ng of Fl-ADL and internal control. The more the antibody was added to the reaction mixture the lower the ratio of free Fl-ADL to internal control.
Figure 21A:
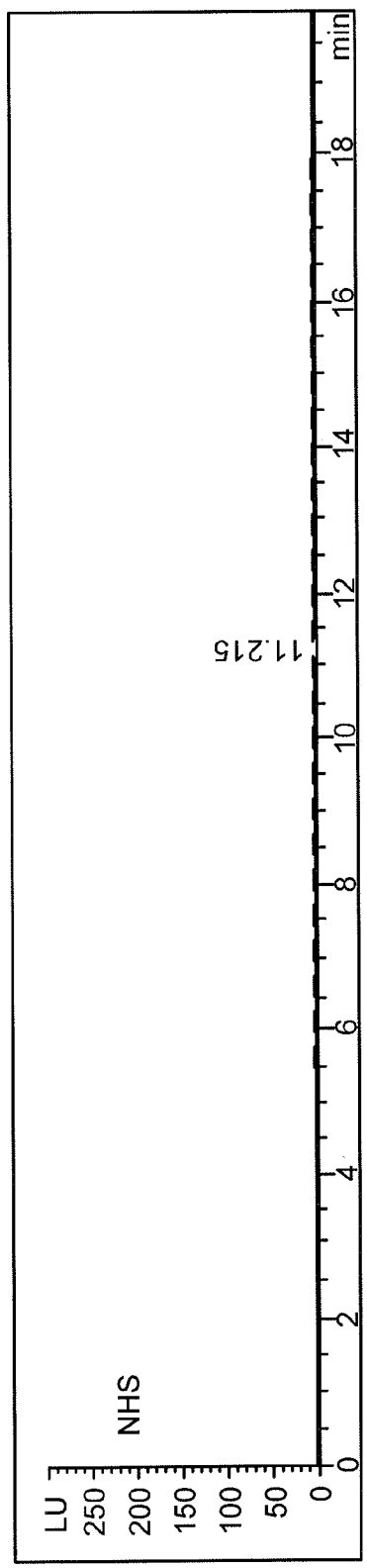
FIGS. 21A-21J show mobility shift profiles of Fl-labeled TNF-α incubated with normal human serum (NHS) in the presence of different amounts of ADL. Ex=494 nm; Em=519 nm. The addition of increasing amounts of ADL to the incubation mixture dose-dependently shifted the free TNF-Fl peak (FT) to the higher molecular mass eluting positions, while the internal control (IC) peak did not change.
Figure 21B:
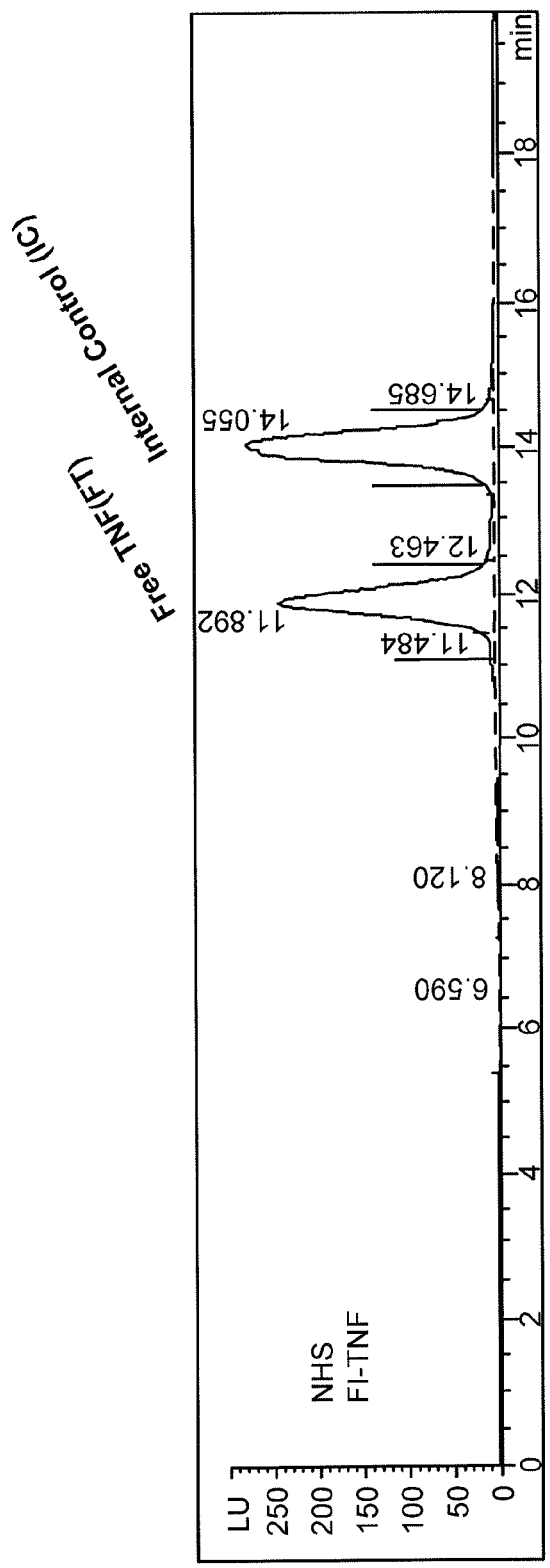
Figure 21C:
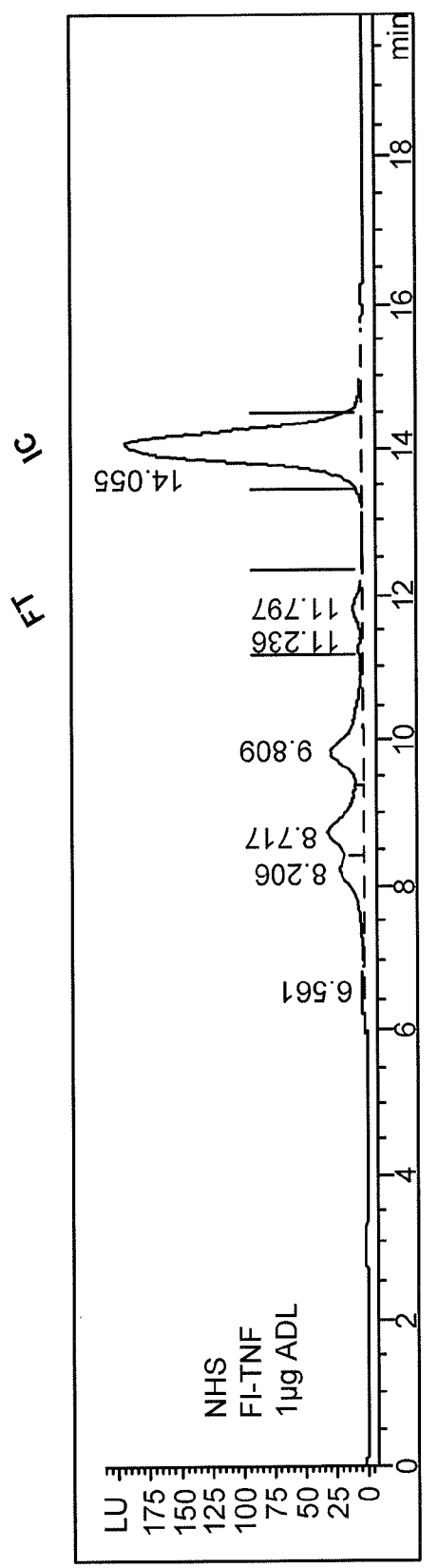
Figure 21D:
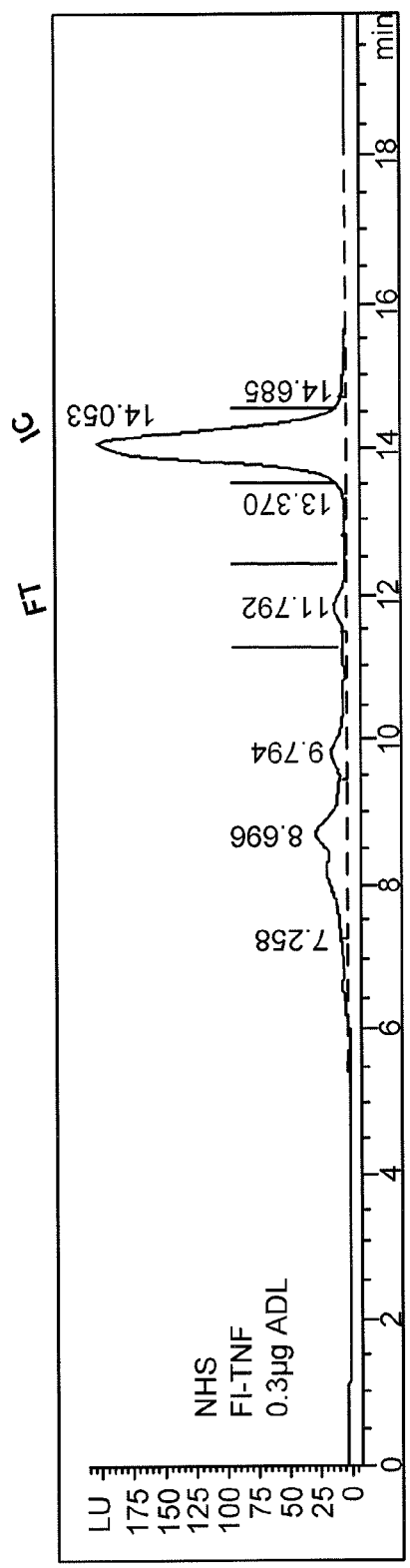
Figure 21E:
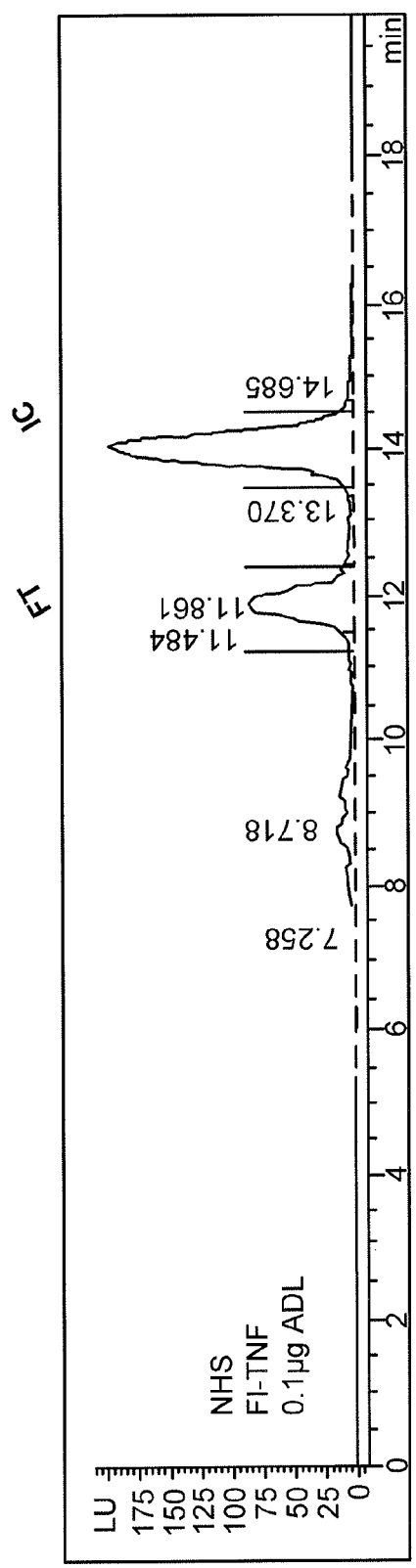
Figure 21F:
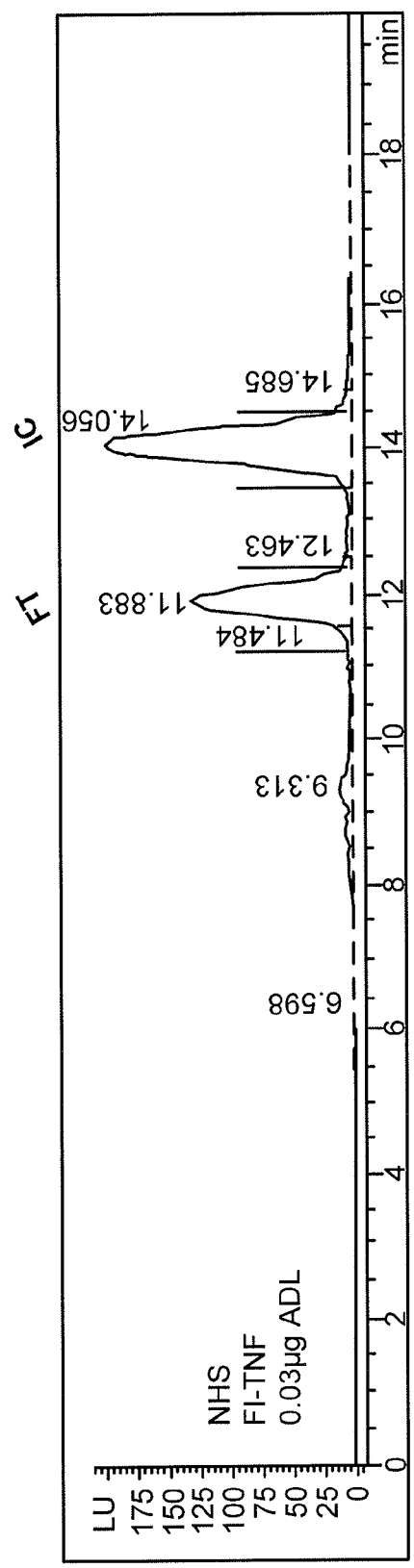
Figure 21G:
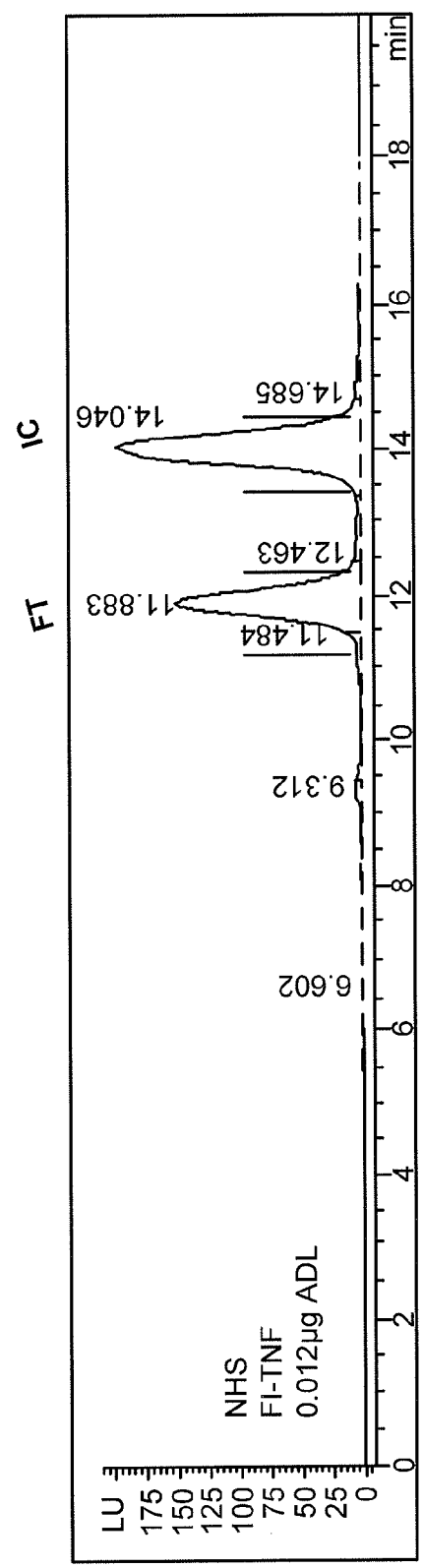
Figure 21H:
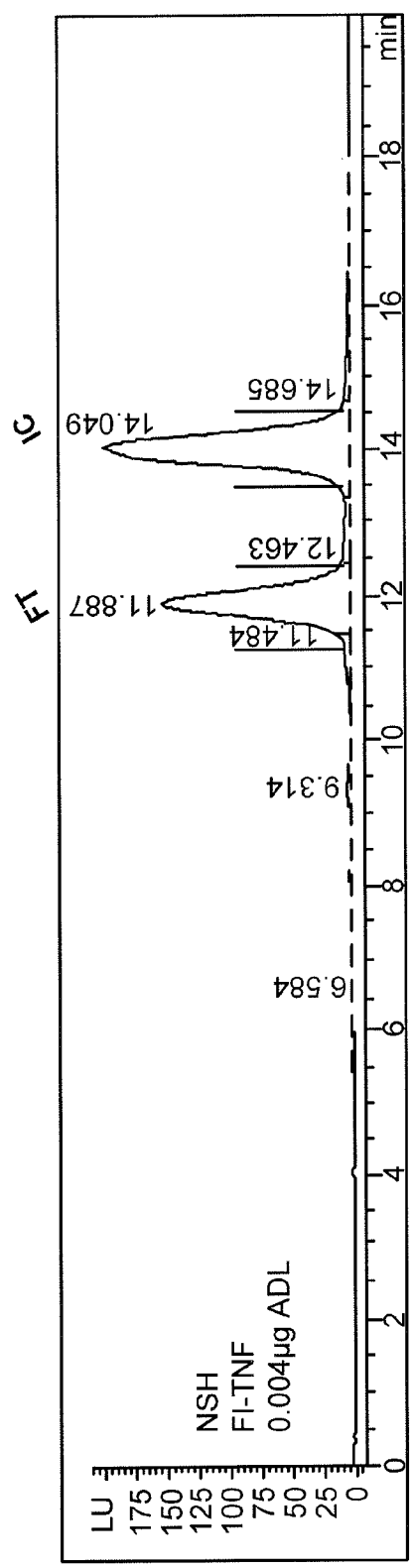
Figure 21I:
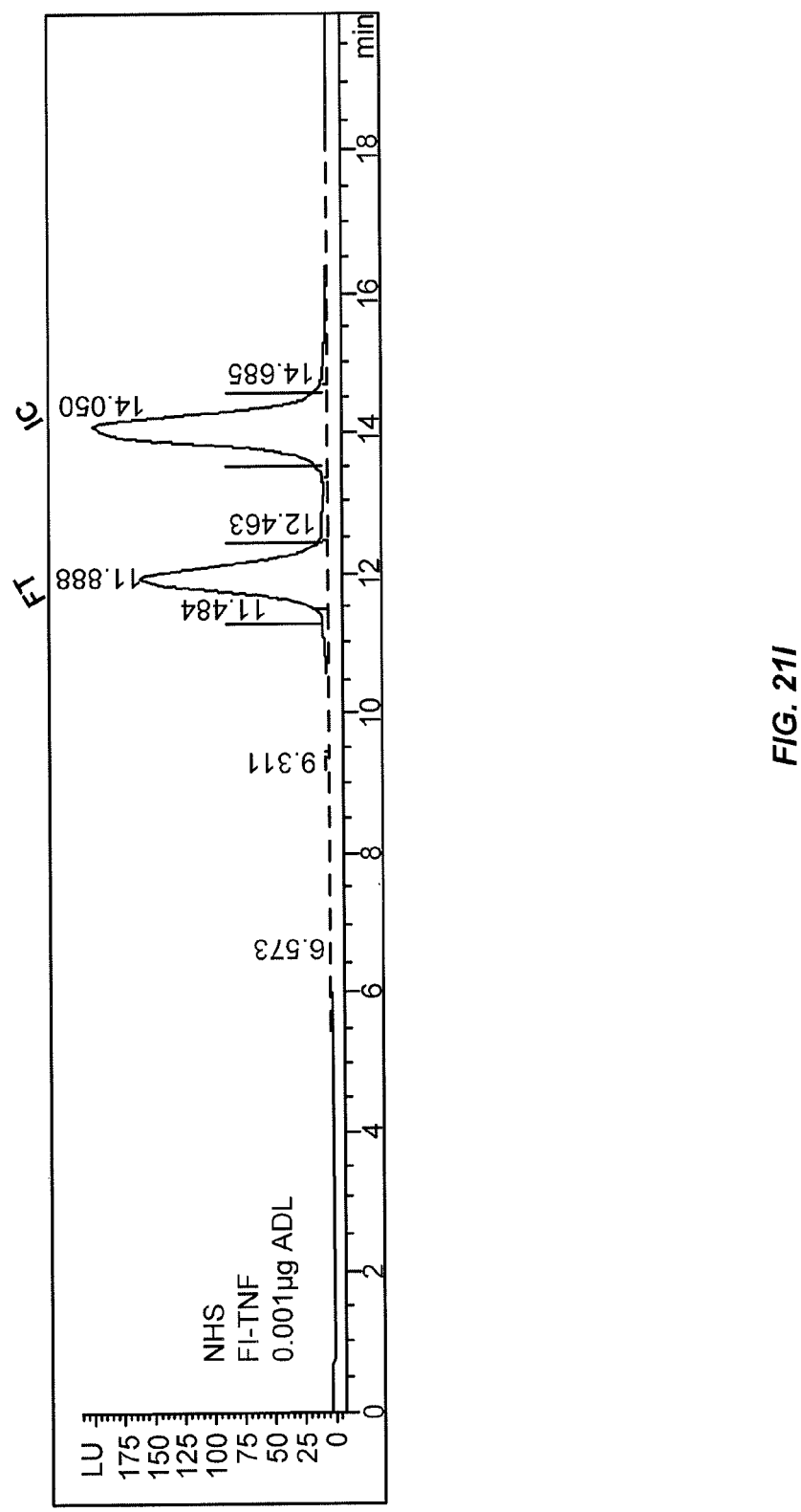
Figure 21J:
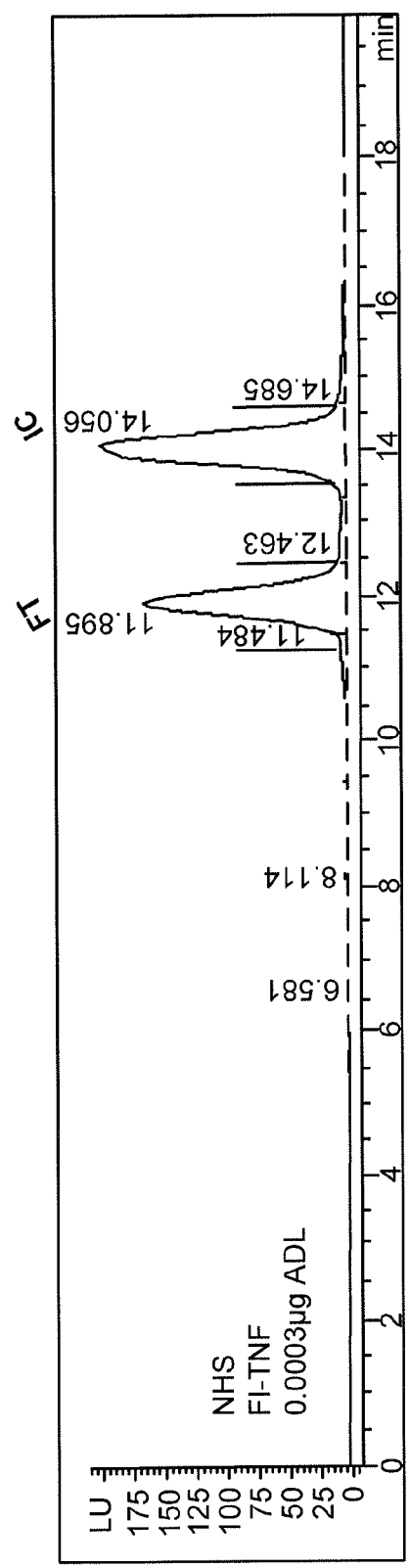

FIG. 20 shows the dose-response curve of the fluorescent peak shift caused by the addition of anti-human IgG. Increasing the concentration of anti-human IgG reduces the ratio of free ADL to internal control due to the formation of the immunocomplex. The assay sensitivity is 10 ng/ml of anti-human IgG. The internal control "Fl-BioCyt" corresponds to an Alexa Fluor® 488-biocytin (BioCyt) which combines the green-fluorescent Alexa Fluor® 488 fluorophore with biotin and an aldehyde-fixable primary amine (lysine) (Invitrogen Corp.; Carlsbad, Calif.).

FIGS. 21A-21J show the separation of the ADL bound TNF-α-Fl complex from the free TNF-α-Fl due to the mobility shift of the high molecular weight complex. As seen in panels 21C and 21J, the retention time of the fluorescent peak shifted from 11.9 min to 6.5-10.5 min. The more the ADL is added in the reaction mixture, the less the free TNF-α-Fl peak remains in the chromatogram and the more the immuno-complex is formed.

Figure 22:
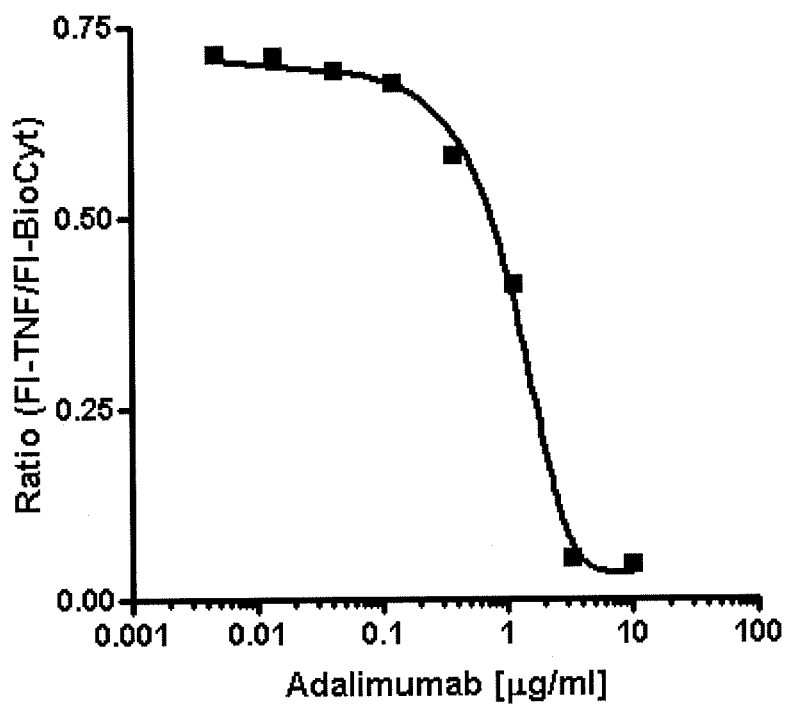
FIG. 22 shows a dose-response curve of ADL on the shift of free TNF-α-Fl. Increasing amounts of ADL were incubated with 100 ng of TNF-α-Fl and internal control. The more the antibody ADL was added to the reaction mixture the lower the ratio of free TNF-α-Fl to internal control.

FIG. 22 shows the dose-response curves of the TNF-α-Fl peak shift caused by the addition of ADL. Based on the added ADL, the detection limit is 10 ng/mL of ADL in serum.

Table 4 shows that serum samples from 100 healthy subjects and 114 IBD patients treated with ADL were analyzed for ADA and ADL levels using the mobility shift assay of the present invention. All 100 healthy subject samples had ADA levels below the limit of detection (no shift of the free Fl-ADL), whereas 5 out of the 114 patient samples had an ADA concentration of 0.012 to >20 µg/ml. The mean of ADL levels in 100 healthy subject samples was 0.76±1.0 µg/ml (range 0 to 9.4 µg/ml). The mean of ADL levels in 114 serum samples from patients treated with ADL was 10.8+17.8 µg/ml (range 0-139 µg/ml). Four out of five ADA positive samples had undetectable levels of ADL.

TABLE 4

Patient Serum Levels of ADA and ADL Measured by the Mobility Shift Assay

| | Subjects (n) | Sex (M/F) | Age (Years) (Mean) | ADA Positive | ADL level (µg/ml) |
|---|---|---|---|---|---|
| Healthy Control | 100 | 38/62 | 18-62 (37.1) | 0 | 0.76 ± 1.00 |
| IBD Patient Treated with ADL | 114 | 51/63 | 20-69 (39.9) | 5 (4.3%) | 10.80 ± 17.80 |

CONCLUSIONS

The mobility shift assay format used for measuring HACA/IFX is a homogeneous assay without the coating of antigens to a solid surface, and without multiple washing and incubation steps like a typical ELISA. This assay can be applied to measure ADA and anti-TNF drugs. The sensitivity of the assay (in µg/ml range) is higher for both ADA and ADL measurement with patient serum compared to ELISA methods (in mg/ml range). Healthy control serum samples did not cause mobility shift of the Fl-labeled ADL, and 4.3% of the patients treated with ADL were found to have ADA by this assay. Although healthy control serum samples caused mobility shift of the Fl-labeled TNF-α, which may have been due to the presence of soluble free receptor of TNF-α, the average of ADL in patients treated with ADL was much higher (10.8 vs. 0.76 mg/ml). Early detection of ADA and monitoring of ADL drug level while the patient is receiving ADL treatment will allow the physician to optimize the dosing of ADL or switch to another anti-TNF-α drug when appropriate and, thereby, optimizing the overall management of the patient's disease.

TABLE 5

Patient Serum Levels of ADA and ADL
Measured by the Mobility Shift Assay

| | Subjects (n) | Sex (M/F) | Age (Mean) | ADL Level (µg/ml) | ADA Positive |
|---|---|---|---|---|---|
| Healthy Control | 100 | 38/62 | 18-62 (37.1) | 0.76 ± 1.00 | 0 |
| IBD Patient Treated with ADL | 114 | 51/63 | 20-69 (39.9) | 10.80 ± 17.80 | 0-4 µg/ml ADL: 4 of 42 (9.52%) |

Using this mobility shift assay we analyzed serum samples from 100 healthy subjects, and 114 IBD patients treated with ADL, for ADA and ADL levels. All 100 healthy subject samples had ADA levels below the limit of detection (no shift of the free FI-ADL), whereas 4 out of the 42 patient samples with 0-4 µg/mL ADL had an average ADA concentration of 0.012 to >20 µg/ml. Mean ADL levels in 100 healthy subject samples was 0.76 + 1.0 mg/ml (range 0 to 9.4 mg/ml). Mean ADL levels in 114 serum samples from patients treated with ADL was 10.8 + 17.8 mg/ml (range 0-139 mg/ml). Four out of four ADA positive samples had undetectable levels of ADL. For the detection of ADA, the 114 IBD patients treated with ADL were divided into two categories, 0-4 µg/ml of ADL and >4 µg/ml of ADL. Patients with greater than 4 µg/ml of ADL will be tested with a larger amount of ADL-FI to address the competition of circulating ADL with ADL-FI.

Healthy control serum samples do not cause mobility shift of the FI-labeled ADL. In a preliminary study, 9.52% of patients with 0.4 µg/ml ADL were found to have ADA in this assay. Further evaluation of normal samples and patients samples with higher concentrations of ADL-FI will be done.

Example 7

Combinatorial Algorithm for Optimizing Anti-TNF Drug Therapy

This example describes methods for optimizing therapy, reducing toxicity, and/or monitoring the efficacy of therapeutic treatment by applying a statistical algorithm such as, e.g., a learning statistical classifier system, to one or more (e.g., a combination of two, three, four, five, six, seven, or more) biochemical markers, serological markers, and/or genetic markers. Accordingly, the methods set forth in the present example provide information useful for guiding treatment decisions for patients receiving anti-TNF drug therapy, e.g., by determining when or how to adjust or modify (e.g., increase or decrease) the subsequent dose of an anti-TNF drug, by determining when or how to combine an anti-TNF drug (e.g., at an increased, decreased, or same dose) with one or more immunosuppressive agents such as methotrexate (MTX) or azathioprine, and/or by determining when or how to change the current course of therapy (e.g., switch to a different anti-TNF drug).

As a non-limiting example, the presence, level, or genotype of one, two, three, four, five, or all six of the following classes of biochemical markers, serological markers, and/or genetic markers can be detected, measured, or determined in a patient sample (e.g., a serum sample from a patient on anti-TNF drug therapy):

(1) anti-TNF drug levels (e.g., levels of free anti-TNFα therapeutic antibody);
(2) anti-drug antibody (ADA) levels (e.g., level of autoantibody to the anti-TNF drug);
(3) TNFα levels;
(4) levels of one, two, three, four, five, six, seven, or more additional cytokines (e.g., IL-6, IL-1β, IFN-γ, IL-10, etc.) and/or markers for other mechanisms of inflammation (e.g., inflammatory markers such as CRP, SAA, ICAM-1, and/or VCAM-1);
(5) the presence or absence of one or more mutations in one or more genetic markers such as inflammatory pathway genes, e.g., the presence or absence of variant alleles (e.g., SNPs) in one or more inflammatory markers such as, e.g., NOD2/CARD15 (e.g., SNP 8, SNP 12, and/or SNP 13 described in U.S. Pat. No. 7,592,437), ATG16L1 (e.g., the rs2241880 (T300A) SNP described in Lakatos et al., *Digestive and Liver Disease*, 40 (2008) 867-873), IL23R (e.g., the rs11209026 (R381Q) SNP described in Lakatos et al.), the human leukocyte antigen (HLA) genes and/or cytokine genes described in, e.g., Gasche et al. (*Eur. J. Gastroenterology & Hepatology*, (2003) 15:599-606), and the DLG5 and/or OCTN genes from the IBD5 locus;
(6) levels of one or more of the above biochemical markers and/or serological markers at multiple time points (e.g., at 28 weeks, 60 weeks, etc.); and
(7) combinations thereof.

A single statistical algorithm or a combination of two or more statistical algorithms described herein can then be applied to the presence, concentration level, or genotype of the markers detected, measured, or determined in the sample to thereby optimize therapy, reduce toxicity, or monitor the efficacy of therapeutic treatment with the anti-TNF drug. As such, the methods described in this example find utility in determining patient management by determining patient immune status.

Table 6 below provides a summary of cytokine levels in normal and patient samples.

TABLE 6

| | Sample | IFN-γ | IL-1β | IL-6 | TNF-α |
|---|---|---|---|---|---|
| Normal Control n = 64 | Mean ± SD (pg/mL) | 0.88 ± 2.71 | 0.17 ± 0.72 | 0.66 ± 0.58 | 1.78 ± 0.71 |
| | Range (pg/mL) | 0.00-141.42 | 0.00-44.41 | 0.12-31.70 | 0.36-23.83 |
| | Mean ± 2SD(pg/mL) | 6.3 | 1.6 | 1.82 | 3.19 |
| | Positive/Total | 5/64 | 2/64 | 11/64 | 3/64 |
| UC Samples (IFX treated) n = 43 | Mean ± SD (pg/mL) | 1.96 ± 2.24 | 0.13 ± 0.08 | 0.86 ± 1.23 | 6.08 ± 6.54 |
| | Range (pg/mL) | 0.00-9.34 | 0.01-0.42 | 0.12-5.60 | 0.13-35.54 |
| | Positive/Total | 3/43 (7.0%) | 0/43 (0.0%) | 5/43 (11.6%) | 34/43 (79.1%) |
| Humira Treated CD samples n = 117 | Mean ± SD (pg/mL) | 2.88 ± 4.25 | 0.59 ± 1.22 | 1.56 ± 1.55 | 8.03 ± 21.40 |
| | Range (pg/mL) | 0.00-36.29 | 0.00-8.59 | 0.17-11.93 | 0.49-207.29 |
| | Positive/Total | 14/117 (12.0%) | 11/117 (9.4%) | 35/117 (29.9%) | 67/117 (57.3%) |
| HACA positive samples n = 94 | Mean ± SD (pg/mL) | 6.21 ± 12.12 | 4.36 ± 37.7 | 3.58 ± 6.35 | 21.16 ± 32.78 |
| | Range (pg/mL) | 0.18-98.87 | 0-366.11 | 0.09-2302.4 | 0.09-176.12 |
| | Positive/Total | 25/94 (26.60%) | 4/94 (4.3%) | 39/94 (41.5%) | 62/94 (66.0%) |

For purposes of illustration only, the following scenarios provide a demonstration of how the methods of the present invention advantageously enable therapy to be optimized and toxicity (e.g., side-effects) to be minimized or reduced based upon the presence, level, and/or genotype of one or more biochemical markers, serological markers, and/or genetic markers as described herein. In each of the following scenarios, one, two, or more statistical algorithms can then be applied to optimize therapy and/or reduce toxicity associated with the anti-TNF drug.

Scenario #1: High Level of Anti-TNF Drug with Low Level of Anti-Drug Antibody (ADA) and Low Levels of Inflammatory Cytokines.

Drug levels=10-50 ng/10 µl; ADA levels=0.1-2 ng/10 µl; TNFα levels=1-8 pg/ml; IL-6 levels=0.1-3 pg/ml; IL-1β levels=0.0-2 pg/ml; IFN-γ levels=0-6 pg/ml; antibody against IL-10 not detected. Patient samples having this marker profile include samples from patients BAB and JAA on visit 10 ("V10"). See, FIG. 16B.

Patients receiving anti-TNF drug therapy and having this particular marker profile should be treated with immunosuppressive drugs like azathioprine along with the anti-TNF drug (e.g., infliximab).

Scenario #2: Medium Level of Anti-TNF Drug with Low Level of ADA and Low Levels of Inflammatory Cytokines.

Drug levels=5-20 ng/10 µl; ADA levels=0.1-2 ng/10 µl; TNFα levels=1-8 pg/ml; IL-6 levels=0.1-3 pg/ml; IL-1β levels=0.0-2 pg/ml; IFN-γ levels=0-6 pg/ml; antibody against IL-10 not detected. Patient samples having this marker profile include samples from patients DGO, JAG, and JJH on visit 10 ("V10"). See, FIG. 16b.

Patients receiving anti-TNF drug therapy and having this particular marker profile should be treated with immunosuppressive drugs like azathioprine along with a higher dose of the anti-TNF drug (e.g., infliximab). One skilled in the art will know of suitable higher or lower doses to which the current course of therapy can be adjusted such that drug therapy is optimized, e.g., a subsequent dose that is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher or lower than the current dose.

Scenario #3: Medium Level of Anti-TNF Drug with Medium Level of ADA and Low Levels of Inflammatory Cytokines.

Drug levels=5-20 ng/10 µl; ADA levels=0.5-10 ng/10 µl; TNFα levels=1-8 pg/ml; IL-6 levels=0.1-3 pg/ml; IL-1β levels=0.0-2 pg/ml; IFN-γ levels=0-6 pg/ml; antibody against IL-10 not detected. Patient samples having this marker profile include samples from patient JMM on visit 10 ("V10") and patient J-L on visit 14 ("V14"). See, FIG. 16B.

Patients receiving anti-TNF drug therapy and having this particular marker profile should be treated with a different drug. As a non-limiting example, a patient on infliximab (IFX) therapy and having medium levels of IFX and ADA (i.e., HACA) with low levels of inflammatory cytokines should be switched to therapy with adalimumab (HUMIRA™).

Scenario #4: Low Level of Anti-TNF Drug with High Level of ADA and High Levels of Inflammatory Cytokines.

Drug levels: 0-5 ng/10 µl; ADA levels=3.0-50 ng/10 µl; TNFα levels=10-60 pg/ml; IL-6 levels=0.1-50 pg/ml; IL-1β levels=0.0-366 pg/ml; IFN-γ levels=0.15-100 pg/ml; antibody against IL-10 not detected. Patient samples having this marker profile include samples from all patients on visit 14 ("V14") in FIG. 16B.

Patients receiving anti-TNF drug therapy and having this particular marker profile should be treated with a different drug. As a non-limiting example, a patient on infliximab (IFX) therapy and having a low level of IFX with high levels of ADA (i.e., HACA) and inflammatory cytokines should be switched to therapy with adalimumab (HUMIRA™).

Scenario #5: High Levels of Inflammatory Cytokines.

High TNFα levels (e.g., 10-60 pg/ml); high IL-6 levels (e.g., 0.1-50 pg/ml); high IL-1β levels (e.g., 0.0-366 pg/ml); high IFN-γ levels (e.g., 0.15-100 pg/ml); high levels of other inflammatory molecules; +/−antibodies against anti-inflammatory cytokines (e.g., antibody against IL-10 either detected or not detected).

Patients receiving anti-TNF drug therapy and having this particular marker profile should either be treated with a different drug or treated with immunosuppressive drugs like methotrexate (MTX) or azathioprine (AZA) along with a higher dose of the anti-TNF drug. In particular, this marker profile of high levels of inflammatory cytokines from a patient on infliximab (IFX) therapy indicates that the current course of therapy is not working and the patient should be switched to therapy with adalimumab (HUMIRA™) or should be treated with one or more immunosuppressive drugs along with a higher dose of IFX.

Example 8

Determination of Different Anti-Drug Antibody (ADA) Isotypes

This example describes the determination of different anti-drug antibody (ADA) isotypes in ADA-positive patients receiving anti-TNF drug therapy. Non-limiting examples of antibody isotypes include IgA, IgD, IgE, IgG, and IgM. In certain aspects, the detection of the presence or level of a specific ADA isotype or a particular combination of ADA isotypes is associated with different clinical outcomes.

Figure 23:
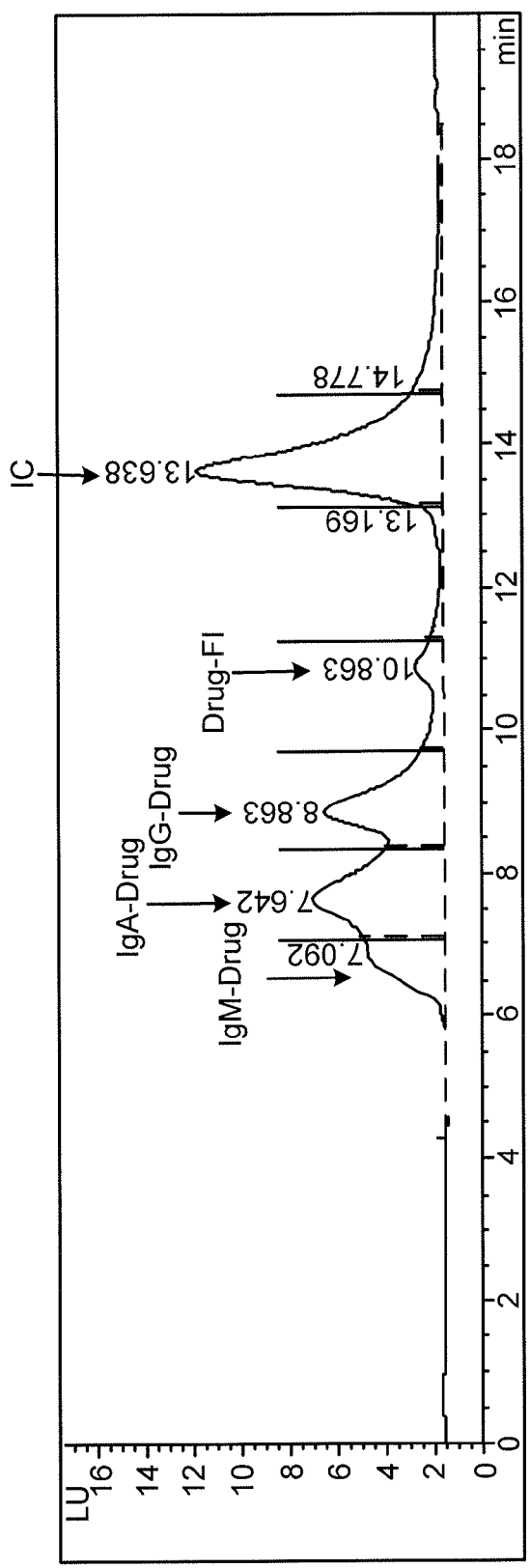
FIG. 23 shows the elution times of different ADA isotypes in HACA-positive patient serum.

FIG. 23 shows the elution times of different ADA isotypes in HACA-positive patient serum. In particular embodiments, the therapeutic implications of anti-TNF drug therapy can be determined based upon whether the ADA is an IgM isotype (retention time: ~6.5-7.5 minutes), IgA isotype (7.5-8.5 minutes), or IgG isotype (8.5-9.5 minutes) based on size and appropriate dilution experiments. The retention times for labeled anti-TNF drugs such as Humira and Remicade is about 10.8 minutes, and the retention time for the internal control (IC) is about 13.5 minutes.

In one study, 200 patient samples were assayed in accordance with the methods of the present invention for detecting ADA by size exclusion chromatography. Samples 1-100 were controls (e.g., normal healthy control samples), while samples 101-200 were obtained from patients receiving Remicade therapy and were HACA-positive by the Bridge assay. An unadjusted plot of signal intensity (Y-axis) versus elution time (X-axis) was generated for all 200 samples. The following three adjustments were then made to the plot: (1) Standardized Y (low) to the baseline on the left; (2) Standardized Y (high) to the control peak on the right; and (3) Standardized X to the control peak on the right.

Figure 24:
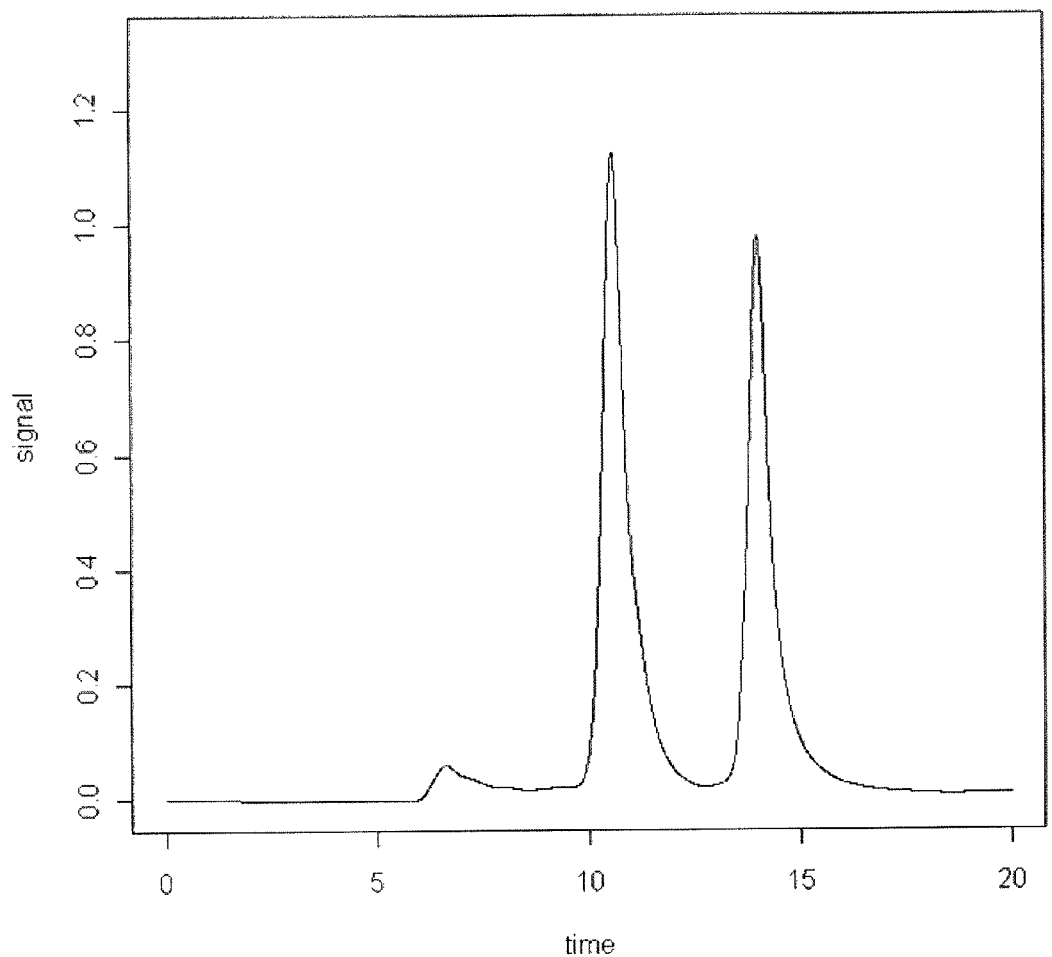
FIG. 24 shows a plot of the mean of the 100 control samples used in the study described in Example 8.
Figure 25:
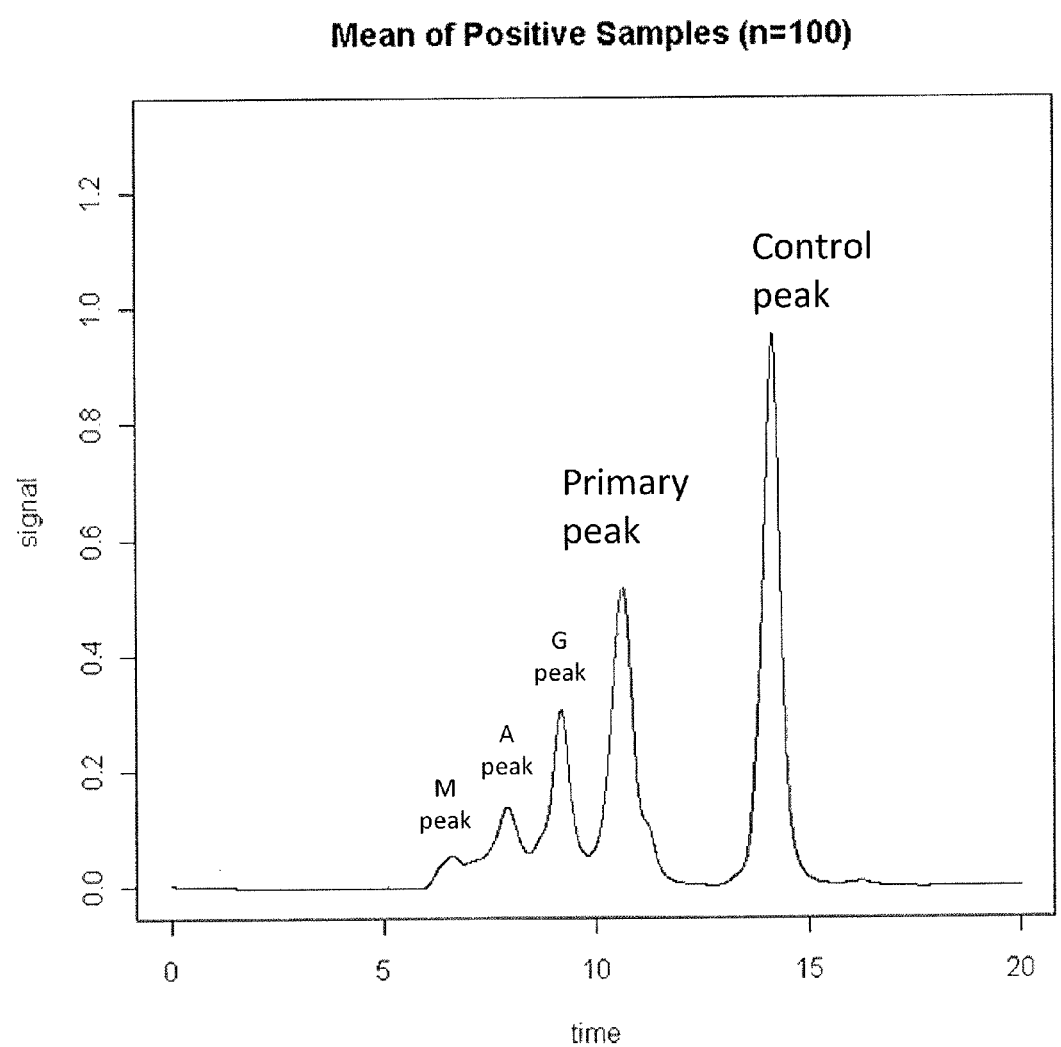
FIG. 25 shows a plot of the mean of the 100 HACA-positive samples used in the study described in Example 8.

The data from all 200 samples were split into the 100 control samples and the 100 HACA-positive samples and then averaged. FIG. 24 shows a plot of the mean of the control samples. FIG. 25 shows a plot of the mean of the positive samples. Notably, a comparison of the plots in FIGS. 24 and 25 shows a decrease in the signal intensity for labeled Remicade ("Primary Peak") and the appearance of two distinct ADA isotype peaks, corresponding to HACA IgA ("A peak") and HACA IgG ("G peak").

Figure 26:
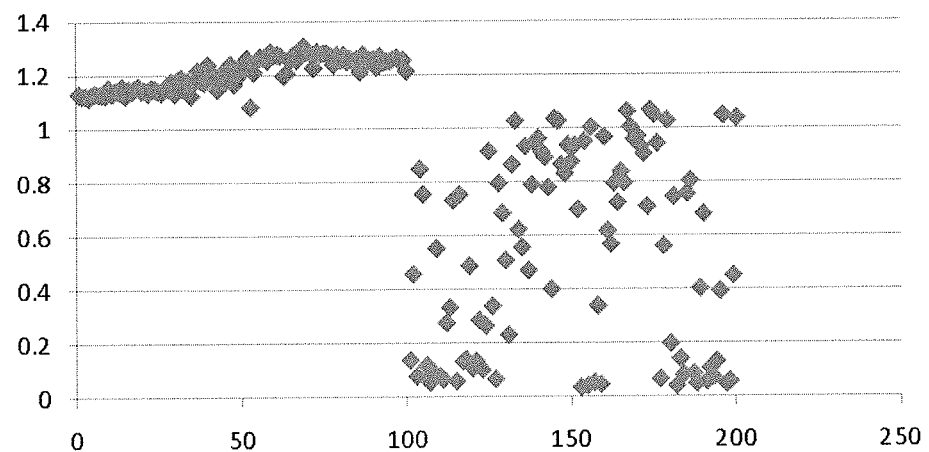
FIG. 26 illustrates a side-by-side comparison of the Primary Peak signals (i.e., corresponding to labeled Remicade signal intensity) for the 100 control samples and the 100 HACA-positive samples used in the study described in Example 8.
Figure 27:
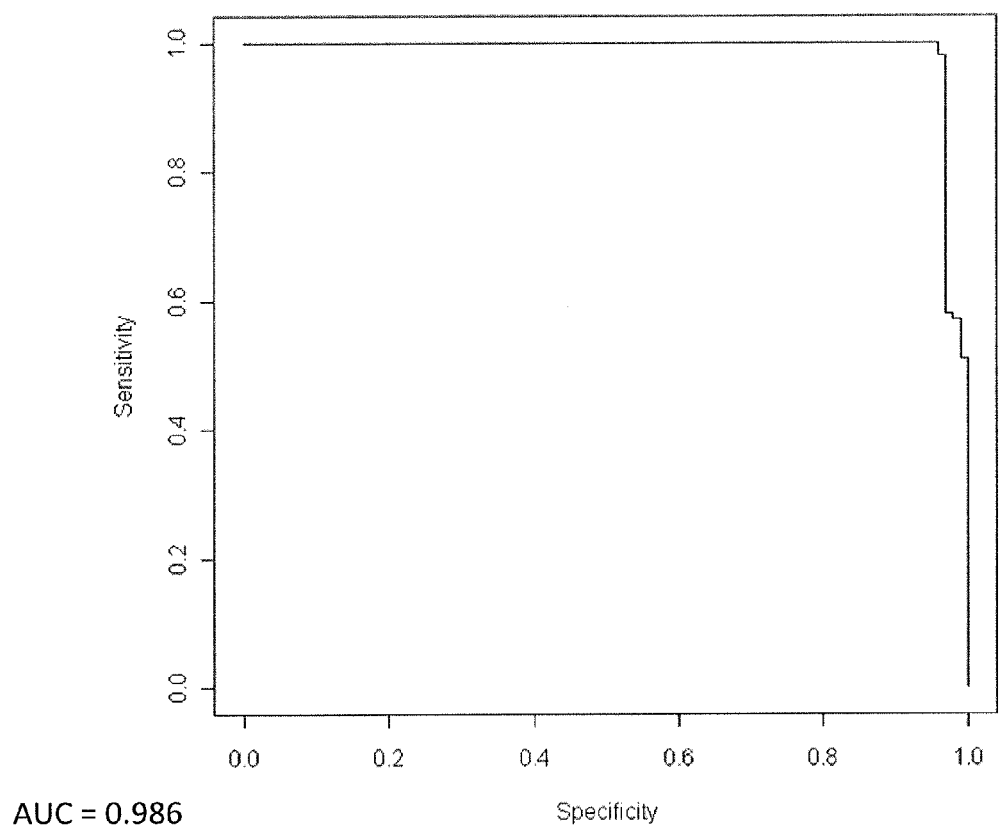
FIG. 27 shows a Receiver Operating Characteristic (ROC) curve for the Primary Peak data from FIG. 26. The Area Under the Curve (AUC) was 0.986.

FIG. 26 illustrates a side-by-side comparison of the Primary Peak signals (i.e., corresponding to labeled Remicade signal intensity) for the 100 control samples and the 100 positive samples. Values shown are average values from elution times 9.71 to 12.23 minutes. In particular, FIG. 26 shows decrease in the signal intensity for labeled Remicade for the 100 HACA-positive samples, which correlates to the formation of complexes between the labeled Remicade and HACA. FIG. 26 also shows that a number of positive samples had a high level of HACA, as evidenced by the low Primary Peak signals (e.g., between 0 and 0.2 on the X-axis). FIG. 27 shows a Receiver Operating Characteristic (ROC) curve for the Primary Peak data from FIG. 26. The Area Under the Curve (AUC) was 0.986.

Figure 28:
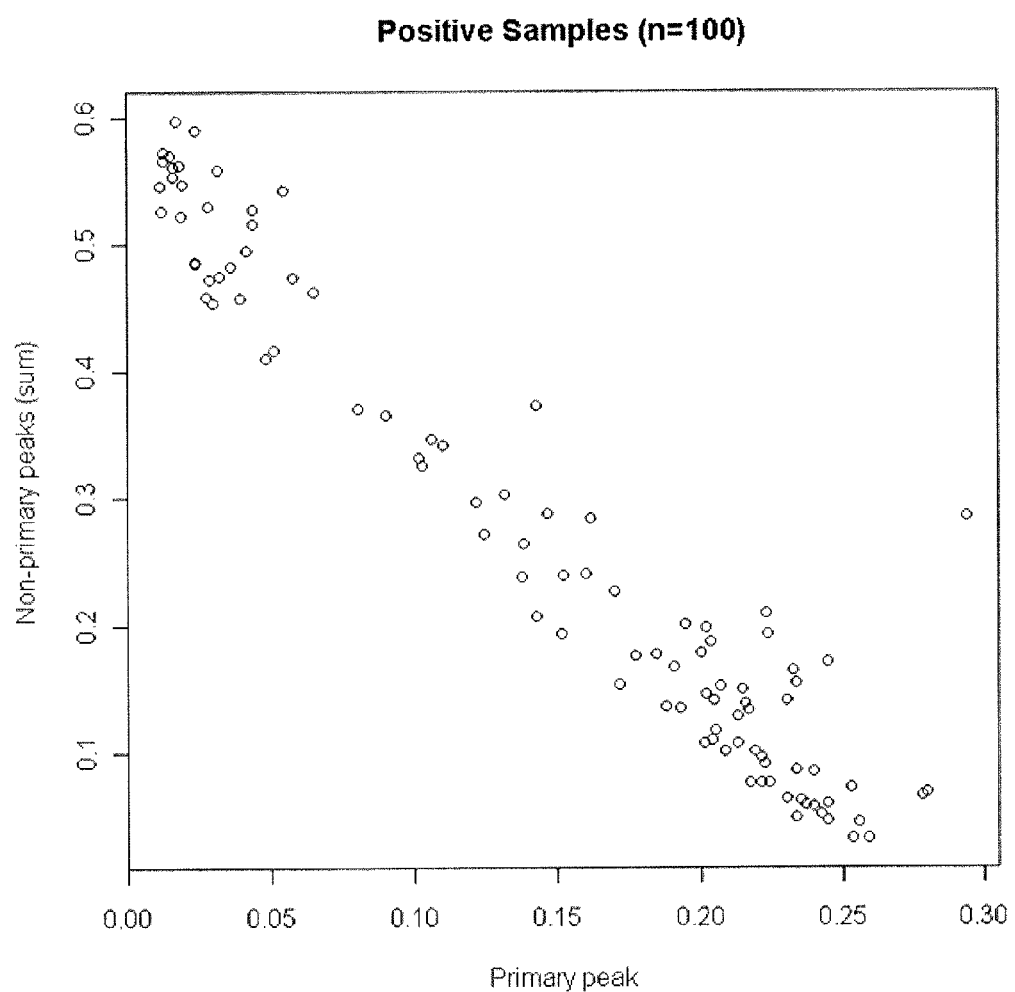
FIG. 28 shows a plot of Non-primary peaks on the X-axis (which correspond to the sum of the IgG, IgA, and IgM peaks) versus the Primary Peak on the Y-axis for the 100 HACA-positive samples used in the study described in Example 8.
Figure 29:
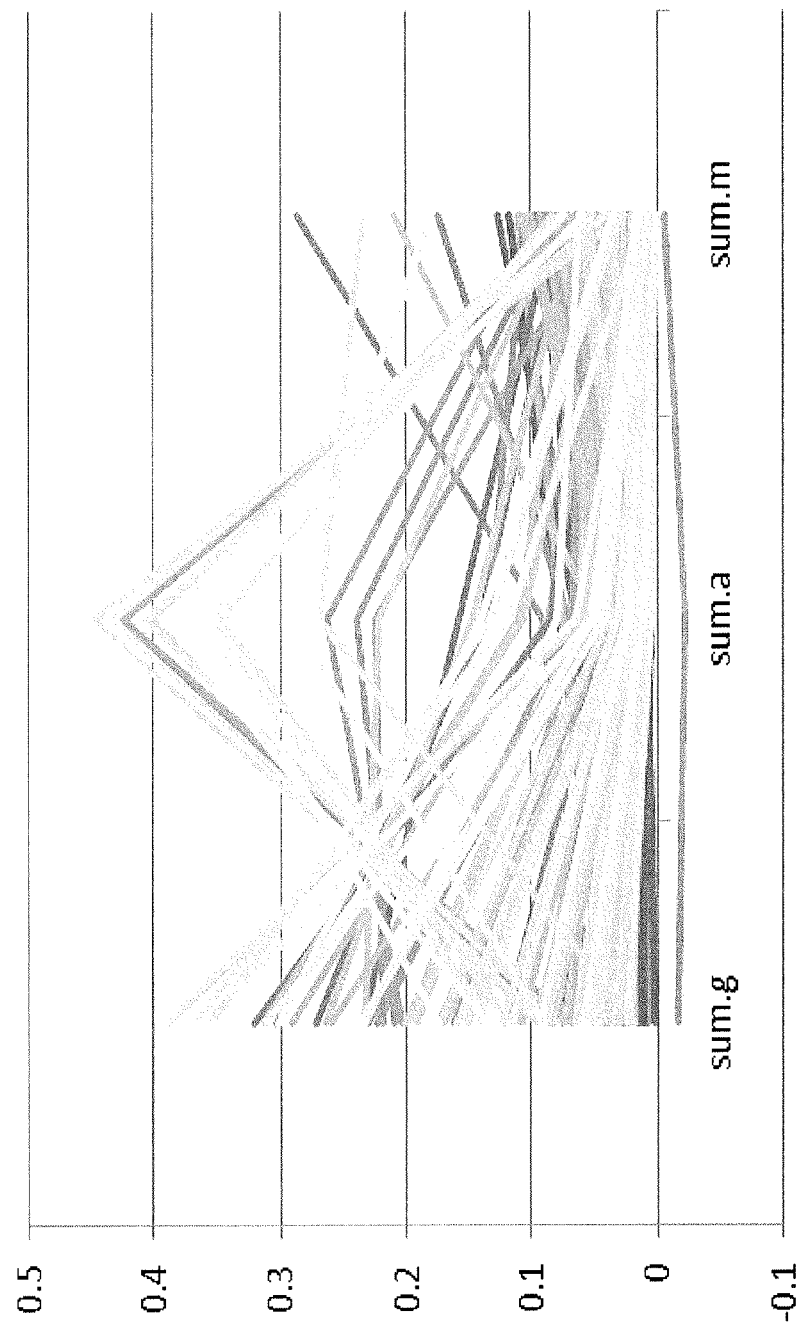
FIG. 29 shows a plot of the IgG versus IgA versus IgM peaks for all 200 samples used in the study described in Example 8.

Next, the average values for the Primary Peak versus the sum of the other peaks (IgG, IgA, and IgM) were plotted. FIG. 28 shows a plot of Non-primary peaks on the X-axis (which correspond to the sum of the IgG, IgA, and IgM peaks) versus the Primary Peak on the Y-axis for the 100 HACA-positive samples. The linear relationship illustrated in this plot may be used as an assay check (i.e., an assay control). FIG. 29 shows a plot of the IgG versus IgA versus IgM peaks for all 200 samples.

Example 9

Proximity-Based Determination of Different ADA Isotypes

This example describes an exemplary embodiment of the present invention for the determination of different anti-drug antibody (ADA) isotypes such as different isotypes of ATI (i.e., antibody to IFX; "HACA") in ADA-positive patients receiving anti-TNFα drug therapy such as infliximab (IFX). Non-limiting examples of antibody isotypes such as ATI isotypes include IgA, IgD, IgE, IgG, and IgM (e.g., IgA ATI, IgD ATI, IgE ATI, IgG ATI, and IgM ATI). In certain aspects, the detection of the presence or level of a specific ADA isotype or a particular combination of ADA isotypes is associated with different clinical outcomes.

Figure 30:
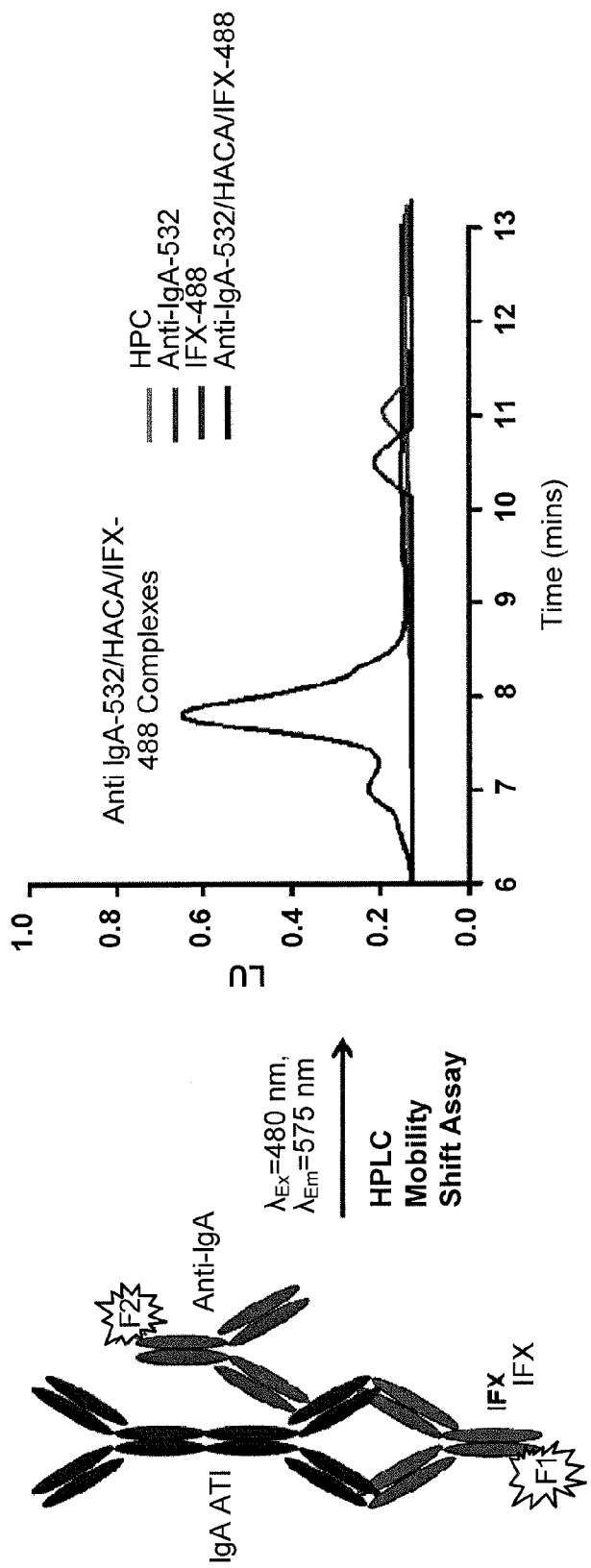
FIG. 30 shows a schematic of a fluorescence resonance energy transfer (FRET) autoantibody isotyping assay format of the present invention.
Figure 31:
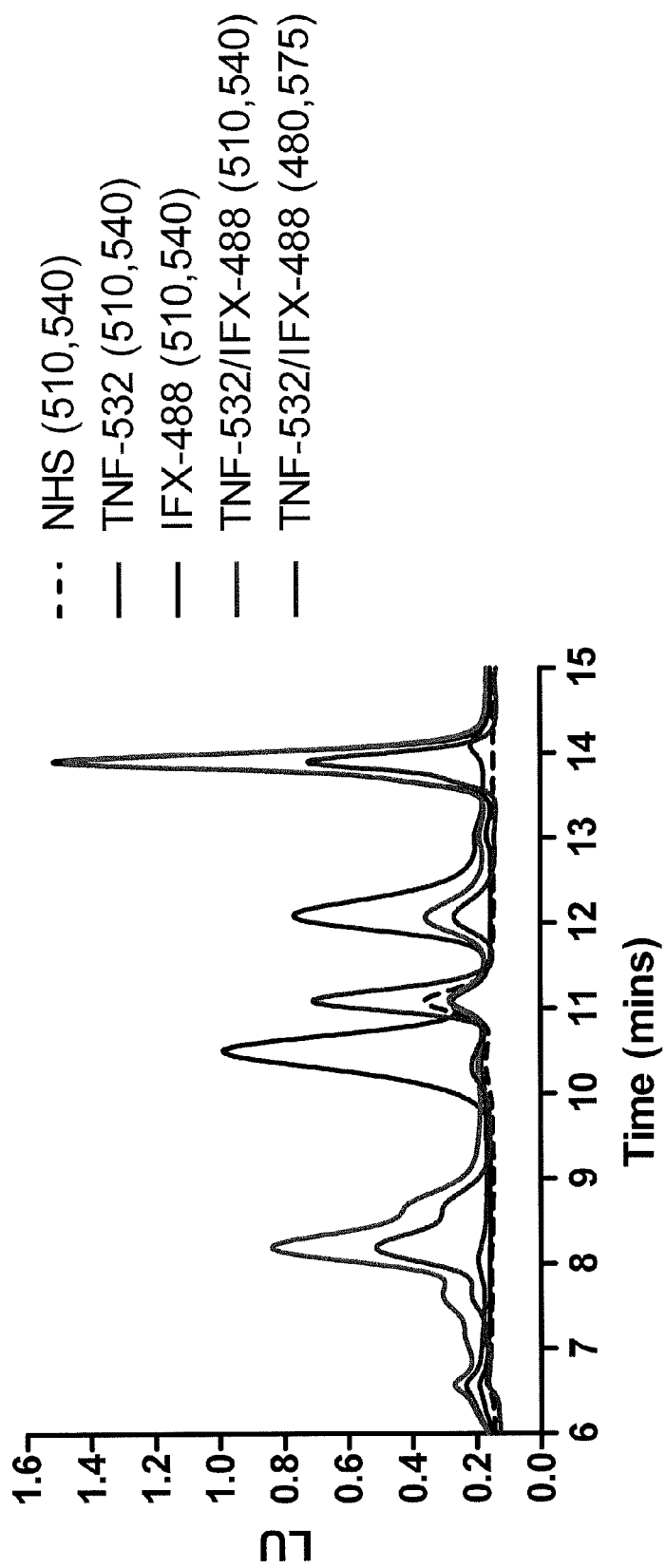
FIG. 31 shows the results of a FRET-based autoantibody isotyping assay of the present invention.

FIGS. 30 and 31 illustrate embodiments of the proximity-based isotyping assay of the present invention for determining the presence (or absence) or level of at least one, two, three, four, five, or more ATI isotypes such as, e.g., IgA ATI, IgD ATI, IgE ATI, IgG ATI, and/or IgM ATI isotypes using fluorescence resonance energy transfer (FRET). For example, FIG. 30 shows a schematic illustrating that Alexa-532 ("F2" label on an anti-Ig antibody such as anti-IgA) is excited by Alexa-488 ("F1" label on antibody therapeutic such as IFX) only when both fluorophores are in close proximity, thereby indicating the presence and/or level of a ternary complex of an anti-Ig (e.g., anti-IgA), HACA (e.g., IgA ATI), and IFX. In particular embodiments, different ATI isotypes and/or subclasses thereof can be determined using different anti-Ig's labeled with the same or different fluorophores such as, e.g., Alexa-532. FIG. 31 shows the results of a FRET-based isotyping assay of the present invention.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for detecting the presence or level of an IgA isotype and an IgG isotype of an autoantibody to an anti-TNFα drug in a sample, the method comprising:
    (a) contacting a labeled anti-TNFα drug, a labeled anti-Ig antibody specific for the IgA isotype, and a labeled anti-Ig antibody specific for the IgG isotype with a sample having or suspected of having the IgA isotype and the IgG isotype to form (i) a first labeled complex between the labeled anti-TNFα drug, the labeled anti-Ig antibody specific for the IgA isotype, and the IgA isotype, and (ii) a second labeled complex between the labeled anti-TNFα drug, the labeled anti-Ig antibody specific for the IgG isotype, and the IgG isotype, wherein the labeled anti-TNFα drug and the labeled anti-Ig antibodies comprise different labels;
    (b) subjecting the first and second labeled complexes to size exclusion chromatography to separate the first and second labeled complexes from each other, from free labeled anti-TNFα drug, and/or from free labeled anti-Ig antibodies; and
    (c) detecting the first and second labeled complexes, thereby detecting the presence or level of an IgA isotype and an IgG isotype of the autoantibody to the anti-TNFα drug;
    wherein the method uses anti-Ig antibodies specific for the IgA and IgG isotypes only and wherein only the IgA and IgG isotypes are detected.

2. The method of claim 1, wherein the anti-TNFα drug is selected from the group consisting of infliximab, adalimumab, etanercept, certolizumab pegol, and combinations thereof.

3. The method of claim 1, wherein the autoantibody to the anti-TNFα drug is selected from the group consisting of a human anti-chimeric antibody (HACA), a human anti-humanized antibody (HAHA), a human anti-mouse antibody (HAMA), and combinations thereof.

4. The method of claim 1, wherein the labeled anti-TNFα drug and the labeled anti-Ig antibodies bind to different epitopes.

5. The method of claim 1, wherein the sample is whole blood, serum, or plasma.

6. The method of claim 1, wherein the autoantibody to the anti-TNFα drug is a HACA and the sample is obtained from a subject receiving infliximab therapy.

7. The method of claim 1, wherein the autoantibody to the anti-TNFα drug is a HAHA and the sample is obtained from a subject receiving adalimumab therapy.

8. The method of claim 1, wherein the labeled anti-TNFα drug is a fluorophore-labeled anti-TNFα drug.

9. The method of claim 1, wherein the labeled anti-Ig antibodies are fluorophore-labeled anti-Ig antibodies.

10. The method of claim 1, wherein the labeled anti-Ig antibodies each comprise the same label or different labels.

11. The method of claim 1, wherein the first and second labeled complexes are detected using fluorescence label detection.

12. The method of claim 1, wherein the first labeled complex is detected by detecting a signal that is generated by proximity binding of both the labeled anti-TNFα drug and the labeled anti-Ig antibody specific for the IgA isotype to the IgA isotype of the autoantibody; and wherein the second labeled complex is detected by detecting a signal that is generated by proximity binding of both the labeled anti-TNFα drug and the labeled anti-Ig antibody specific for the IgG isotype to the IgG isotype of the autoantibody.

13. The method of claim 12, wherein the signal is a fluorescent signal that is detected by fluorescence resonance energy transfer (FRET).

14. The method of claim 1, wherein the size exclusion chromatography is size exclusion-high performance liquid chromatography (SE-HPLC).

15. The method of claim 1, wherein the method comprises detecting the presence or level of subclasses of the IgA isotype and the IgG isotype.

* * * * *